US011471173B2

(12) United States Patent
Thibodeau et al.

(10) Patent No.: US 11,471,173 B2
(45) Date of Patent: Oct. 18, 2022

(54) MULTI-BARREL DRILL GUIDE AND ANCHOR DEPLOYMENT ASSEMBLY

(71) Applicant: CONMED CORPORATION, Utica, NY (US)

(72) Inventors: Robert A. Thibodeau, St. Petersburg, FL (US); Gregory A. Alfonso, Tampa, FL (US); Matthew C. Summitt, Palm Harbor, FL (US); Robert A. Rofman, St. Petersburg, FL (US)

(73) Assignee: CONMED CORPORATION, Utica, NY (US)

( * ) Notice: Subject to any disclaimer, the term of this patent is extended or adjusted under 35 U.S.C. 154(b) by 361 days.

(21) Appl. No.: 16/619,583

(22) PCT Filed: Jun. 5, 2018

(86) PCT No.: PCT/US2018/036011
§ 371 (c)(1),
(2) Date: Dec. 5, 2019

(87) PCT Pub. No.: WO2018/226663
PCT Pub. Date: Dec. 13, 2018

(65) Prior Publication Data
US 2020/0155177 A1 May 21, 2020

Related U.S. Application Data

(60) Provisional application No. 62/649,181, filed on Mar. 28, 2018, provisional application No. 62/618,817, filed on Jan. 18, 2018, provisional application No. 62/516,733, filed on Jun. 8, 2017, provisional appli
(Continued)

(51) Int. Cl.
*A61B 17/17* (2006.01)
*A61B 17/04* (2006.01)
(Continued)

(52) U.S. Cl.
CPC ...... *A61B 17/1796* (2013.01); *A61B 17/0401* (2013.01); *A61B 17/1631* (2013.01);
(Continued)

(58) Field of Classification Search
CPC .. A61B 17/1796; A61B 17/17; A61B 17/1631
See application file for complete search history.

(56) References Cited

U.S. PATENT DOCUMENTS 4,744,353 A 5/1988 Mcfarland
5,012,818 A 5/1991 Joishy
(Continued)

FOREIGN PATENT DOCUMENTS

EP 1987779 A1 11/2008
EP 2422711 A2 2/2012
(Continued)

OTHER PUBLICATIONS

KR Office Action, App. No. 10-2020-7000134, dated Jul. 26, 2021, pp. 1-7.
(Continued)

*Primary Examiner* — Christian A Sevilla
(74) *Attorney, Agent, or Firm* — Bond, Schoeneck & King, PLLC; Frederick J. M. Price

(57) ABSTRACT

A multi-barrel drill guide and anchor deployment assembly with an elongated body extending along a longitudinal axis having a proximal end and a distal end, an elongated distal guide tube attached to and extending from the distal end, a handle extending from the elongated body between the proximal end and the distal end, and a sliding inserter movably connected to the elongated body and configured to move between the proximal and distal ends of the elongated body. The elongated body has a first channel extending from the proximal end to the distal end and a second channel extending from the distal end to a position between the distal
(Continued)

and proximal ends. The second channel extends at an angle relative to the first channel and intersects the first channel at a convergence area at the distal end.

20 Claims, 65 Drawing Sheets

Related U.S. Application Data cation No. 62/515,082, filed on Jun. 5, 2017, provisional application No. 62/515,033, filed on Jun. 5, 2017.

(51) Int. Cl.
*A61B 17/16* (2006.01)
*A61B 17/00* (2006.01)

(52) U.S. Cl.
CPC .............. *A61B 2017/00398* (2013.01); *A61B 2017/00734* (2013.01); *A61B 2017/0409* (2013.01)

(56) References Cited

U.S. PATENT DOCUMENTS

| | | | |
|---|---|---|---|
| 5,180,388 | A | 1/1993 | DiCarlo |
| 5,250,055 | A | 10/1993 | Moore et al. |
| 5,306,278 | A | 4/1994 | Dahl et al. |
| 5,324,295 | A | 6/1994 | Shapiro |
| 5,531,751 | A | 7/1996 | Schultheiss et al. |
| 5,637,112 | A | 6/1997 | Moore et al. |
| 5,741,266 | A | 4/1998 | Moran et al. |
| 5,749,889 | A | 5/1998 | Bacich et al. |
| 5,961,530 | A | 10/1999 | Moore et al. |
| 6,063,088 | A * | 5/2000 | Winslow ............... A61F 2/4611 606/279 |
| 6,379,364 | B1 | 4/2002 | Brace et al. |
| 6,514,258 | B1 | 2/2003 | Brown et al. |
| 6,716,215 | B1 | 4/2004 | David et al. |
| 6,887,244 | B1 | 5/2005 | Walker et al. |
| 6,913,463 | B2 | 7/2005 | Blacklock |
| 7,185,562 | B2 | 3/2007 | Raines, Jr. et al. |
| 7,195,485 | B2 | 3/2007 | Fischer |
| 7,278,852 | B2 | 10/2007 | Fischer |
| 7,441,480 | B2 | 10/2008 | Raines, Jr. et al. |
| 7,503,920 | B2 | 3/2009 | Siegal |
| 7,559,765 | B2 | 7/2009 | Courvoisier |
| 7,604,658 | B2 | 10/2009 | Wilson et al. |
| 7,625,378 | B2 | 12/2009 | Foley |
| 7,762,164 | B2 | 7/2010 | Nino et al. |
| 7,776,047 | B2 | 8/2010 | Fanger et al. |
| 7,833,230 | B2 | 11/2010 | Cerundolo |
| 7,909,829 | B2 | 3/2011 | Patel et al. |
| 7,909,848 | B2 | 3/2011 | Patel et al. |
| 7,935,123 | B2 | 5/2011 | Fanger et al. |
| 7,938,046 | B2 | 5/2011 | Nino et al. |
| 8,113,833 | B2 | 2/2012 | Courvoisier |
| 8,177,787 | B2 | 5/2012 | Walker et al. |
| 8,282,642 | B2 | 10/2012 | McClintock et al. |
| 8,337,499 | B2 | 12/2012 | Sasing et al. |
| 8,357,163 | B2 | 1/2013 | Sidebotham et al. |
| 8,394,107 | B2 | 3/2013 | Fanger et al. |
| 8,403,931 | B2 | 3/2013 | Sidebotham et al. |
| 8,439,947 | B2 | 5/2013 | Howard et al. |
| 8,444,652 | B2 | 5/2013 | Amis et al. |
| 8,449,545 | B2 | 5/2013 | Sidebotham et al. |
| 8,460,297 | B2 | 6/2013 | Watlington et al. |
| 8,518,043 | B2 | 8/2013 | Sidebotham et al. |
| 8,518,044 | B2 | 8/2013 | Sidebotham et al. |
| 8,523,866 | B2 | 9/2013 | Sidebotham et al. |
| 8,535,316 | B2 | 9/2013 | Lewis et al. |
| 8,540,716 | B2 | 9/2013 | Sidebotham et al. |
| 8,556,897 | B2 | 10/2013 | Sidebotham et al. |
| 8,597,301 | B2 | 12/2013 | Mitchell |
| 8,685,068 | B2 | 4/2014 | Sixto et al. |
| 8,911,474 | B2 | 12/2014 | Howard et al. |
| 8,945,135 | B2 | 2/2015 | Ries et al. |
| 8,986,354 | B2 | 3/2015 | Walker |
| 9,044,222 | B2 | 6/2015 | Dross |
| 9,162,350 | B2 | 10/2015 | Nino et al. |
| 9,226,744 | B2 | 1/2016 | Pilgeram |
| 9,282,975 | B2 | 3/2016 | Sweeney |
| 9,433,444 | B2 | 9/2016 | Humphreys et al. |
| 9,439,658 | B2 | 9/2016 | Ford et al. |
| 9,463,028 | B2 | 10/2016 | Sidebotham et al. |
| 9,510,841 | B2 | 12/2016 | Sweeney |
| 9,517,075 | B2 | 12/2016 | Sweeney |
| 9,574,952 | B2 | 2/2017 | Schintee |
| 9,700,327 | B2 | 7/2017 | Maxson |
| 9,717,491 | B2 | 8/2017 | Hoeppner |
| 9,757,171 | B2 | 9/2017 | Sixto et al. |
| 9,770,247 | B2 | 9/2017 | Courvoisier |
| 9,782,193 | B2 | 10/2017 | Thistle |
| 9,877,764 | B2 | 1/2018 | Nino et al. |
| 9,925,068 | B2 | 3/2018 | Bays et al. |
| 9,943,948 | B2 | 4/2018 | Nino et al. |
| 9,955,980 | B2 | 5/2018 | Norton et al. |
| 9,962,167 | B2 | 5/2018 | Stephane |
| 10,118,233 | B2 | 11/2018 | Gruhn et al. |
| 10,172,703 | B2 | 1/2019 | Adams et al. |
| 10,206,692 | B2 | 2/2019 | Sanders |
| 10,219,853 | B2 | 3/2019 | Nino et al. |
| 10,342,678 | B2 | 7/2019 | Flores et al. |
| 10,383,640 | B2 | 8/2019 | Houssiere et al. |
| 2002/0165549 | A1 | 11/2002 | Owusu-Akyaw et al. |
| 2005/0015093 | A1 * | 1/2005 | Suh ................... A61B 17/8057 606/96 |
| 2006/0111723 | A1 | 5/2006 | Chapolini et al. |
| 2008/0039873 | A1 | 2/2008 | Bonutti et al. |
| 2008/0086142 | A1 | 4/2008 | Kohm et al. |
| 2009/0030338 | A1 | 1/2009 | Crocker et al. |
| 2009/0075233 | A1 | 3/2009 | Zhang |
| 2009/0326562 | A1 | 12/2009 | White et al. |
| 2010/0082046 | A1 | 4/2010 | Harris et al. |
| 2010/0094314 | A1 | 4/2010 | Hernlund et al. |
| 2010/0137872 | A1 | 6/2010 | Kam et al. |
| 2011/0177473 | A1 | 7/2011 | Darwish et al. |
| 2012/0191094 | A1 * | 7/2012 | Alain ................. A61B 17/1671 606/80 |
| 2012/0209278 | A1 * | 8/2012 | Ries ..................... A61B 17/158 606/96 |
| 2012/0245586 | A1 * | 9/2012 | Lehenkari ............... A61B 6/145 606/80 |
| 2013/0123809 | A1 | 5/2013 | Murphy et al. |
| 2013/0123810 | A1 | 5/2013 | Brown et al. |
| 2014/0081281 | A1 | 3/2014 | Felder |
| 2014/0107672 | A1 | 4/2014 | Dross |
| 2015/0173805 | A1 * | 6/2015 | Donner .................. A61B 17/68 606/279 |
| 2015/0196363 | A1 | 7/2015 | Aman et al. |
| 2016/0015379 | A1 | 1/2016 | Keller et al. |
| 2016/0030056 | A1 | 2/2016 | Ahuja et al. |
| 2016/0045206 | A9 | 2/2016 | Stephane |
| 2016/0166350 | A1 | 6/2016 | Burkhardt et al. |
| 2016/0270800 | A1 * | 9/2016 | Sanders ................. A61B 17/17 |
| 2017/0043415 | A1 * | 2/2017 | Cheney ................. B23B 49/023 |
| 2018/0296244 | A1 * | 10/2018 | Kim .................... A61B 17/1725 |
| 2019/0183516 | A1 * | 6/2019 | Peterson ............ A61B 17/1757 |

FOREIGN PATENT DOCUMENTS

| | | | |
|---|---|---|---|
| EP | 2730232 | A1 | 5/2014 |
| FR | 2750031 | A1 | 12/1997 |

OTHER PUBLICATIONS

AU Exam Report, App. No. 2021202655, dated Jun. 3, 2022, pp. 1-6.

* cited by examiner

MULTI-BARREL DRILL GUIDE AND ANCHOR DEPLOYMENT ASSEMBLY

CROSS-REFERENCE TO RELATED APPLICATION

The present application claims priority to and the benefit of U.S. Provisional Patent Application No. 62/515,033, filed on Jun. 5, 2017, U.S. Provisional Patent Application No. 62/515,082, filed on Jun. 5, 2017, U.S. Provisional Patent Application No. 62/516,733, filed on Jun. 8, 2017, U.S. Provisional Patent Application No. 62/618,817, filed on Jan. 18, 2018, and U.S. Provisional Patent Application No. 62/649,181, filed on Mar. 28, 2018.

BACKGROUND OF THE INVENTION

1. Field of the Invention

The present invention relates to drills, anchor drivers, and a drill guide for drilling a pilot hole at a surgical repair site and inserting a suture anchor in the pilot hole and, more particularly, to a multi-barrel drill guide and anchor deployment assembly for both drilling a pilot hole at a surgical repair site and inserting a suture anchor into the pilot hole while maintaining alignment of the drill guide with the pilot hole.

2. Description of Related Art

Many orthopedic surgical and medical procedures require the fixation of one body to another body. Such bodies may include bone, soft tissue, and prosthetics. One body can be fixed in a position relative to another using connector devices, such as screws and suture anchors (e.g., cannulated knotless suture anchors and soft all suture anchors). For example, various orthopedic surgeries require the insertion and fixation of a suture anchor within a bone. In such surgeries, prior to insertion of a suture anchor, a pilot hole is drilled into the bone. Traditionally, a standard single barrel drill guide is placed at the desired pilot hole location on the bone and a drill is placed through the drill guide to create the pilot hole. The drill is then removed and replaced with a driver pre-loaded with the suture anchor. Thus, a surgeon must completely remove the drill from the drill guide and insert the driver all while maintaining alignment of the drill guide with the pilot hole. Exchanging tools within the drill guide after creation of the pilot hole increases the risk that the alignment of the drill guide with the pilot hole will be lost. A loss of alignment requires additional surgical time to correct the misalignment, if even possible, and may potentially result in trauma to the tissue or bone surrounding the pilot hole. Loss of alignment can also result in the anchor inserter rod bending or the anchor not being able to insert fully into the pilot hole which can add cost as well as surgical time. To avoid misalignment with a standard single barrel guide, an additional assistant may be required to help maintain alignment or attempt realignment.

In addition, traditional suture anchors deployed by conventional drivers are often too large for procedures that involve soft tissue fixation in the extremities. A bone hole drilled in an extremity must be shallow and have a narrow diameter due to the very nature of the location of the procedure. A shallow bone hole requires that the anchor have exceptional retention capacity, because any movement of the anchor away from the shallow bone hole might entirely release the anchor from the bone hole. At the very least, the anchor may extend out of the shallow and narrow bone hole. Ill-fitting suture anchors have increased instability and can cause irritation or damage to tissue surrounding the exposed portion of the anchor.

Attempts at addressing the problem include scaling down the size of a traditional suture anchor to fit within a shallow and narrow bone hole. However, as the size of the traditional suture anchor decreases, the anchor loses retention capacity and thus is unstable within the bone hole. Although numerous factors can influence the retention capacity of a suture anchor, such as the type of tissue, the size of the bone hole, and the anchor's design, the method of deployment of the suture anchor can also influence a suture anchor's retention capacity.

Therefore, there is a need for an assembly requiring minimal movement and surgical time for drilling a pilot hole, and inserting and deploying a suture anchor with reliable retention capacity.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with the conventional single barrel drill guide (as discussed herein and above). For example, removing a drill bit from the drill guide and replacing it with a driver to insert the suture anchor increases the risk of misalignment of the drill guide with the pilot hole, which requires additional surgical time and risks trauma to the surrounding tissue and bone. Therefore, a need exists for a simple to use multi-barrel drill guide and anchor deployment assembly that is configured to simultaneously accommodate both a drill bit and a driver with a suture anchor. Such a structural configuration allows for the suture anchor to be in position with the anchor driver in a separate but converging pathway/channel in the drill guide and ready for insertion into a pilot hole immediately after the pilot hole is formed by the drill bit. This can be done without having to pull the drill bit out of the drill guide prior to being able to insert the suture anchor driver into the post-convergent area of the drill guide. Various embodiments of the present invention may be advantageous in that they may solve or reduce one or more of the potential problems and/or disadvantages discussed herein.

The present disclosure is directed to an inventive configuration, structure, and resulting function of a multi-barrel drill guide and anchor deployment assembly. The multi-barrel drill guide and anchor deployment assembly includes an elongated body extending along a longitudinal axis having a proximal end and a distal end with a handle extending from the elongated body at an angle from the longitudinal axis (at an acute angle or orthogonal from the longitudinal axis) at a position between the proximal end and the distal end. The assembly also includes an elongated distal guide tube attached to and extending from the distal end of the elongated body. A sliding inserter is movably connected to the elongated body such that the sliding inserter is configured to move between the proximal end and the distal end of the elongated body. The assembly also has a first channel, which extends from the proximal end to the distal end, and a second channel which extends from the distal end to a position between the distal end and the proximal end along the elongated body. The second channel extends at an angle relative to the first channel. The first channel and the second channel intersect at a convergence area at the distal end. In an embodiment, the convergence area extends to a single exit point. In another embodiment, the single exit point is at a distal end of the elongated distal guide tube.

The multi-barrel drill guide and anchor deployment assembly is configured to accommodate a suture anchor and driver movable in a slidable manner within the first channel and connected to the sliding inserter, and a drill bit movable in a slidable manner within the second channel. In an embodiment, the second channel curves in a direction away from the handle. In another embodiment, a portion (or bent portion) of the second channel extends at an angle relative to the longitudinal axis that is different from the remainder of the second channel. In accordance with an embodiment, the elongated body has an optional slot/slit for a filament (or suture) connected to the anchor positioned through the outside surface of the elongated body (and preferably into the first channel). In another embodiment, the assembly includes a locking mechanism configured to selectively lock the sliding inserter in place with respect to the elongated body. In an embodiment, the locking mechanism includes an opening in the sliding inserter selectively aligned with an opening in the elongated body, which extends to the second channel. In a locked position, the drill bit extends through the opening of the sliding inserter and the opening in the elongated body into the second channel.

In another embodiment of the assembly, the elongated body includes a recess and a shallow deployment button hingedly connected within the recess. In an embodiment, the driver is connected to the sliding inserter and sliding the driver distally along the first channel rotates the shallow deployment button from the recess.

According to an another aspect, a method of drilling a pilot hole and inserting a suture anchor in the pilot hole includes, but is not limited to, the steps of: (i) providing a multi-barrel drill guide and anchor deployment assembly with an elongated body extending along a longitudinal axis having a proximal end and a distal end, a handle extending from the elongated body at an angle from the longitudinal axis (at an acute angle or orthogonal from the longitudinal axis) at a position between the proximal end and the distal end, and an elongated distal guide tube attached to and extending distally from the distal end of the elongated body, a sliding inserter movably connected to the elongated body such that the sliding inserter is configured to move between the proximal end and the distal end of the elongated body, a first channel extending from the proximal end to the distal end, a second channel extending from the distal end to a position between the distal end and the proximal end along the elongated body, the second channel at an angle relative to the first channel, and a convergence area at the distal end where the first channel and the second channel intersect; (ii) inserting a suture anchor loaded on an anchor driver into the first channel; (iii) inserting a drill bit into an opening on the sliding inserter and an opening on elongated body, which extends into the second channel; (iv) positioning a distal end of the distal guide tube against a bone; (v) extending the drill bit through the second channel, the convergence area and the distal guide tube; (vi) drilling a pilot hole into the bone with the drill bit; (vii) retracting the drill bit past the opening on the sliding inserter; (viii) extending the anchor driver through the first channel and the convergence area; (ix) implanting the suture anchor into the pilot hole. The above referenced method can be performed with the drill bit being positioned within the first channel and the driver with the suture anchor being positioned within the second channel.

Suture material or sutures, as the terms are used and described herein, can include monofilament or multi-filament suture as well as any other metallic or non-metallic filamentary or wire-like material suitable for performing the function of a suture. This material can include both bioabsorbable and non-absorbable materials.

Suture anchors, as the term is used herein, can include soft suture anchors and rigid suture anchors. Soft suture anchors are formed from filaments of suture material which are retained within pre-formed bone holes by being deformable to increase their diameter to a size greater than that of the bone hole, to thereby reside within the cancellous bone and under the bone cortex. One such suture anchor is disclosed in U.S. Pat. No. 9,826,971 assigned to the assignee hereof and incorporated by reference herein in its entirety. Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. Methods and devices for inserting/deploying such all-suture anchors are known, examples of which are disclosed in U.S. Pat. No. 9,173,652.

As described in U.S. Pat. No. 8,409,252, for example, "non-soft," "hard" or "rigid" suture anchors generally include a "hard" anchor body portion (that may or may not include inner and outer members) and a suture/filament portion. The anchor body of such suture anchors may be formed of a biocompatible and/or bioabsorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-tricalcium phosphate ("PLA/Beta-TCP") composites, ultra-high molecular weight polyethylene ("UHMWPE"), as well as other metallic, non-metallic, and polymeric materials.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

Figure 29:
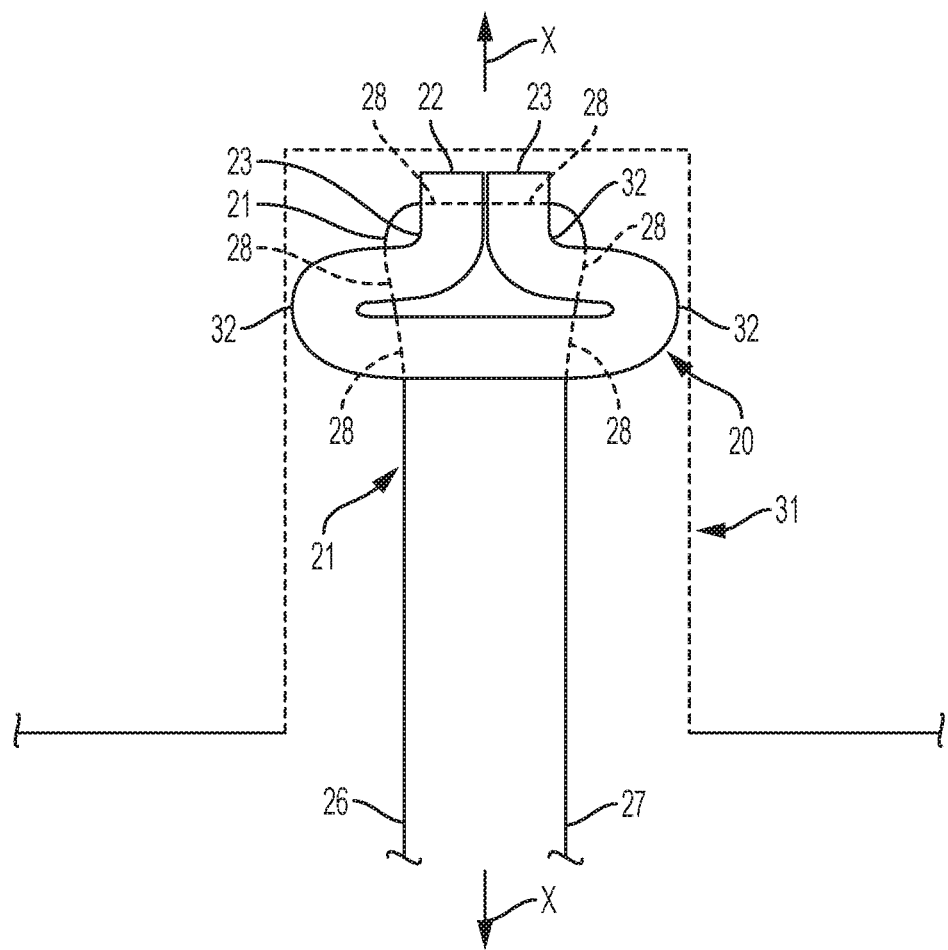
FIG. 29 is a side view schematic representation of the suture anchor of FIG. 22 in the fully deployed configuration according to an embodiment.
Figure 29A:
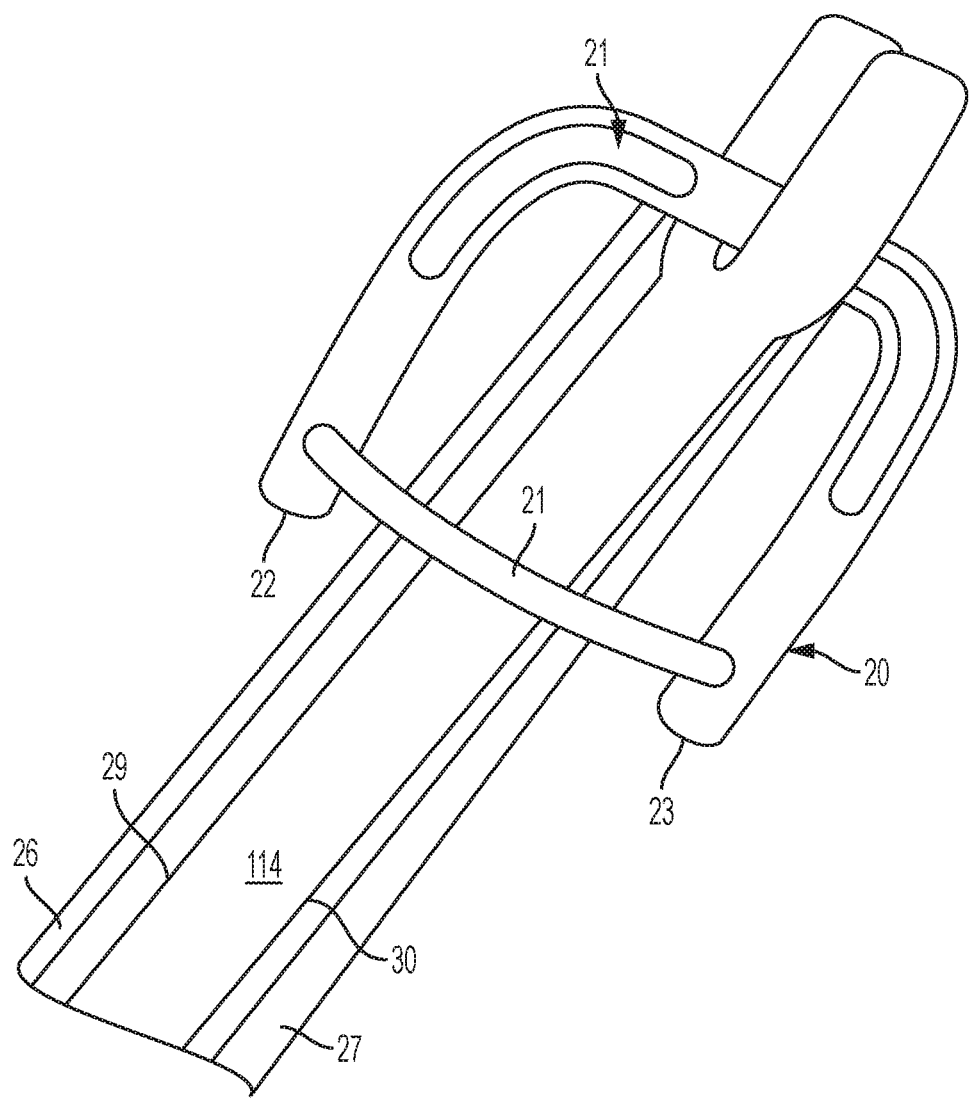
FIG. 29A is a side view schematic representation of a suture anchor loaded onto the anchor driver according to an alternative embodiment.
Figure 29B:
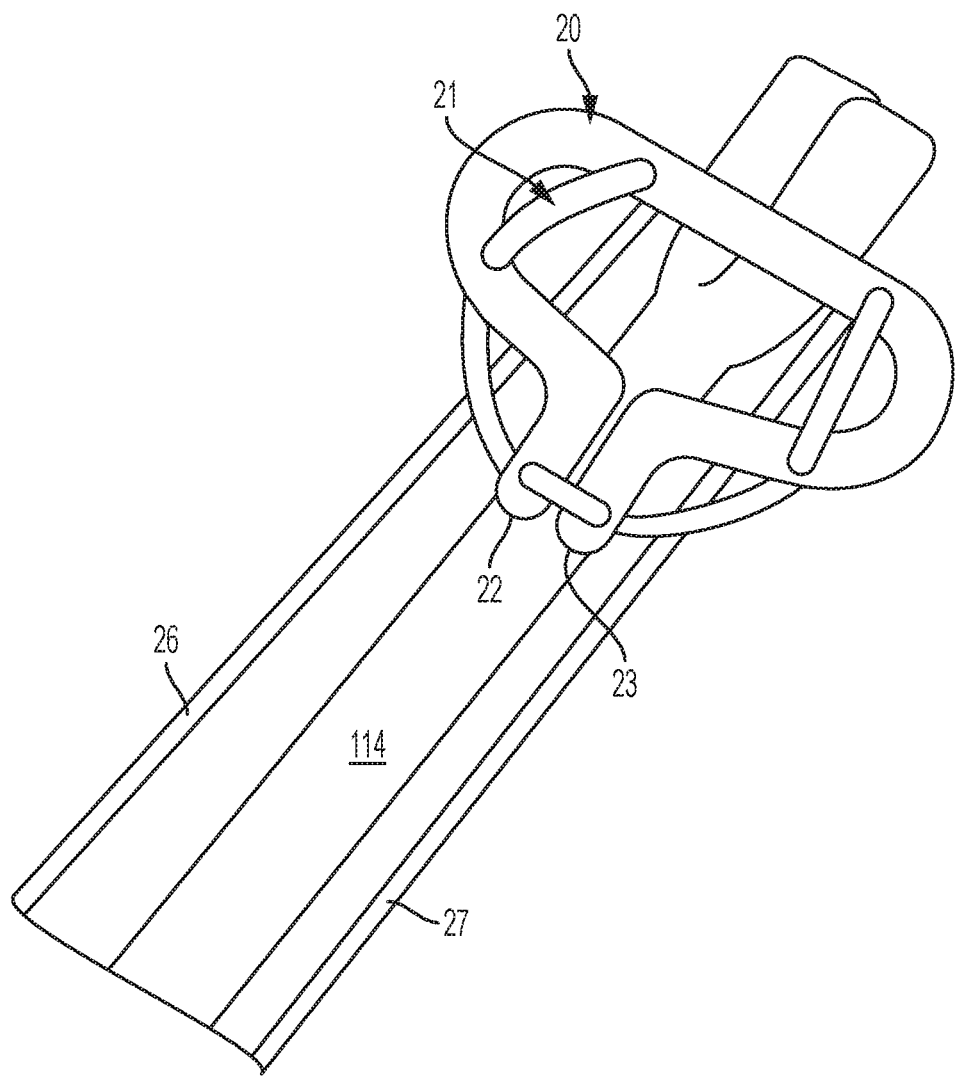
FIG. 29B is a side view schematic representation of the suture anchor of FIG. 29A loaded onto the anchor driver in the partially deployed configuration according to an alternative embodiment.
Figure 29C:
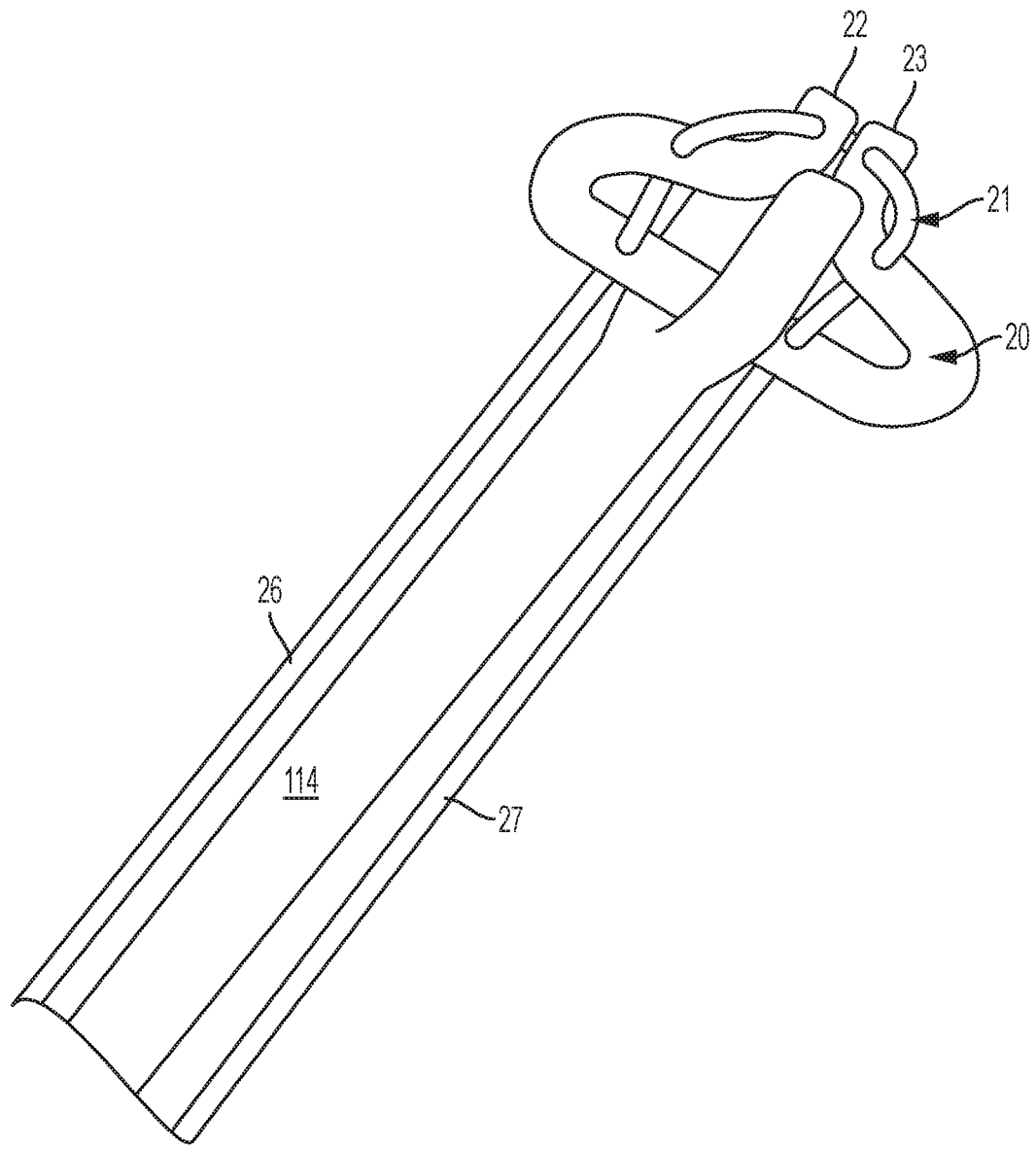
Figure 30:
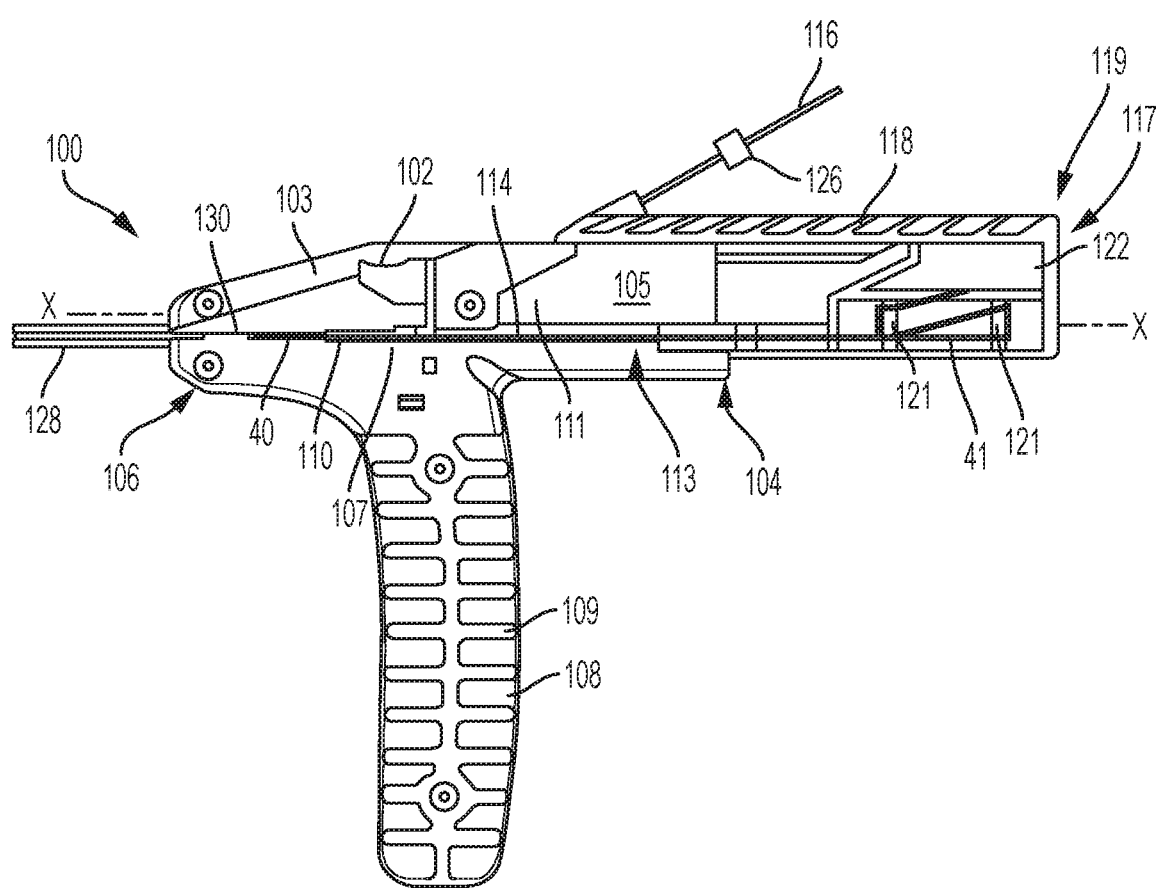
Figure 31:
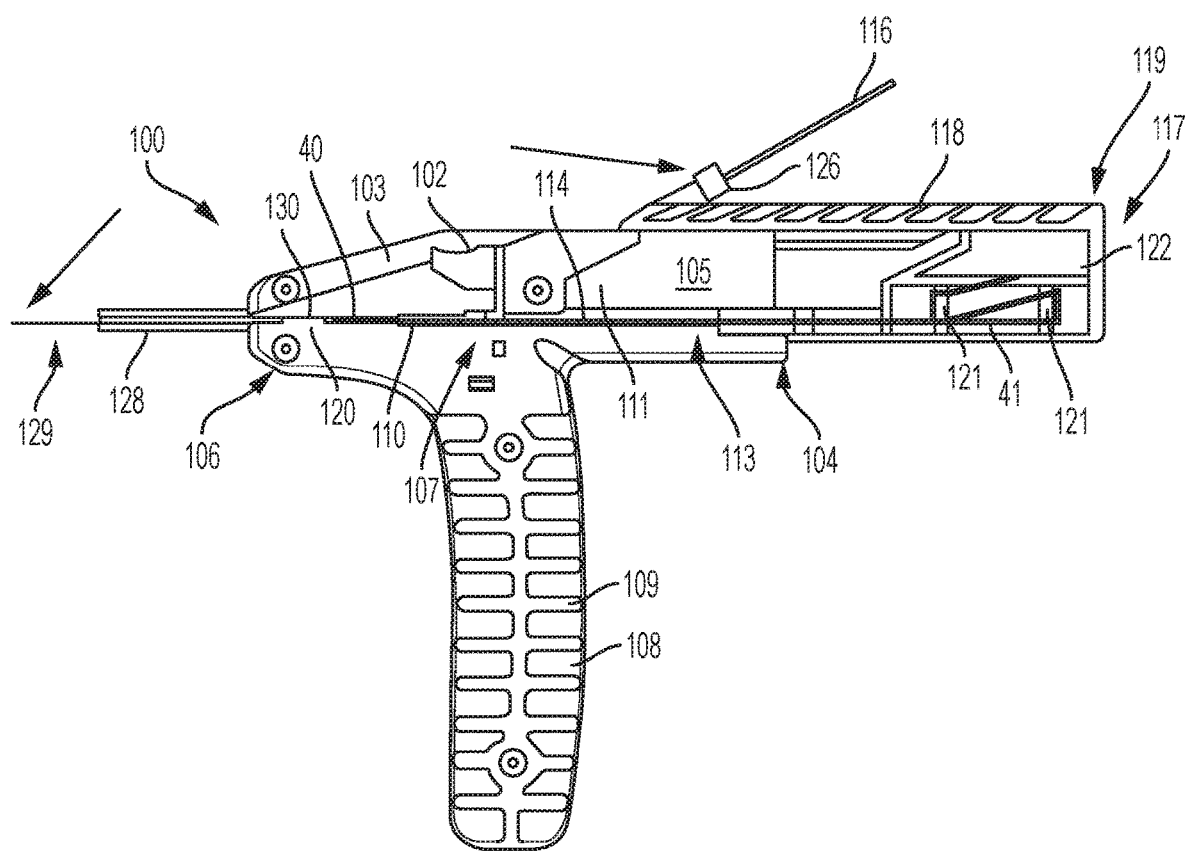
Figure 32:
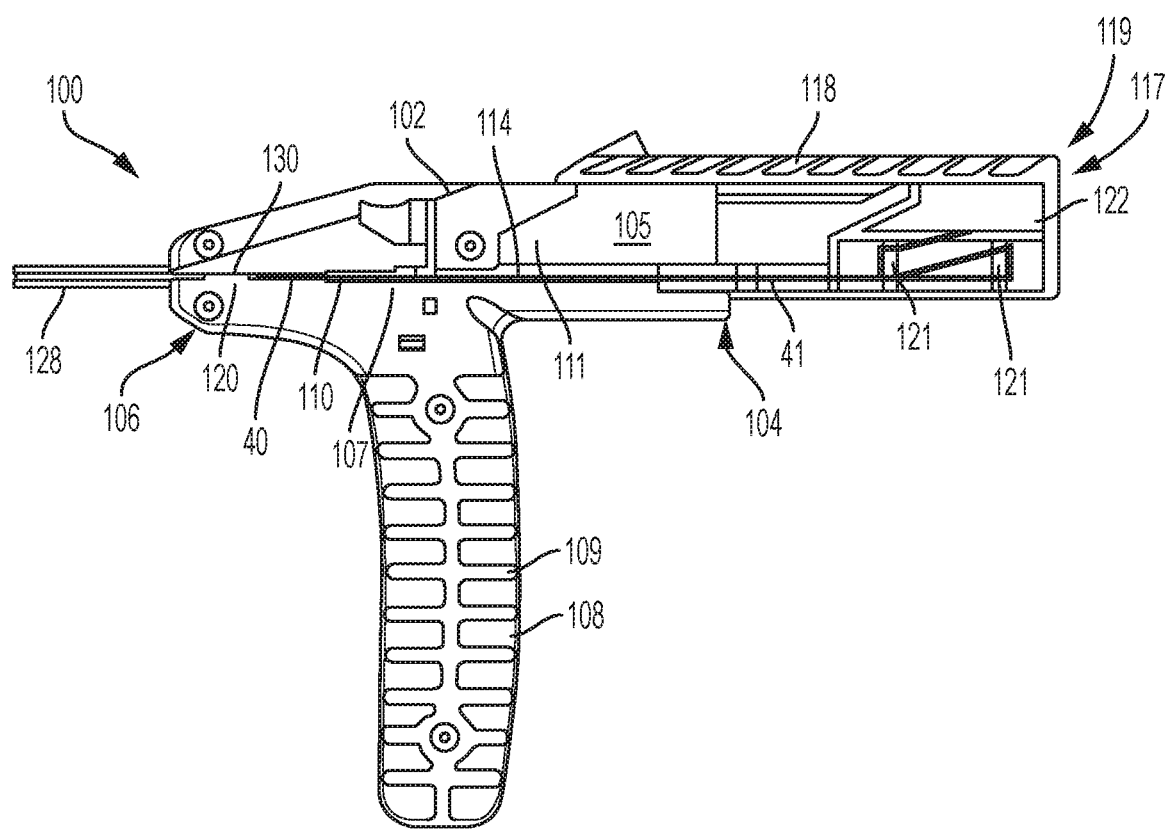
Figure 33:
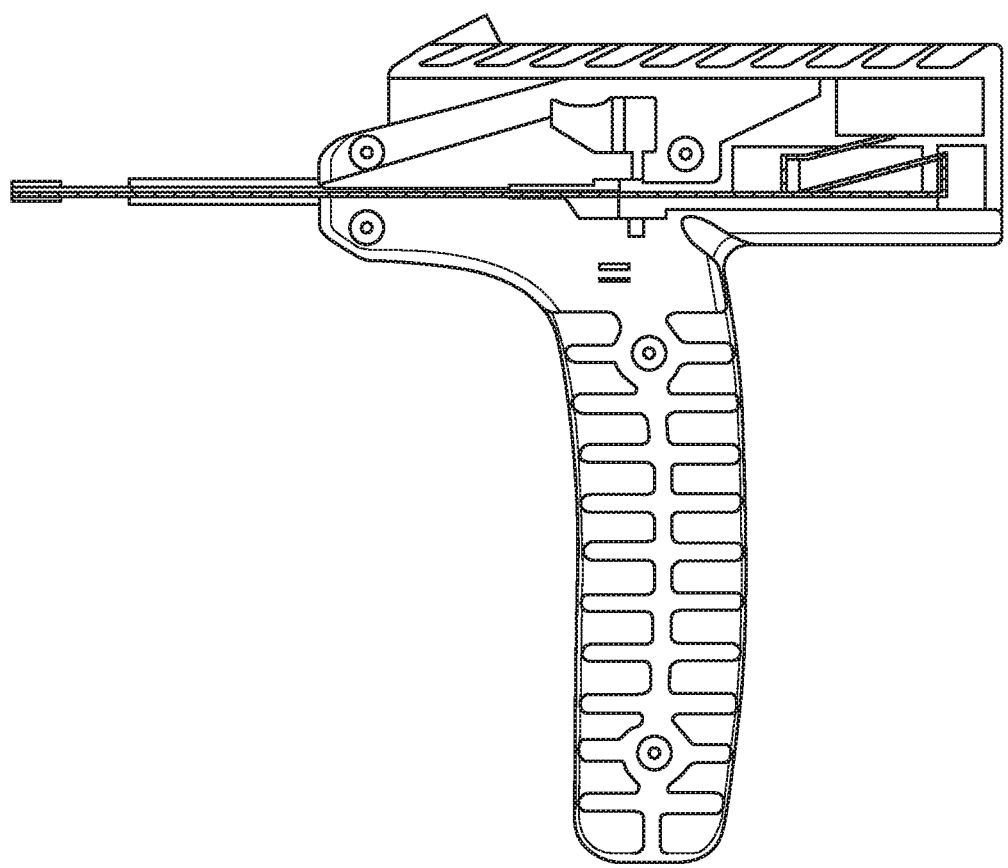
Figure 34:
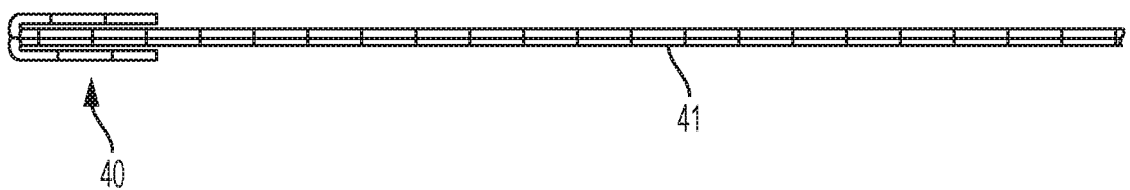
Figure 35:
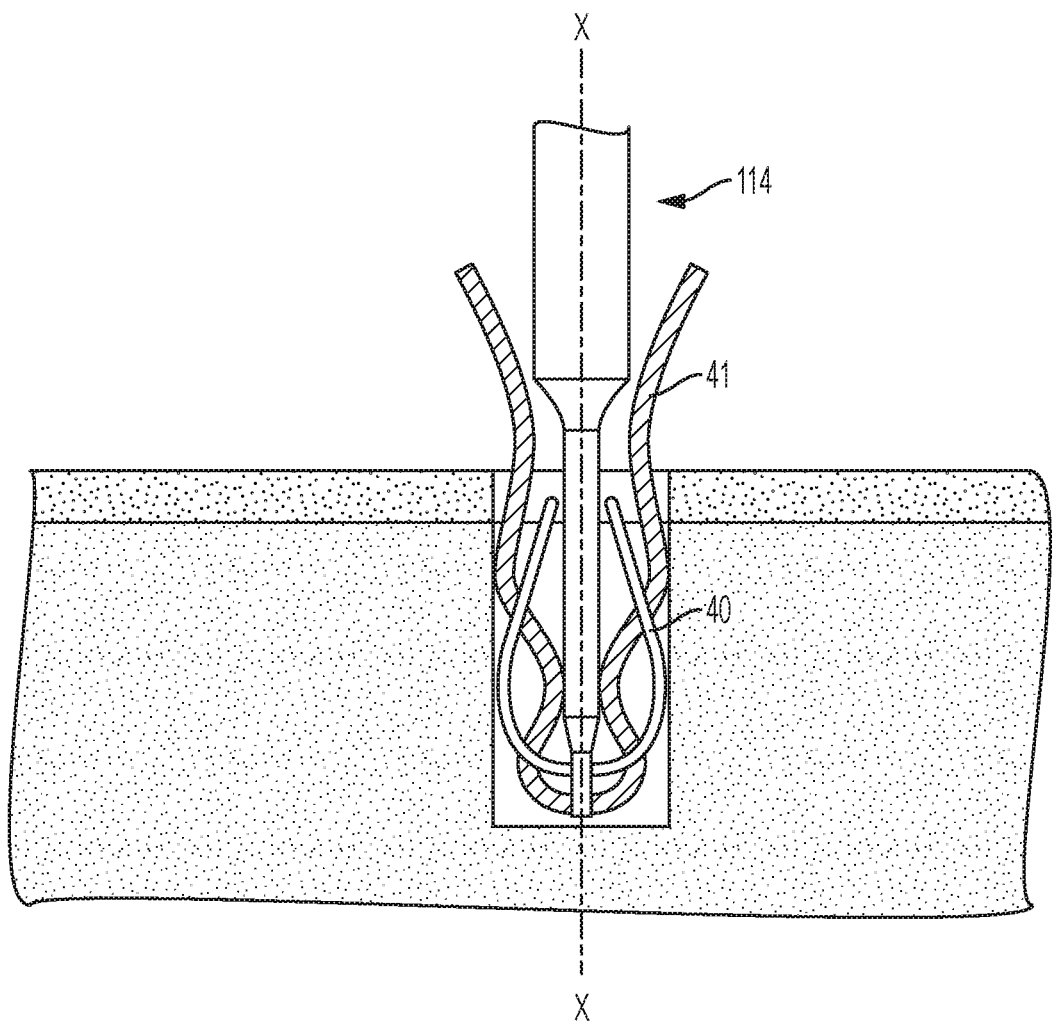
Figure 36:
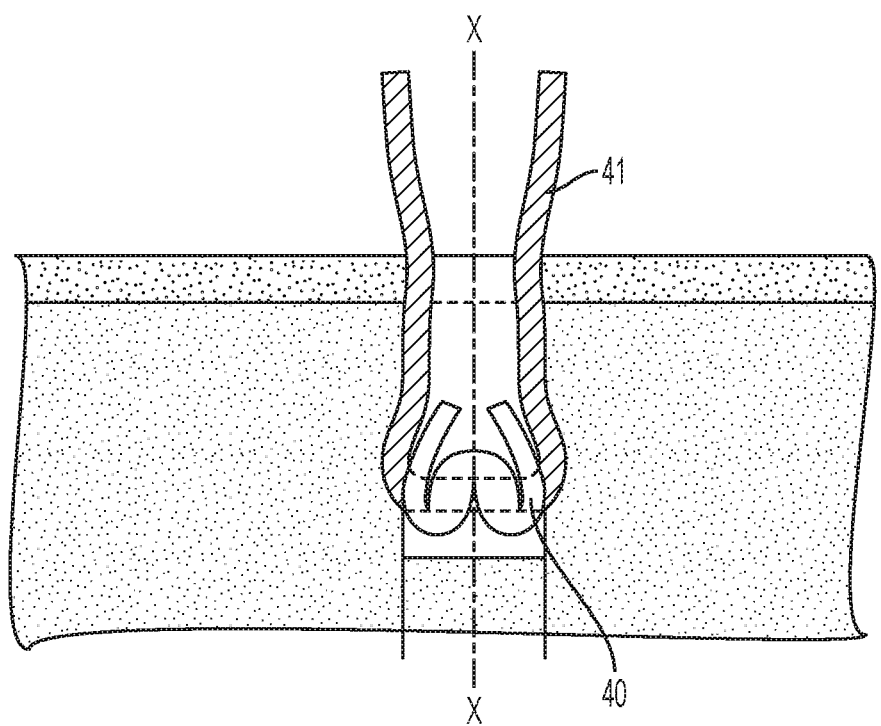
Figure 37:
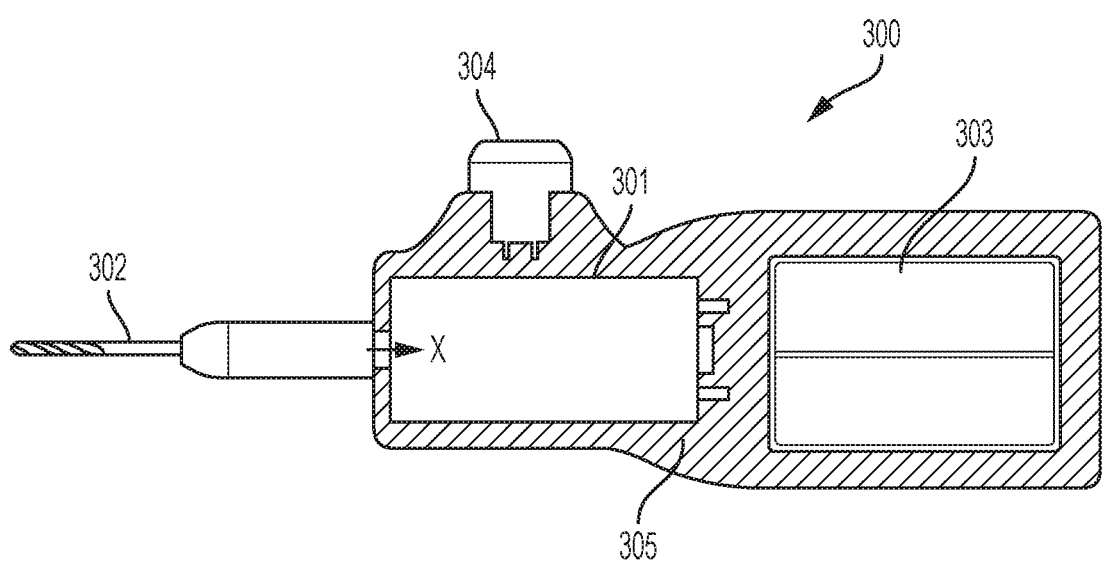
Figure 38:
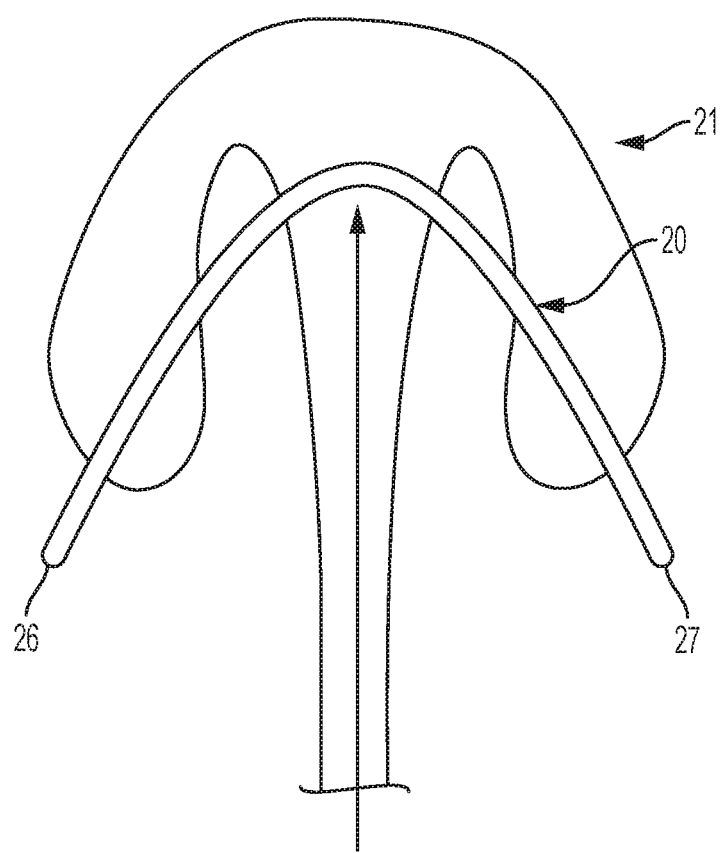
Figure 39:
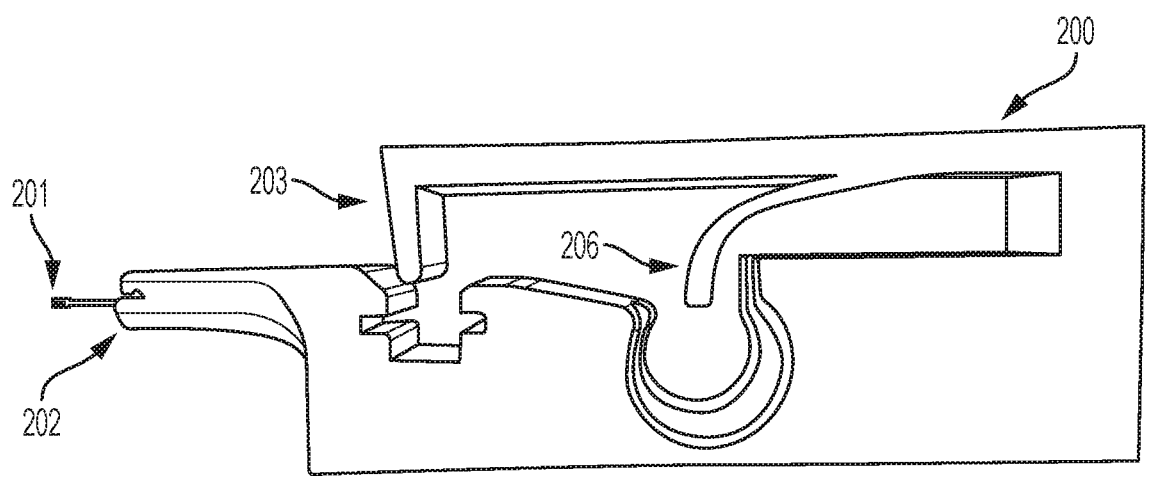
Figure 40:
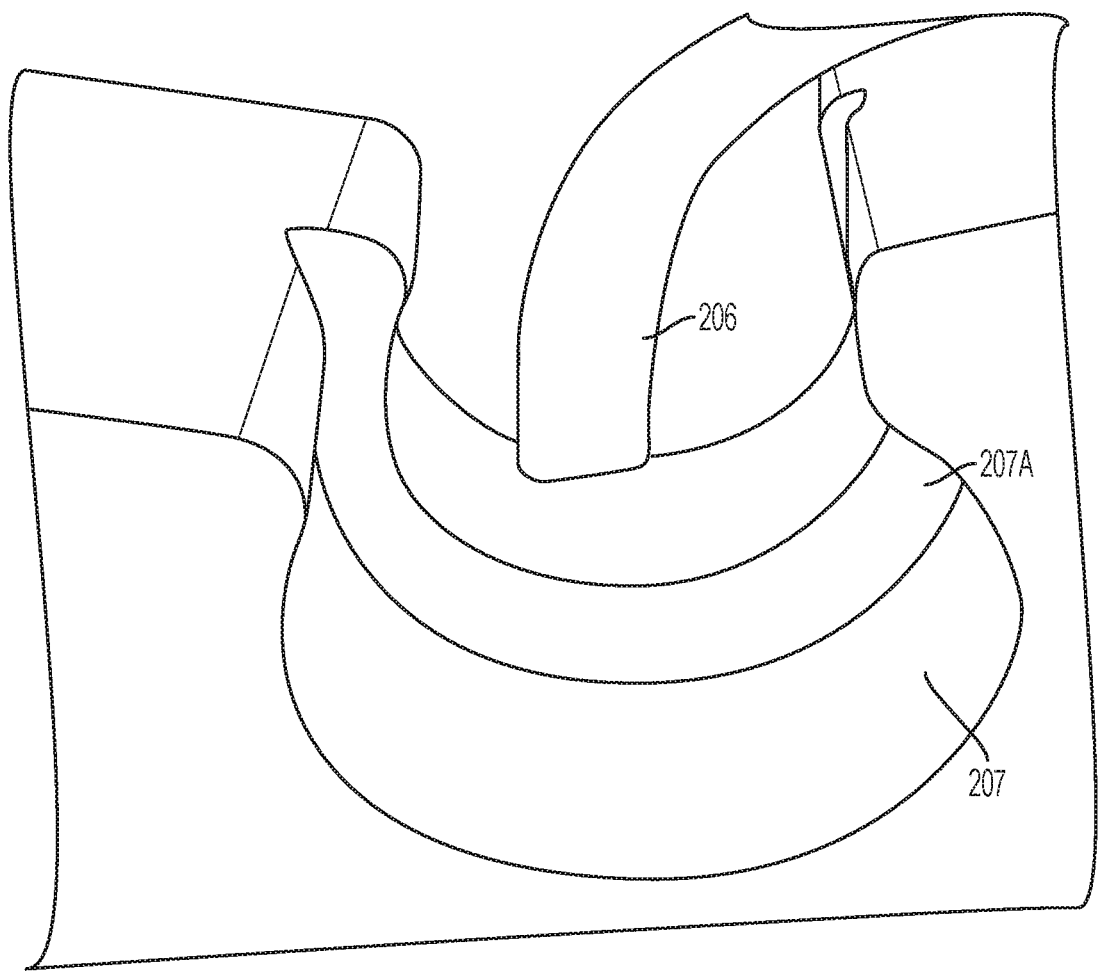
Figure 41:
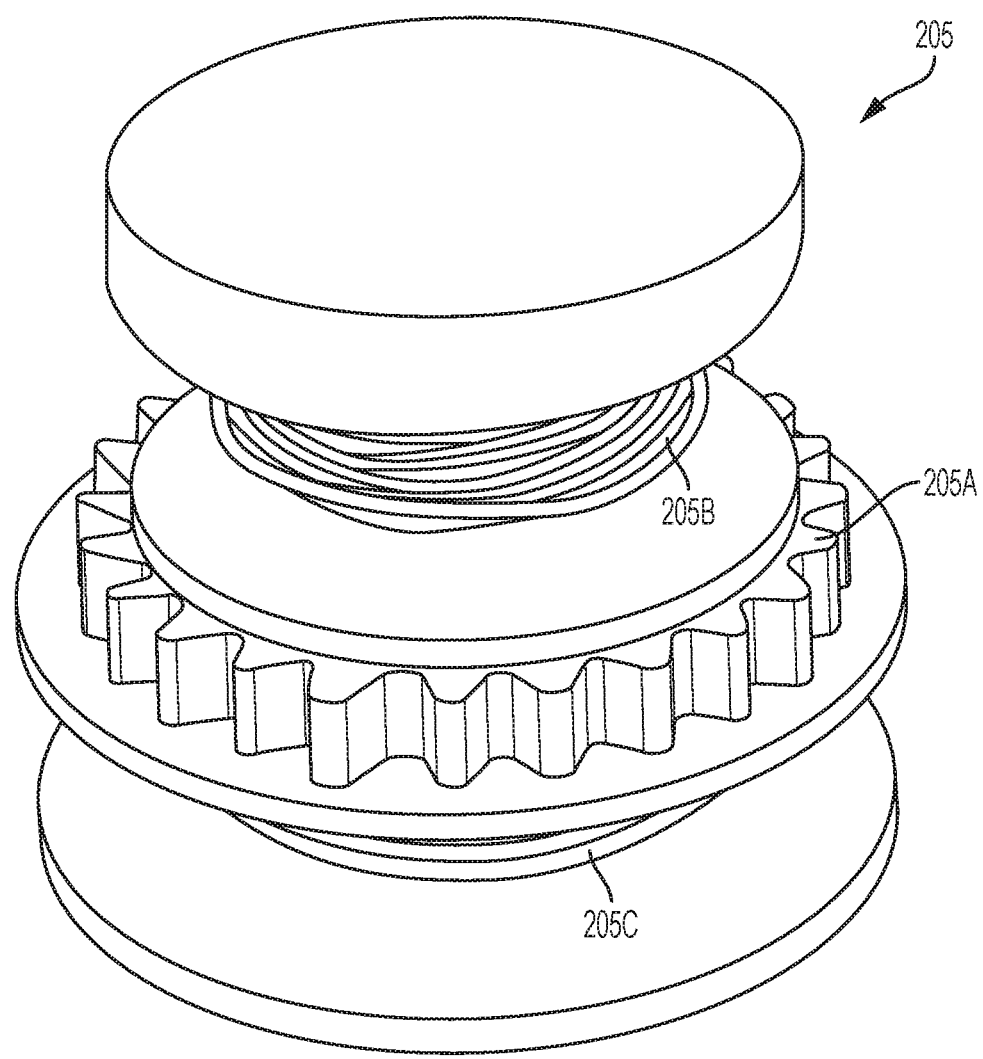
Figure 42:
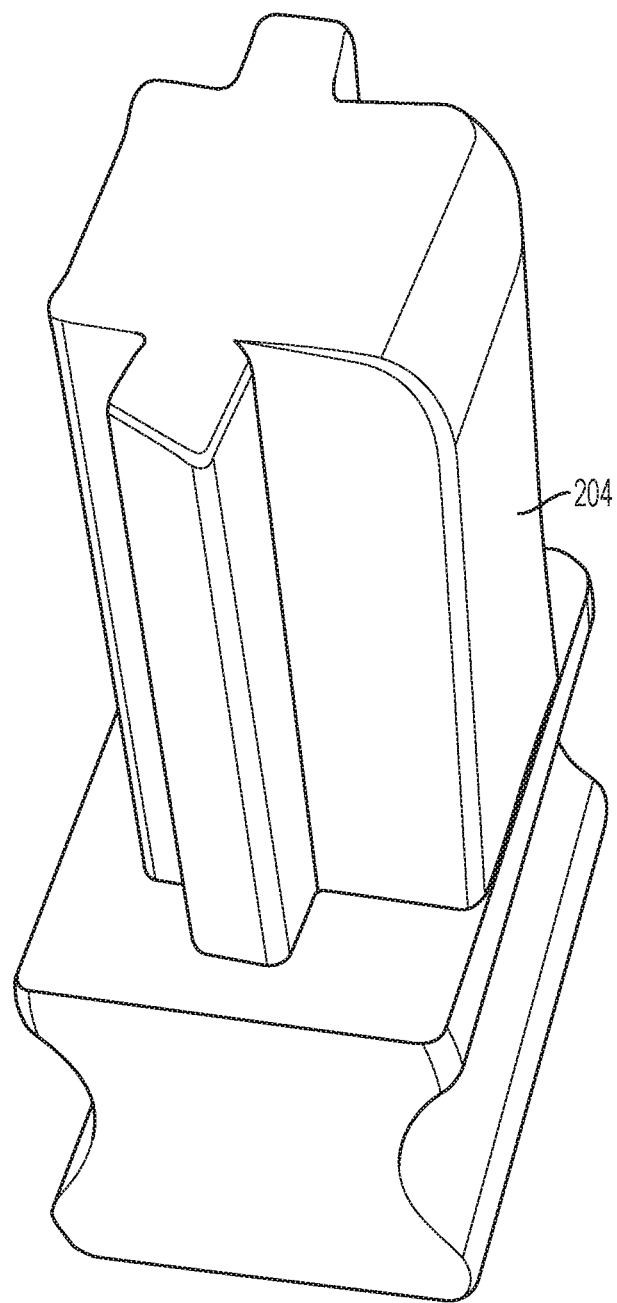
Figure 43:
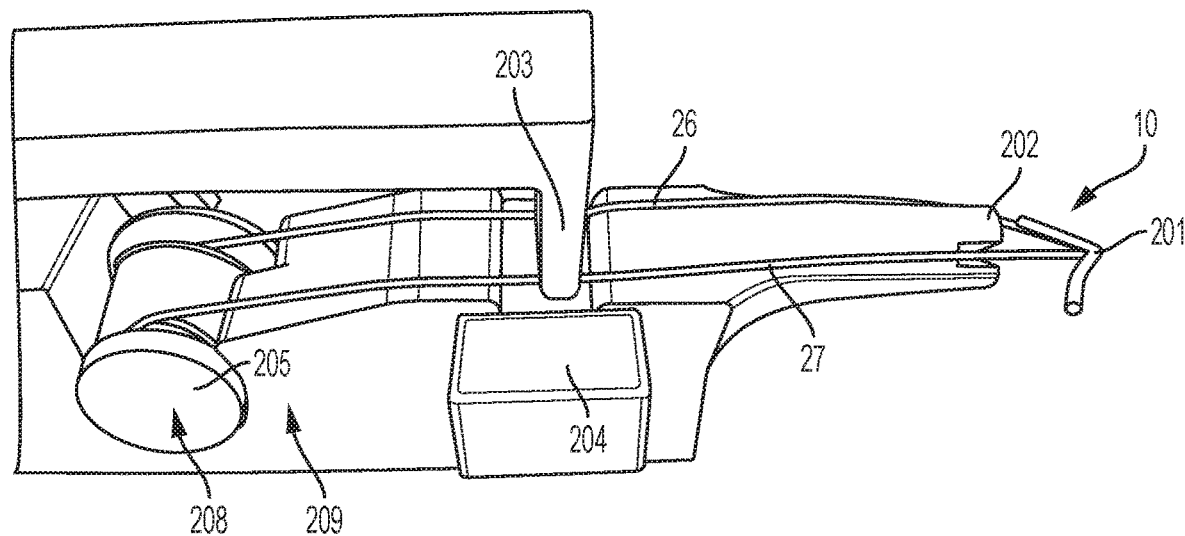
Figure 44:
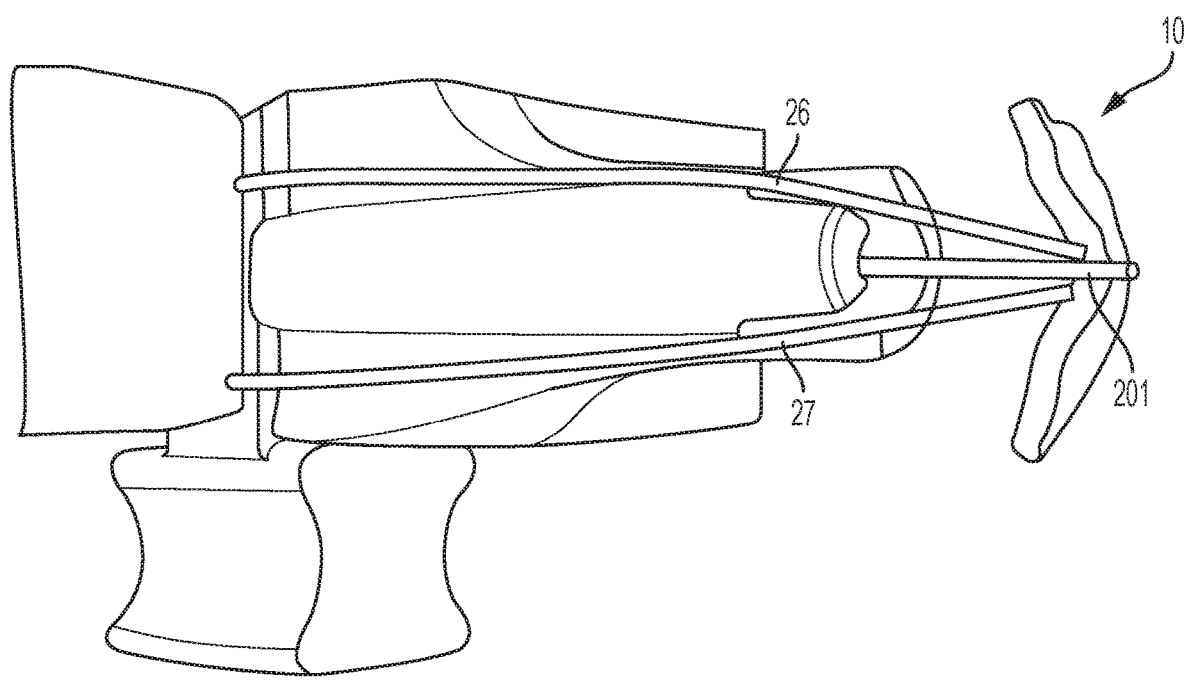
Figure 45:
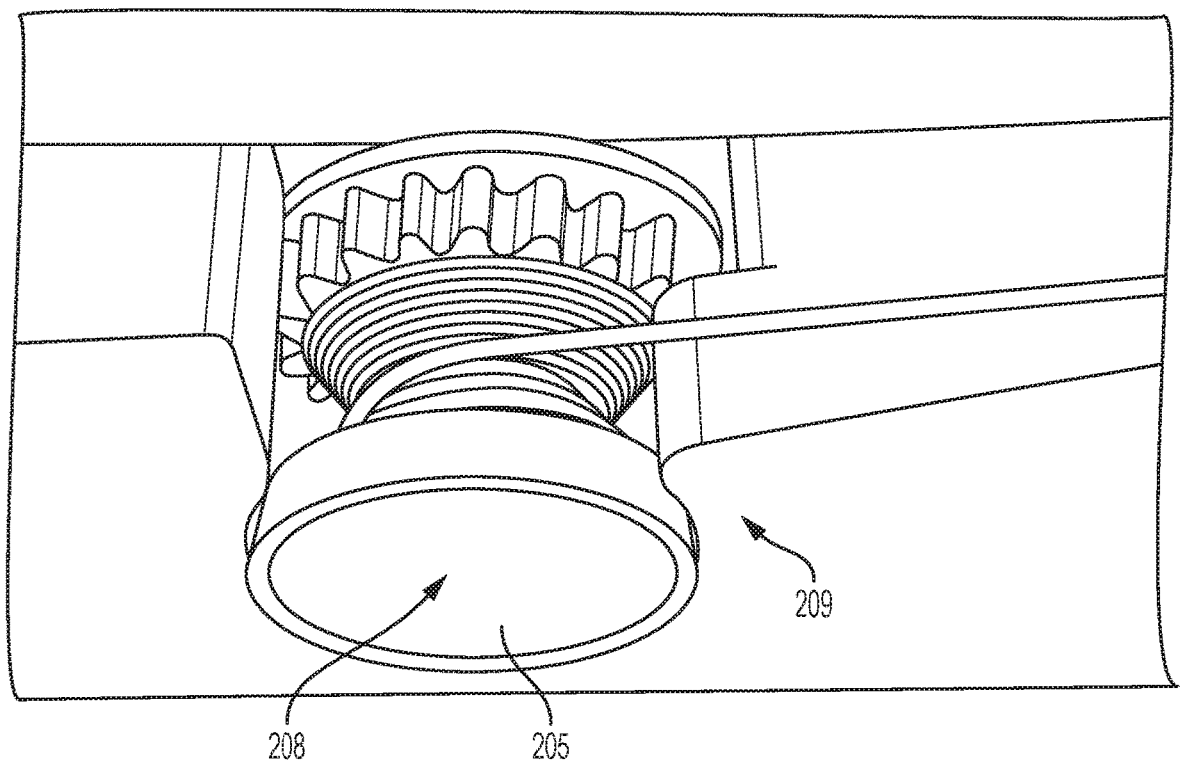
Figure 46:
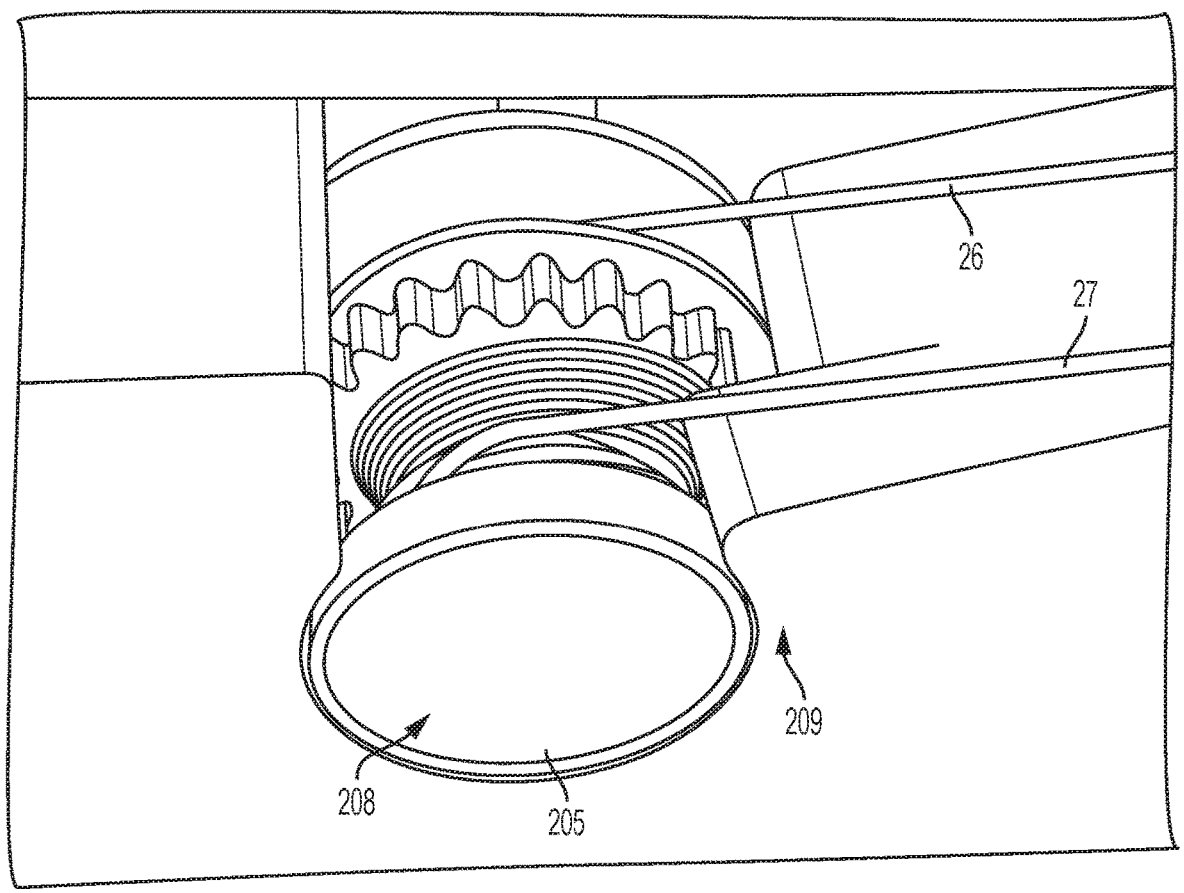
Figure 47:
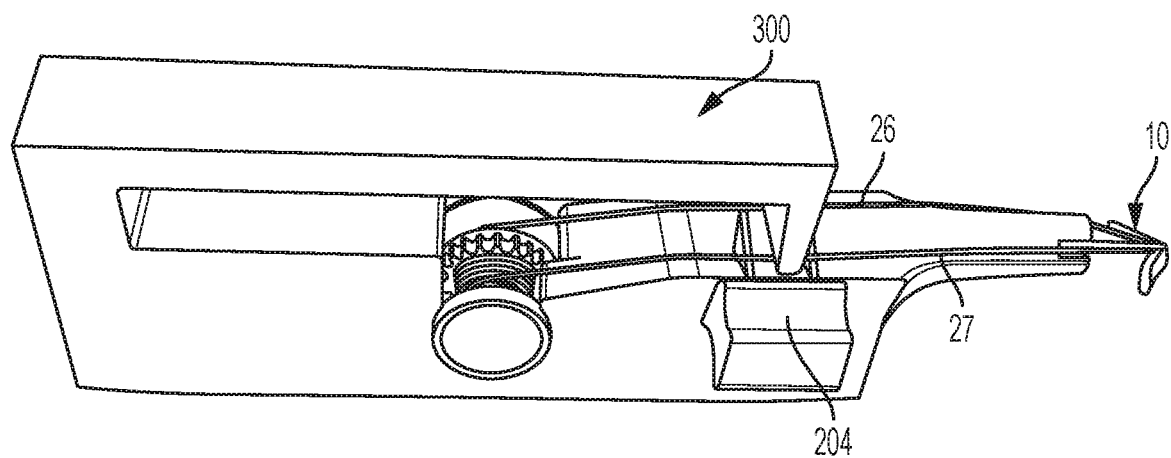
Figure 48:
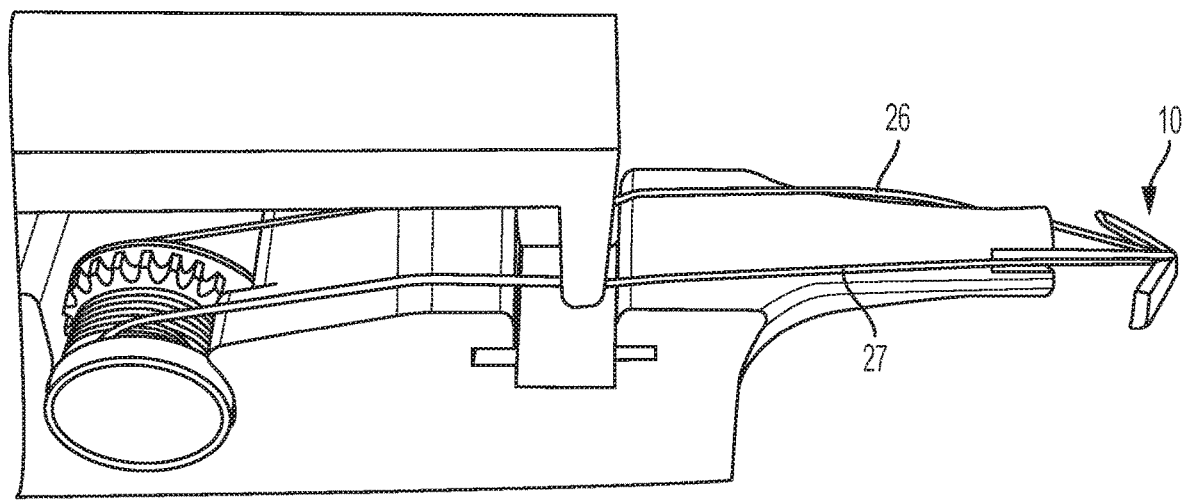
Figure 49:
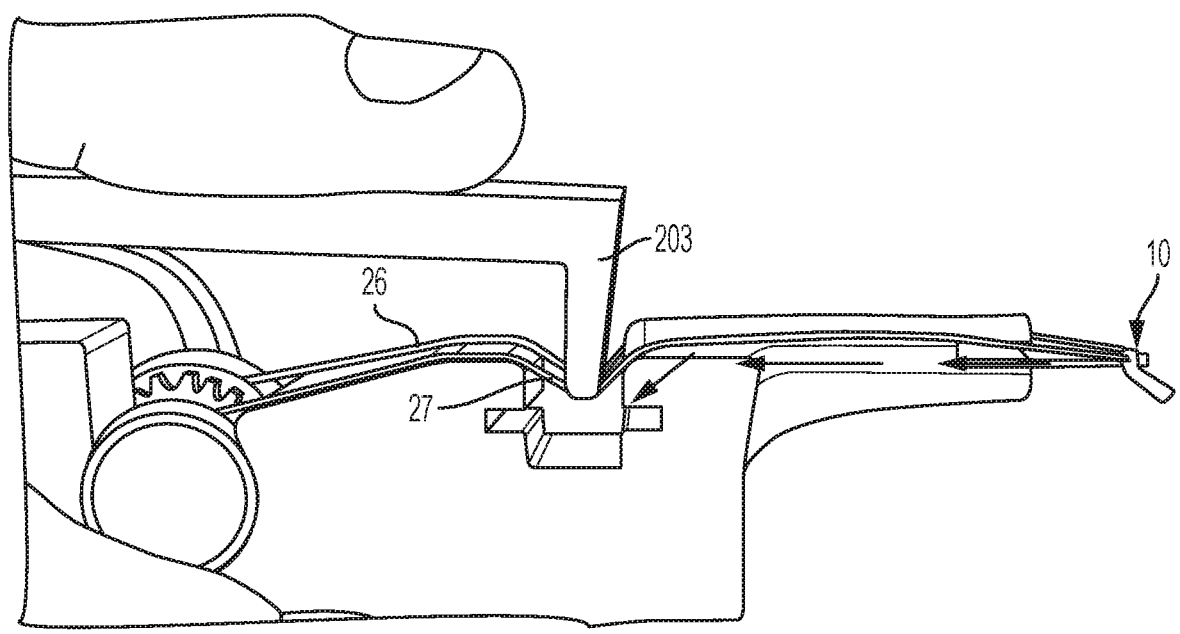
Figure 50:
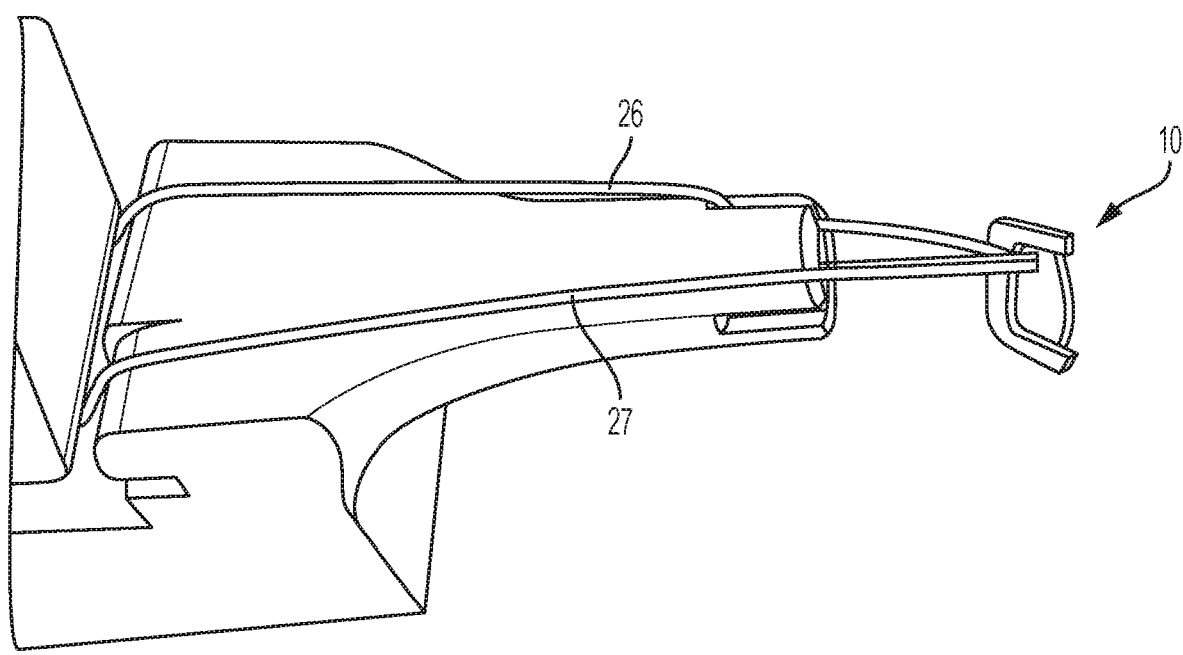
Figure 51:
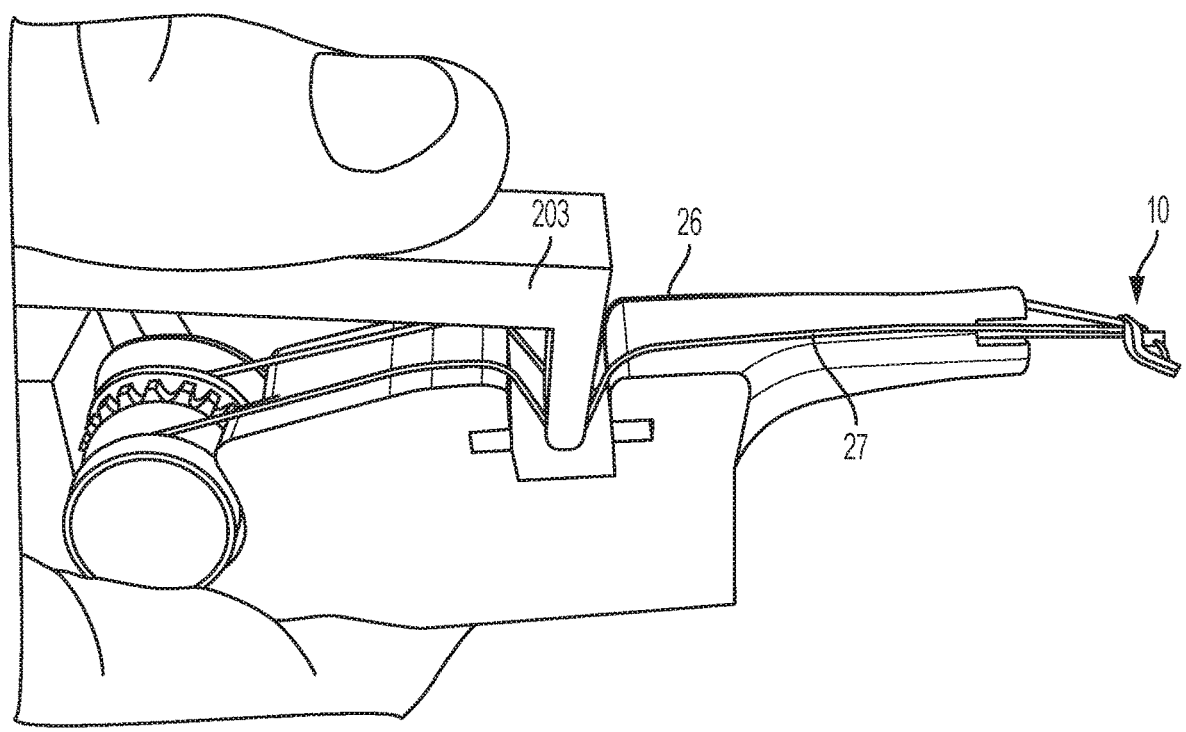
Figure 52:
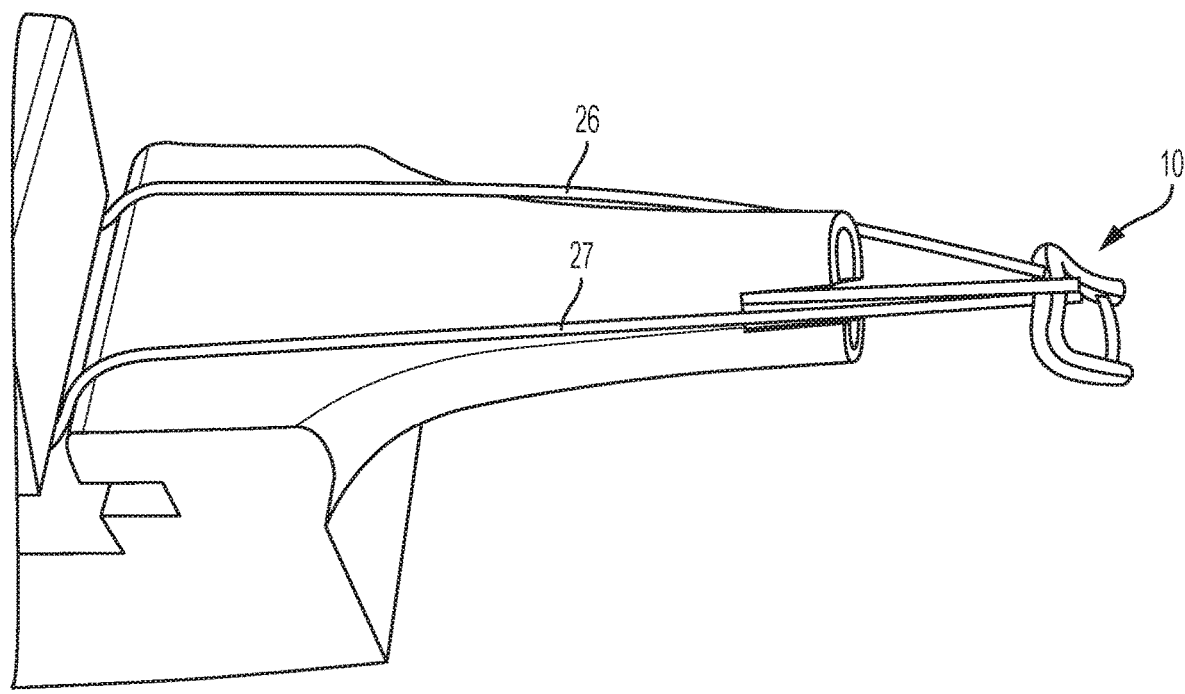
Figure 53:
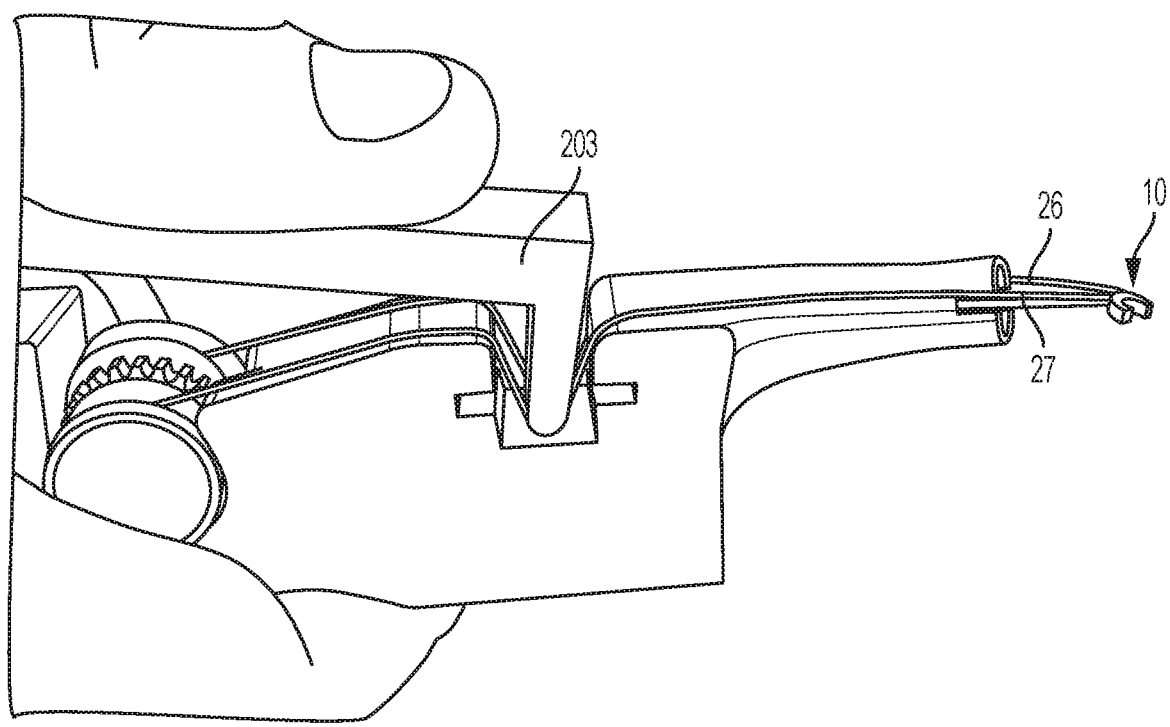
Figure 54:
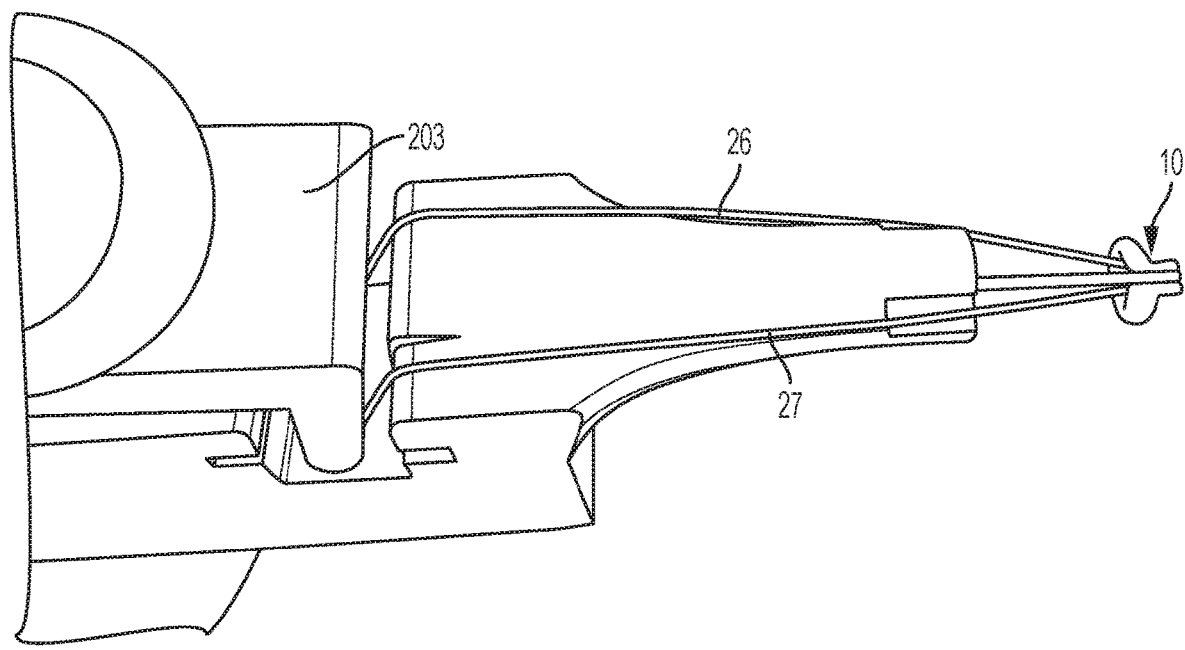
Figure 55:
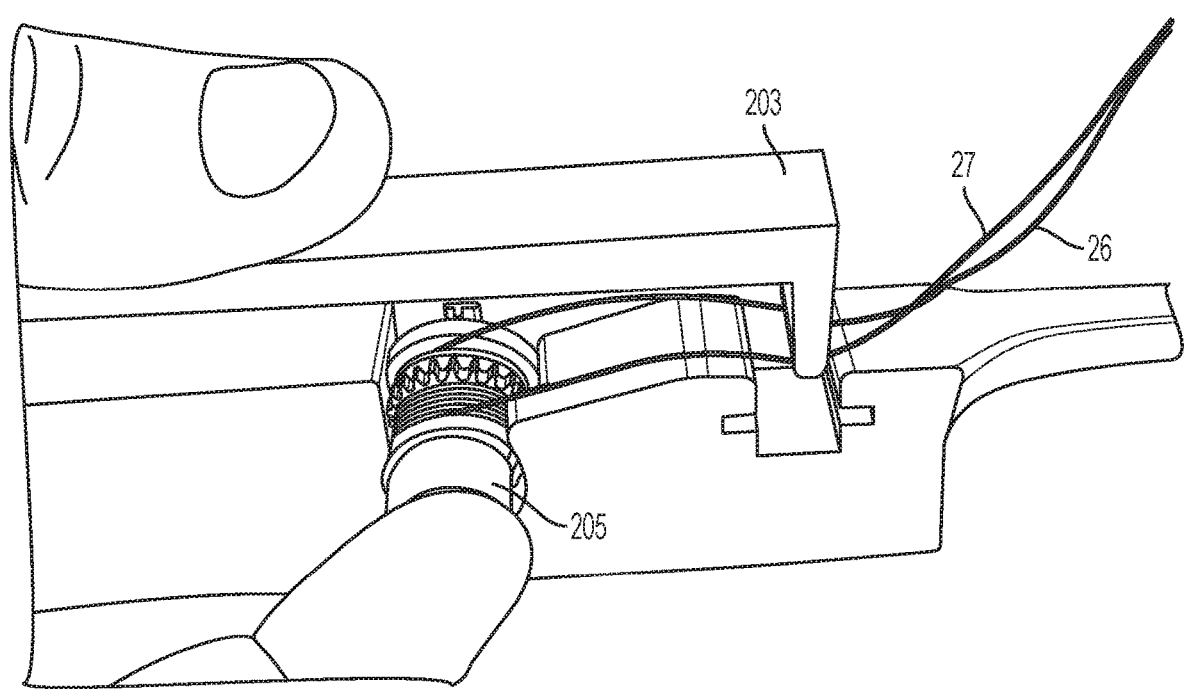
Figure 56:
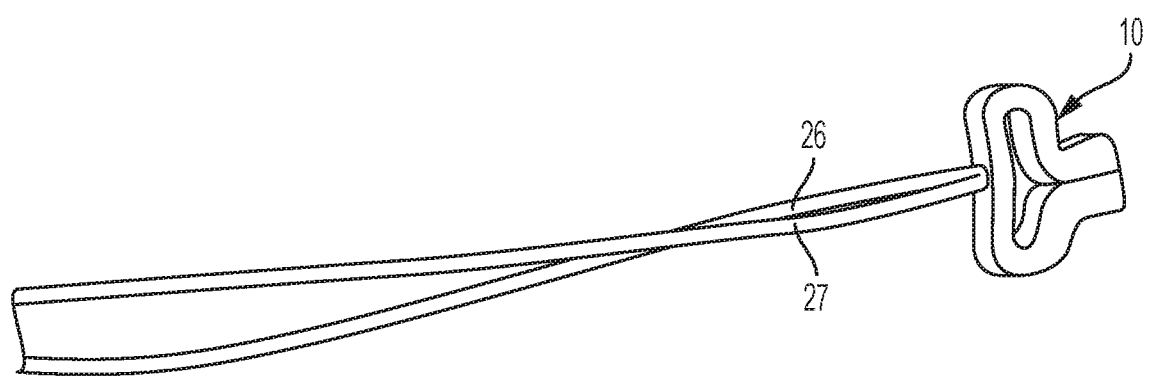
Figure 57:
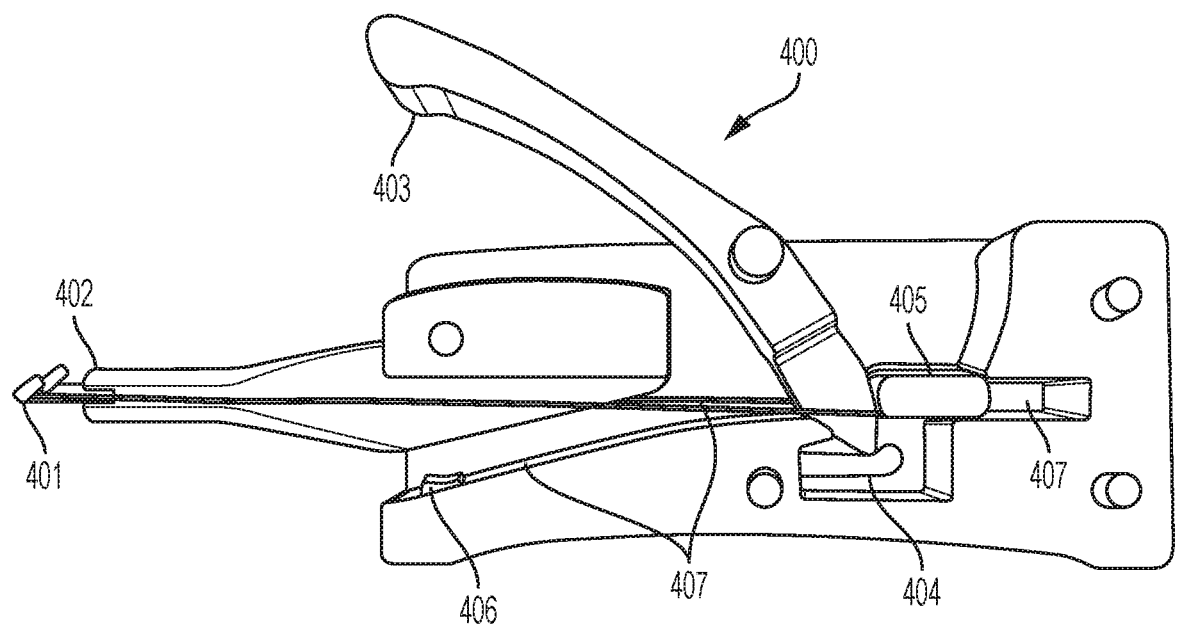
Figure 58:
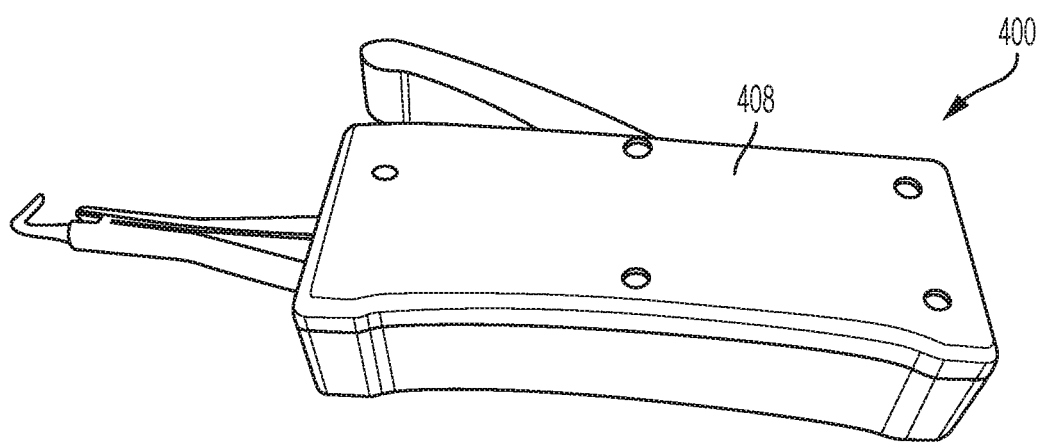
Figure 59:
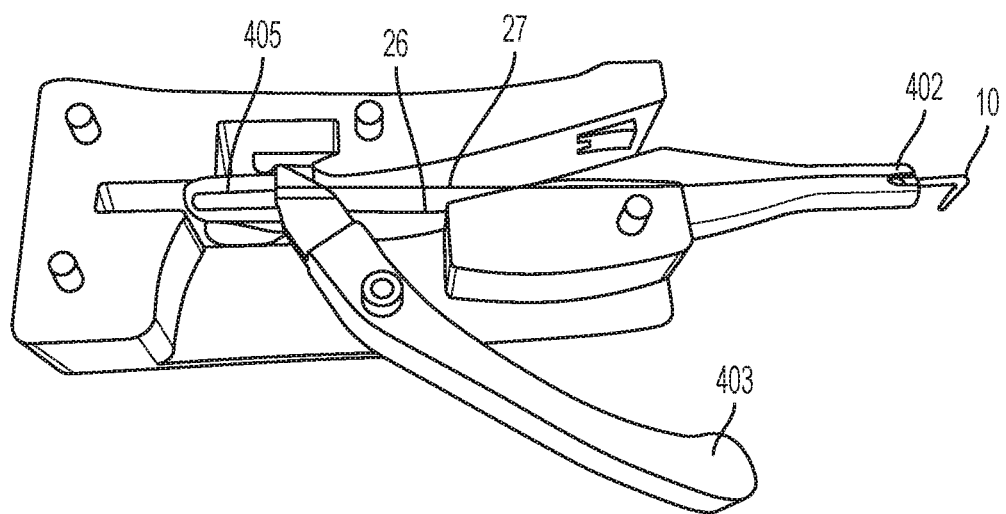
Figure 60:
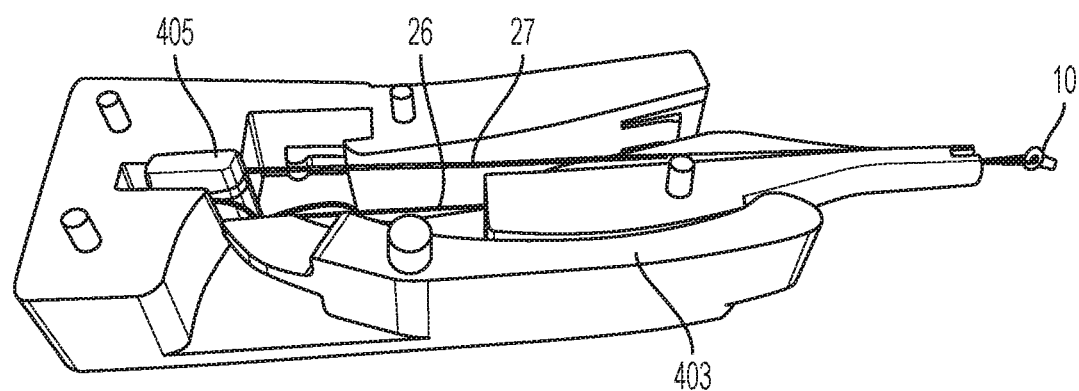
Figure 61:
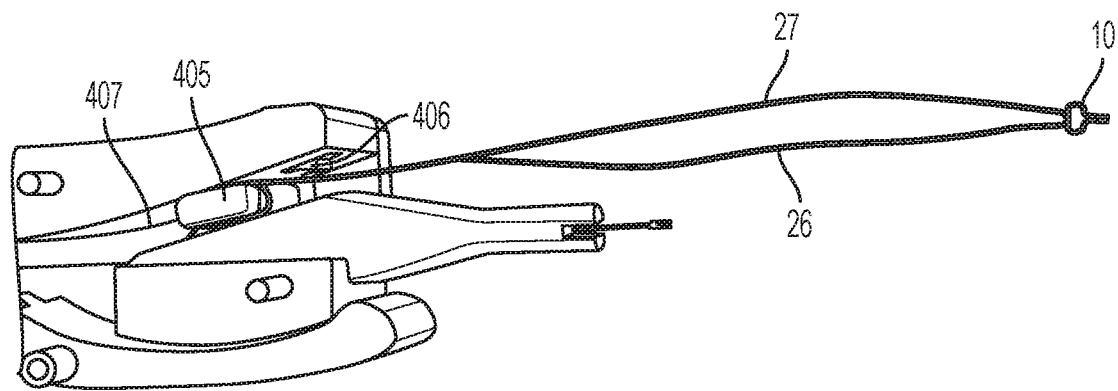
Figure 62:
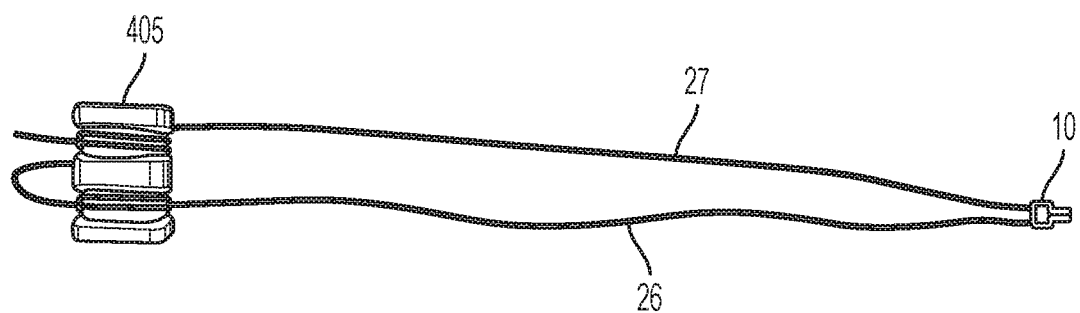

FIG. 29C is a side view schematic representation of the suture anchor of FIG. 29A loaded onto the anchor driver in the fully deployed configuration according to an alternative embodiment FIG. 30 is a first side view schematic representation of an alternative embodiment of the multi-barrel drill guide and anchor deployment assembly in the pre-drill, pre-anchor deployment, pre-actuated configuration according to an embodiment;

FIG. 31 is a first side view schematic representation of the multi-barrel drill guide and anchor deployment assembly of FIG. 30 in the drill, pre-anchor deployment, pre-actuated configuration according to an embodiment;

FIG. 32 is a first side view schematic representation of the multi-barrel drill guide and anchor deployment assembly of FIG. 30 in the post-drill, pre-anchor deployment, pre-actuated configuration according to an embodiment;

FIG. 33 is a first side view schematic representation of the multi-barrel drill guide and anchor deployment assembly of FIG. 30 in the post-drill, actuated/deployed configuration with the suture anchor in the deployed state according to an embodiment;

FIG. 34 is a first side view schematic representation of the suture anchor of FIG. 33 in the deployed state according to an embodiment;

FIG. 35 is a side view schematic representation of an additional embodiment of the suture anchor in the undeployed state according to an embodiment;

FIG. 36 is a side view schematic representation of the suture anchor of FIG. 35 shortened and expanded in the deployed state according to an embodiment;

FIG. 37 is a side view schematic representation of a disposable drill with a pre-installed drill bit according to an alternative embodiment;

FIG. 38 is a schematic representation of an all suture soft tissue fixation device according to an embodiment;

FIG. 39 is a side view schematic representation of an anchor driver according to an alternative embodiment;

FIG. 40 is a side view schematic representation of a portion of the anchor driver of FIG. 39;

FIG. 41 is a perspective view schematic representation of a spool portion of the anchor driver of FIG. 39;

FIG. 42 is a perspective view schematic representation of a safety bar portion of the anchor driver of FIG. 39;

FIG. 43 is a side perspective view schematic representation of a portion of the anchor driver of FIG. 39;

FIG. 44 is a top view schematic representation of a portion of the anchor driver of FIG. 39;

FIG. 45 is a side perspective view schematic representation of a portion of the anchor driver of FIG. 39;

FIG. 46 is a side perspective view schematic representation of a portion of the anchor driver of FIG. 39;

FIG. 47 is a side perspective view schematic representation of a fully assembled anchor driver of FIG. 39;

FIG. 48 is a side perspective view schematic representation of a portion of the anchor driver of FIG. 47;

FIG. 49 is a side view schematic representation of a portion of the anchor driver of FIG. 47;

FIG. 50 is a side perspective view schematic representation of a portion of the anchor driver of FIG. 47;

FIG. 51 is a side view schematic representation of a portion of the anchor driver of FIG. 47;

FIG. 52 is a side perspective view schematic representation of a portion of the anchor driver of FIG. 47;

FIG. 53 is a side perspective view schematic representation of a portion of the anchor driver of FIG. 47;

FIG. 54 is a top perspective view schematic representation of a portion of the anchor driver of FIG. 47;

FIG. 55 is a side perspective view schematic representation of a portion of the anchor driver of FIG. 47;

FIG. 56 is a perspective view schematic representation of an anchor in a fully deployed configuration/position/state;

FIG. 57 is a side view schematic representation of an anchor driver according to an alternative embodiment;

FIG. 58 is a side view schematic representation of a fully assembled anchor driver of FIG. 57;

FIG. 59 is a side perspective view schematic representation of the anchor driver of FIG. 57;

FIG. 60 is a side perspective view schematic representation of the anchor driver of FIG. 57;

FIG. 61 is a side perspective view schematic representation of a portion of the anchor driver of FIG. 57; and FIG. 62 is a perspective view schematic representation of an anchor in a fully deployed configuration/position/state.

DETAILED DESCRIPTION OF THE INVENTION

Figure 1:
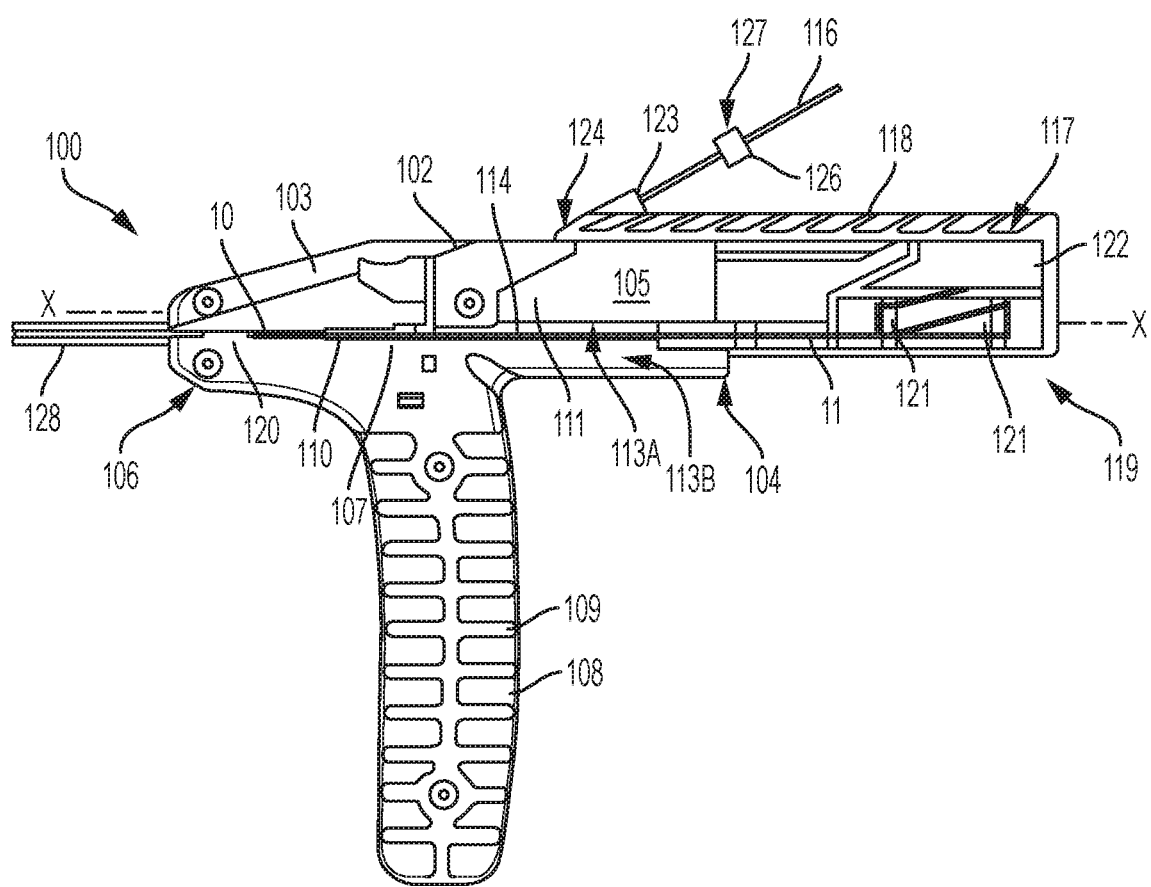
FIG. 1 is a first side view schematic representation of a multi-barrel drill guide and anchor deployment assembly in the pre-drill, pre-anchor deployment, pre-actuated configuration according to an embodiment.

Referring now to the drawings, wherein like reference numerals refer to like parts throughout, there is seen in FIG. 1 a fully assembled first side 103 view schematic representation of a multi-barrel drill guide and anchor deployment assembly 100 in the pre-drill, pre-anchor deployment, pre-actuated configuration according to an embodiment. In the depicted embodiment, the assembly 100 includes, but is not limited to, a distal elongated body 102 extending along a central longitudinal axis x-x having a proximal end 104 and a distal end 106, a handle 108 (which can include gripping features 109) extending from the elongated body 102 between the proximal end 104 and a distal end 106, a distal tube or guide tip 128 (which can include gripping projections or teeth to assist with setting and maintaining position on bone) extending from the distal end 106, and a proximal sliding inserter/anchor driver 118/114. The elongated body 102 has an exterior, portions of which are sufficiently enclosed (as described above and shown in the FIGs.). The exterior portion of the elongated body 102 preferably comprises no movable parts that complicate or interfere with easy use of the assembly 100.

As shown in FIG. 1, the handle 108 extends approximately perpendicular from the elongated body 102 between the proximal end 104 and the distal end 106 to increase balance and control of the assembly 100. However, the handle 108 may extend at various angles relative to the central longitudinal axis x-x, from any location along the elongated body 102, to provide stability when the user grips the handle 108 to place the assembly 100 against a desired pilot hole location on a bone.

Still referring to FIG. 1, the elongated body 102 comprises a slot 120 extending in a proximal direction along an axis parallel to the central longitudinal axis x-x from the distal end 106 through at least a distal portion of the elongated body 102, through a first opening 107 (formed in the top of the handle 108 and/or in the elongated body 102) and to a second larger opening 111 (formed in the top of the handle 108 and/or in the elongated body 102) which extends to the proximal end 104. The slot 120 and openings 107, 111 can extend along an axis perpendicular to the central longitudinal axis x-x and through the elongated body 102 into a first channel 110 (see FIG. 5) to the inside of a second side 105 of the assembly 100.

As shown in FIG. 1, a track 113—including a first portion 113A positioned along the inside of a second side 105, and second portion 113B positioned along the bottom inside of the elongated body 102—extends in a distal direction along an axis parallel to the central longitudinal axis x-x from the proximal end 104 toward the distal end 106, ending at or before the distal end 106. The track 113 facilitates the movement of the proximal sliding inserter 118 along an axis parallel to the central longitudinal axis x-x from the proximal end 104 through at least a distal portion of the elongated body 102 (as described in detail below).

Figure 5:
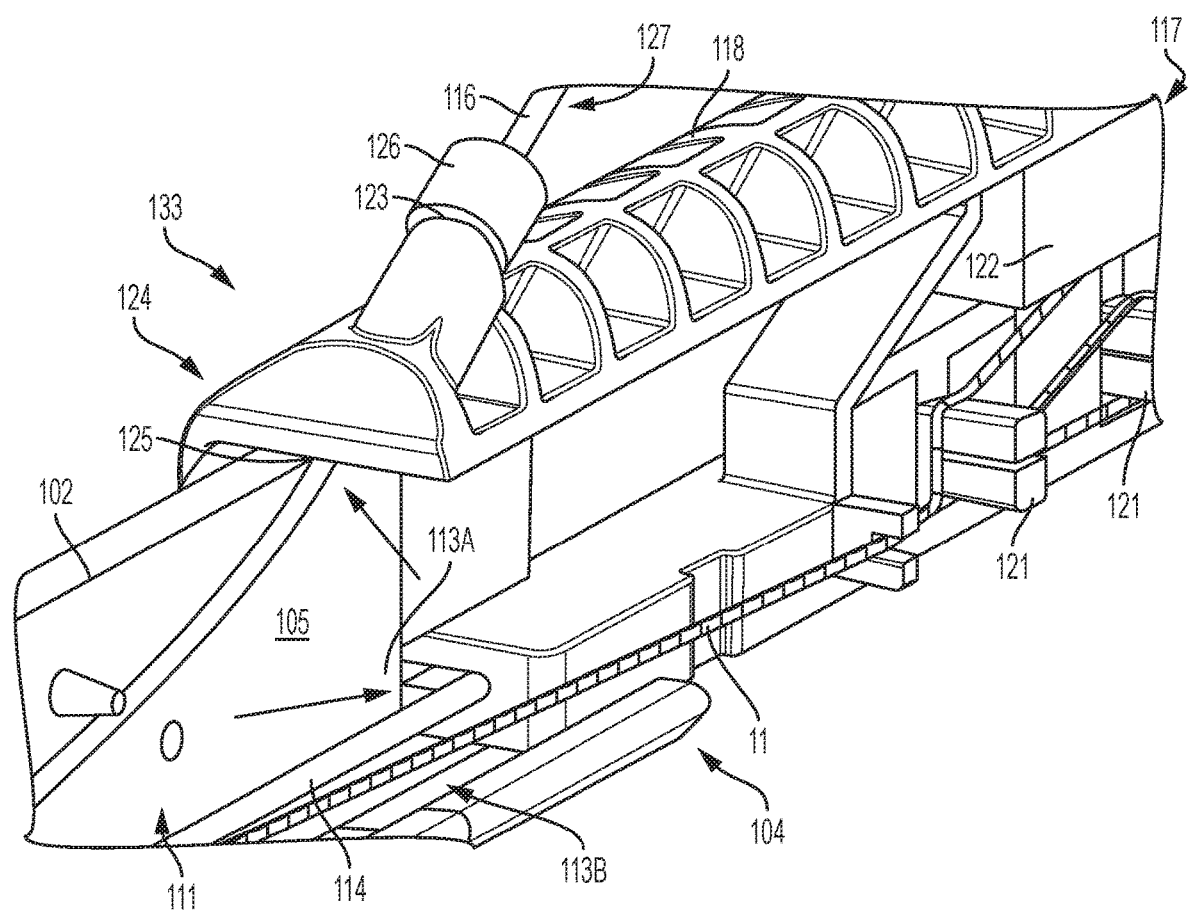
FIG. 5 is a cross-sectional front/perspective view schematic representation of the locking mechanism of the multi-barrel drill guide and anchor deployment assembly of FIG. 2 according to an embodiment.
Figure 10:
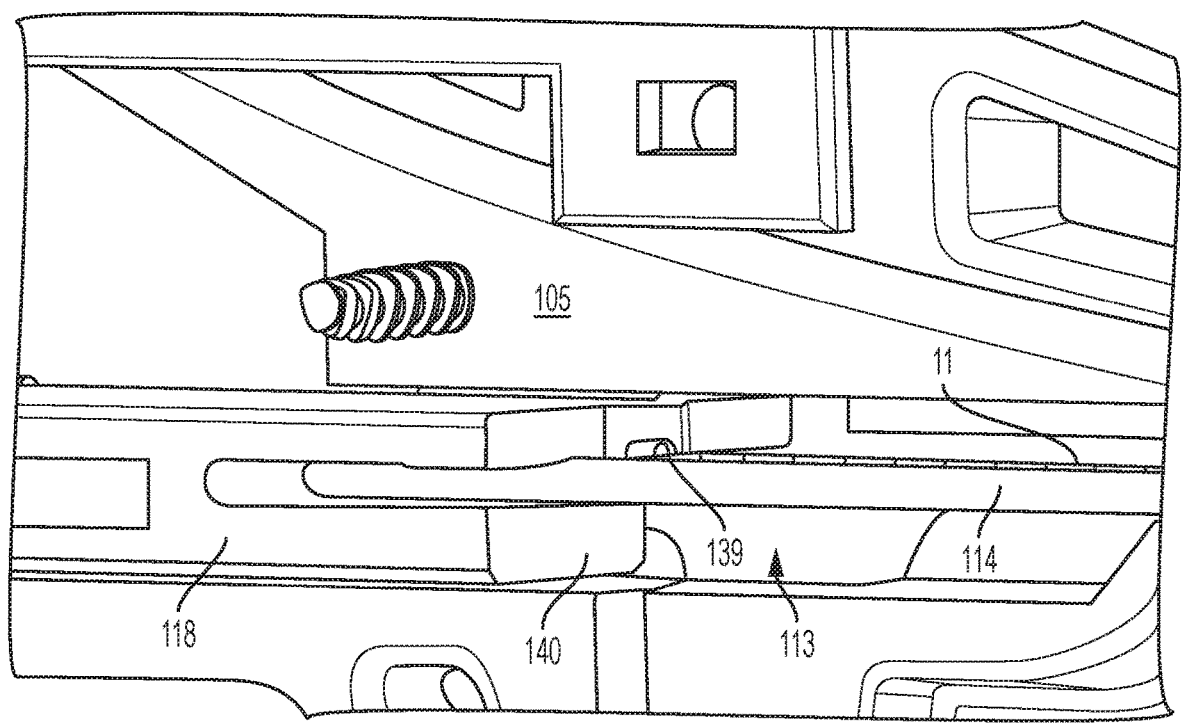
FIG. 10 is a close-up cross-sectional second side view schematic representation of the shallow deployment button of the multi-barrel drill guide and anchor deployment assembly of FIG. 9 according to an embodiment.

The sliding inserter 118 comprises an anchor driver 114 attached thereto (shown in FIGS. 5 and 10). In a pre-actuated/undeployed configuration, the anchor driver 114 of the sliding inserter 118 extends from the proximal end 104 of the elongated body 102 through at least a distal portion of the elongated body 102. However, in its pre-actuated/undeployed configuration, the anchor driver 114 does not extend into the distal tube or guide tip 128 (shown in FIG. 8). When fully assembled, the multi-barrel drill guide and anchor deployment assembly 100 comprises a suture anchor 10 with a passing filament 11 loaded on the anchor driver 114 (described in detail later). As fully assembled, the suture anchor 10 is loaded on distal end 115 of the anchor driver 114, while the passing filament 11 extends along the length of the anchor driver 114 and is wrapped around or otherwise secured by a loading mechanism 117 at a proximal end 119 of the sliding inserter 118 (also shown in FIGS. 5 and 12). The proximal end can also include a malleting section or area on the back surface of the proximal end. This malleting section can provide a user with a surface to mallet and assist with setting and maintaining the distal end of the guide tube 128 in bone prior to drilling the hole. In the depicted embodiment, the loading mechanism 117 includes one or more notches 121 and a flexible substrate 122. In one embodiment, the flexible substrate 122 is composed of a foam material; however, any other semi-flexible material may be used. The flexibility of the flexible substrate 122 is such that the flexible substrate 122 may be easily removed from the sliding inserter 118 to free the passing filament 11 (which may or may not be attached to needles, as should be understood by a person of skill in the art in conjunction with a review of this disclosure). As shown, the flexible substrate 122 is sized or otherwise dimensioned to fit within a portion of the proximal end 119 of the sliding inserter 118. In the depicted embodiment, the passing filament 11 is removably secured by the one or more notches 121 and the flexible substrate 122 to allow for release of the suture anchor 10 from the assembly 100 when the suture anchor 10 is in a deployed state in a pilot hole.

Still referring to FIG. 1, the sliding inserter 118 also comprises an opening 123 configured to receive a drill bit 116. In the depicted embodiment, the opening 123 is located or otherwise positioned at a distal end 124 of the sliding inserter 118. In the pre-drill configuration (FIG. 1) and drill configuration (FIGS. 2-3), the opening 123 on the sliding inserter 118 is aligned with an opening 125 on the elongated body 102. The opening 125 is located or otherwise positioned between the proximal end 104 and the distal 106 of the elongated body 102 and connects to a second channel 112 within the elongated body 102. Thus, in the pre-drill configuration shown in FIG. 1, the drill bit 116 extends through the opening 123 in the sliding inserter 118 and into the opening 125 of the elongated body 102. In the drill configuration (shown in FIGS. 2-3 and described in detail below), the drill bit 116 is advanced into the second channel 112 of the elongated body 102 and through the connected distal tube or guide tip 128. In comparison, in FIG. 1, the assembly 100 is in a pre-drill configuration wherein the drill bit 116 extends only partially through the second channel 112 and not through the distal tube or guide tip 128.

Figure 2:
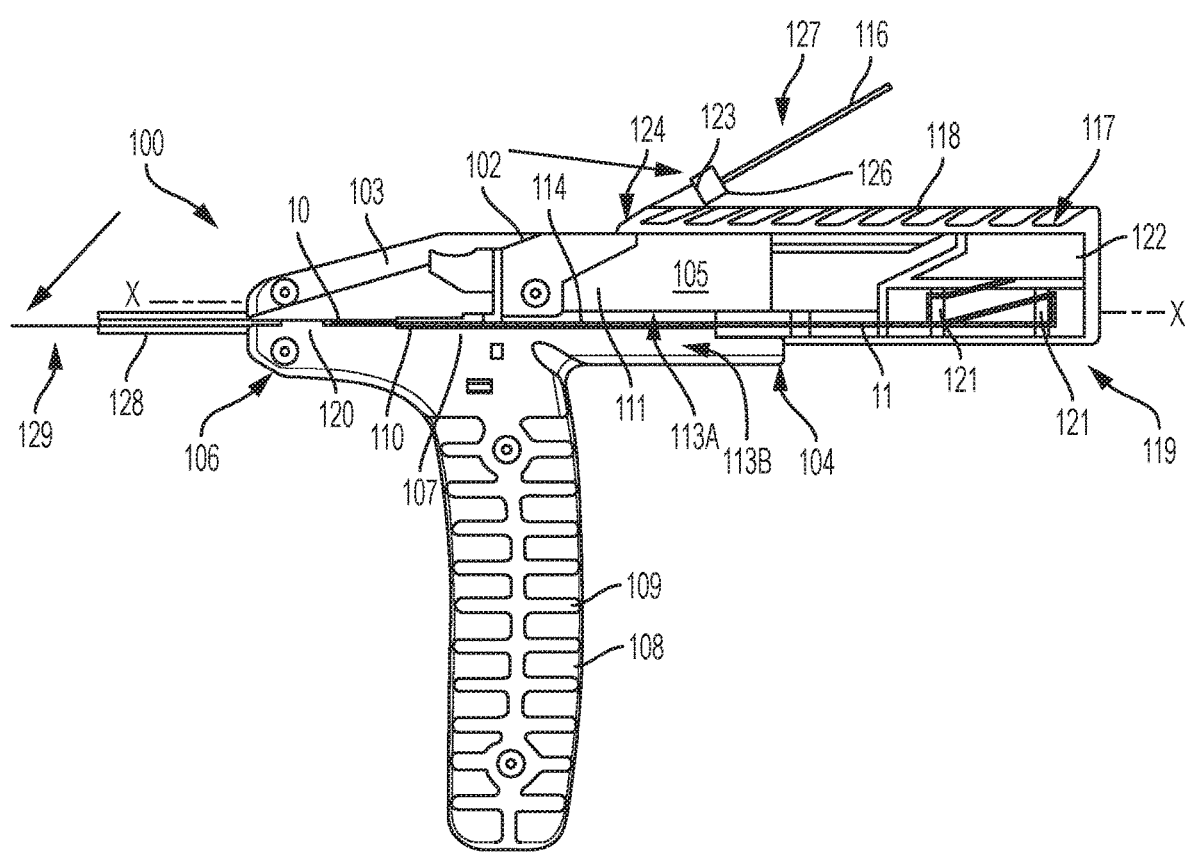
FIG. 2 is a first side view schematic representation of a multi-barrel drill guide and anchor deployment assembly in the drill, pre-anchor deployment, pre-actuated configuration according to an embodiment.

Turning now to FIG. 2, there is shown a fully assembled first side 103 view schematic representation of a multi-barrel drill guide and anchor deployment assembly 100 in the drill, pre-anchor deployment, pre-actuated configuration according to an embodiment. In the depicted embodiment, the drill bit 116 is in the drill configuration such that the drill bit 116 extends through the second channel 112 at a length corresponding to the desired or proper depth for the pilot hole. In the embodiment shown, the drill bit 116 comprises a depth stop 126 at its proximal end 127, which abuts the opening 123 in the sliding inserter 118 when the drill bit 116 has reached the proper depth in the pilot hole. The depth stop 126 prevents the drill bit 116 from extending any deeper into the bone than the proper depth for the pilot hole in a particular procedure. Similarly, the depth stop 126 also allows the user to determine if the drill bit 116 has been advanced far enough into the bone. As shown in FIG. 2, in the drill configuration, the distal end 129 of the drill bit 116 extends out from the distal tube or guide tip 128 in order to drill the pilot hole.

Figure 3:
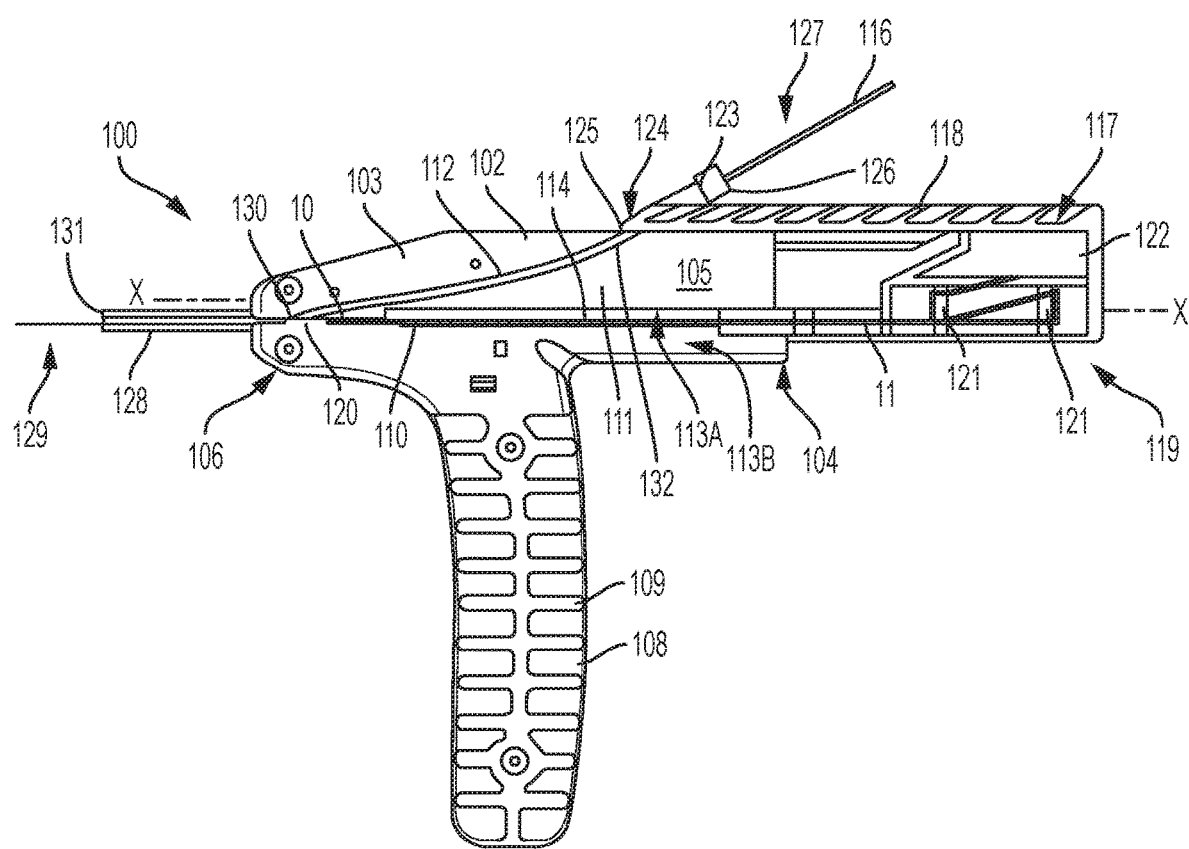
FIG. 3 is a cross-sectional first side view schematic representation of the multi-barrel drill guide and anchor deployment assembly of FIG. 2 according to an embodiment.

Referring now to FIG. 3, there is shown a cross-sectional first side 103 view schematic representation of the multi-barrel drill guide and anchor deployment assembly 100 of FIG. 2. In the depicted embodiment, the elongated body 102 comprises the first channel 110 and the second channel 112 for receiving tools to drill the pilot hole and to insert the suture anchor 10. As shown in FIG. 3, the first channel 110 extends from proximal end 104 to the distal end 106 of the elongated body 102, while the second channel 112 extends from the opening 125 on the elongated body 102 to the distal end 106. Thus, in the depicted embodiment, the first channel 110 and the second channel 112 have different entry points along the elongated body 102. The two separate entry points accommodate the two tools—the drill bit 116 for drilling the pilot hole and the anchor driver 114 for inserting the suture anchor 10 into the drilled pilot hole.

As recited above, the first channel 110 extends approximately straight in a distal direction along an axis parallel to the central longitudinal axis x-x of the elongated body 102 from the proximal end 104 to distal end 106. The second channel 112 extends at an angle relative to the first channel 110 and to the central longitudinal axis x-x, which allows the first channel 110 and the second channel 112 to have separate entry points and one convergence area 130. Thus, although the first channel 110 and the second channel 112 extend from different entry points along the elongated body 102, the first channel 110 and the second channel 112 share a convergence area 130 proximal to a single exit point on the distal end 106 of the elongated body 102. In other words, the convergence area 130 is where the channels 110, 112 converge prior (i.e., proximal) to the single exit point. In the depicted embodiment, the single exit point is at a distal end 131 of the distal tube or guide tip 128.

Accordingly, the first channel 110 is separate and distinct from the second channel 112 between the entry points and the convergence area 130. Thus, a user can employ the drill bit 116 in the second channel 112 by extending the drill bit 116 into the convergence area 130 and out of the distal tube or guide tip 128, while the anchor driver 114 can sit (be positioned and not move) in the first channel 110. As shown in FIG. 3, the drill bit 116 is in the drill configuration with the distal end 129 of the drill bit 116 extending from the distal tube or guide tip 128 and the depth stop 126 abutting the opening 123 on the sliding inserter 118.

Still referring to FIG. 3 and as stated above, the second channel 112 extends at an angle relative to the central longitudinal axis x-x of the elongated body 102 and away from the first channel 110 in the proximal direction. In the depicted embodiment, the second channel 112 comprises a bend 132, which is curved in a direction away from the first channel 110. The second channel 112 may comprise the bend 132 at any point along the length of the second channel 112 between the convergence area 130 and the opening 125 on the elongated body 102. This bend 132 is structured and configured to position/guide the semi-flexible drill bit 116 through the angled second channel 112 and straight out of the distal tube or guide tip 128. Stated differently, the bend 132 curves the semi-flexible drill bit 116 such that the drill bit 116 is at an angle capable of exiting the distal tube or guide tip 128, which is aligned with the first channel 110 (parallel to the central longitudinal axis x-x). As shown in FIG. 3, the proximal end 127 of the drill bit 116 is at an angle relative to the distal end 129 of the drill bit 116.

As shown in FIG. 3, the first channel 110 is substantially straight along the bottom of the elongated body 102. When the drill bit 116 is in the drill configuration, the drill bit 116 extends through the convergence area 130 and out of the distal tube or guide tip 128. In the pre-drill configuration (shown in FIG. 1) and drill configuration, the anchor driver 114 and suture anchor 10 is proximal the convergence area 130 in the first channel 110. Without obstruction by the anchor driver 114 (and suture anchor 10) in the convergence area 130, the drill bit 116 is free to pass via the second channel 112 through the convergence area 130 and out of the distal tube and guide tip 128. However, the first channel 110 is aligned with the convergence area 130 and the distal tube and guide tip 128 such that the anchor driver 114 can be easily extended through the convergence area 130 and the distal tube and guide tip 128 without moving the assembly 100 (after the drill bit 116 has been removed). The suture anchor 10 is less likely to miss the previously drilled hole, and is more likely to be inserted in the pilot hole without adjusting the distal end 131 of the distal tube and guide tip 128 to sufficiently line up the pilot hole for deployment of the suture anchor 10. Accordingly, if the position of the assembly 100 is maintained with respect to the bone after the pilot hole has been drilled, the suture anchor 10 with passing filament 11 should be able to be easily delivered into the previously formed pilot hole without having to move or change the angle of the distal tube and guide tip 128 to locate the pilot hole.

Figure 4:
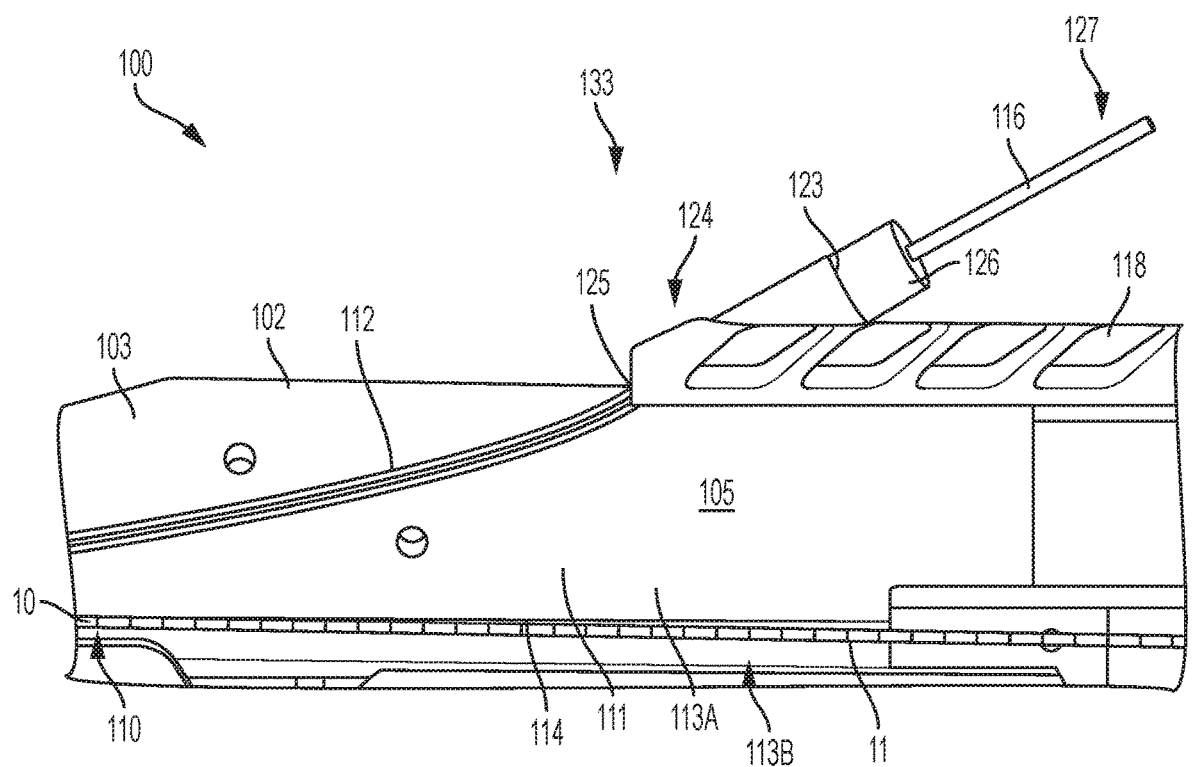
FIG. 4 is a close-up cross-sectional first side view schematic representation of a locking mechanism of the multi-barrel drill guide and anchor deployment assembly of FIG. 2 according to an embodiment.

Turning now to FIG. 4, there is shown is a close-up cross-sectional first side 103 view schematic representation of a locking mechanism 133 of the multi-barrel drill guide and anchor deployment assembly 100 of FIG. 2. In the depicted embodiment, the locking mechanism 133 comprises the drill bit 116, the opening 123 on the sliding inserter 118 and the opening 125 on the elongated body 102. When the drill bit 116 extends through both openings 123, 125 such that the distal end 129 of the drill bit 116 passes through at least a portion of the second channel 112 (and the elongated body 102) and the proximal end 127 of the drill bit 116 remains outside or exterior to the elongated body 102, the drill bit 116 functions as a locking mechanism 133. The drill bit 116 maintains the openings 123, 125 in alignment and thereby blocks the sliding inserter 118 from advancing in the distal direction along the track 113. Thus, the user can operate the drill bit 116 to drill the pilot hole without risking unintentional movement of the anchor driver 114 (and the suture anchor 10).

Figure 6:
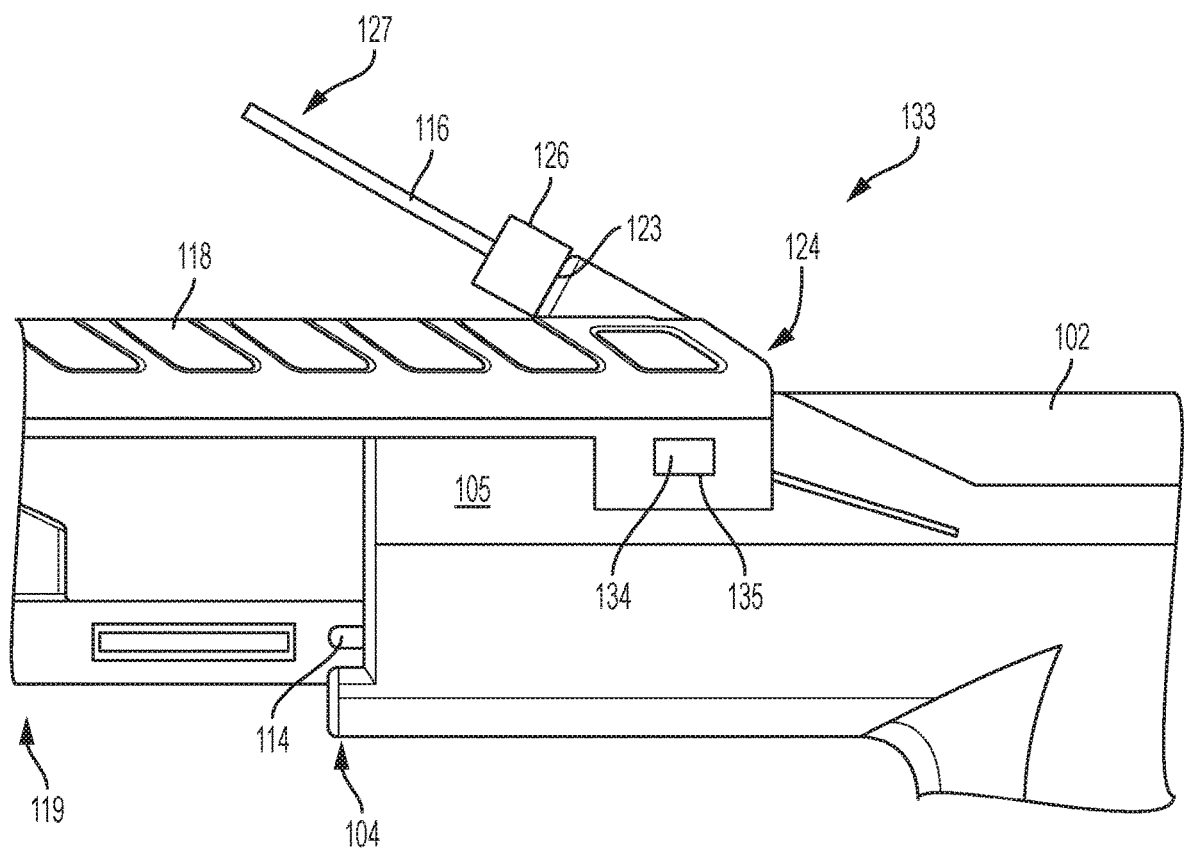
FIG. 6 is a close-up second side view schematic representation of a notch of the locking mechanism of the multi-barrel drill guide and anchor deployment assembly of FIG. 2 according to an embodiment.

Referring now to FIGS. 5-6, there are shown first side 103 and second side 105 views of an illustrative embodiment of the locking mechanism 133. First, FIG. 5 shows a cross-sectional front/perspective view of the locking mechanism 133 on the first side 103 of the assembly 100. In the depicted embodiment, movement of the sliding inserter 118 along the track 113 between the first side 103 and the interior of the second side 105 of the assembly 100 is blocked or otherwise prohibited when the drill bit 116 extends through the opening 123 in the sliding inserter 118 and the opening 125 in the elongated body 102. Movement of the sliding inserter 118 is thus contained to movement parallel to the central longitudinal axis x-x by the track 113 and is either permitted or obstructed by the absence or presence, respectively, of the drill bit 116.

Next, FIG. 6 shows a close-up second side 105 view of a notch 134 of the locking mechanism 133 on the assembly 100 according to an additional embodiment of the locking mechanism 133. In the depicted embodiment, the locking mechanism 133 additionally comprises a notch 134 on the second side 105 of the assembly 100. As shown, the notch 134 extends outward from the elongated body 102. The notch 134 is configured to engage with an aperture 135 in the sliding inserter 118. In the depicted embodiment, the notch 134 and the corresponding aperture 135 are rectangular; however, any other compatible configurations of the notch 134 and aperture 135 may be used.

Still referring to FIG. 6, in the pre-drill configuration (FIG. 1) and the drill configuration (FIGS. 2-3), the aperture 135 is engaged with the notch 134. In particular, the aperture 135 surrounds the notch 134. When the drill bit 116 is removed from the assembly 100, the user advances the sliding inserter 118 or otherwise applies force to the proximal end 119 of the sliding inserter 118 in the distal direction. Such force causes the aperture 135 of the sliding inserter 118 to slide past the notch 134 on the elongated body 102. The sliding inserter 118 may then continue to advance in the track 113 to place the suture anchor 10 in the pilot hole. To reset the assembly 100 (i.e., reload the assembly 100 with a new suture anchor), the user moves the sliding inserter 118 along the track 113 in the proximal direction until the aperture 135 of the sliding inserter 118 engages or otherwise locks over the notch 134 on the elongated body 102. When the notch 134 is aligned with the aperture 135, the opening 123 in the sliding inserter 118 is aligned with the opening 125 in the elongated body 102. When the assembly 100 is reset and the aperture 135 is locked over the notch 134, the sliding inserter 118 cannot move any farther in the proximal direction.

Figure 7:
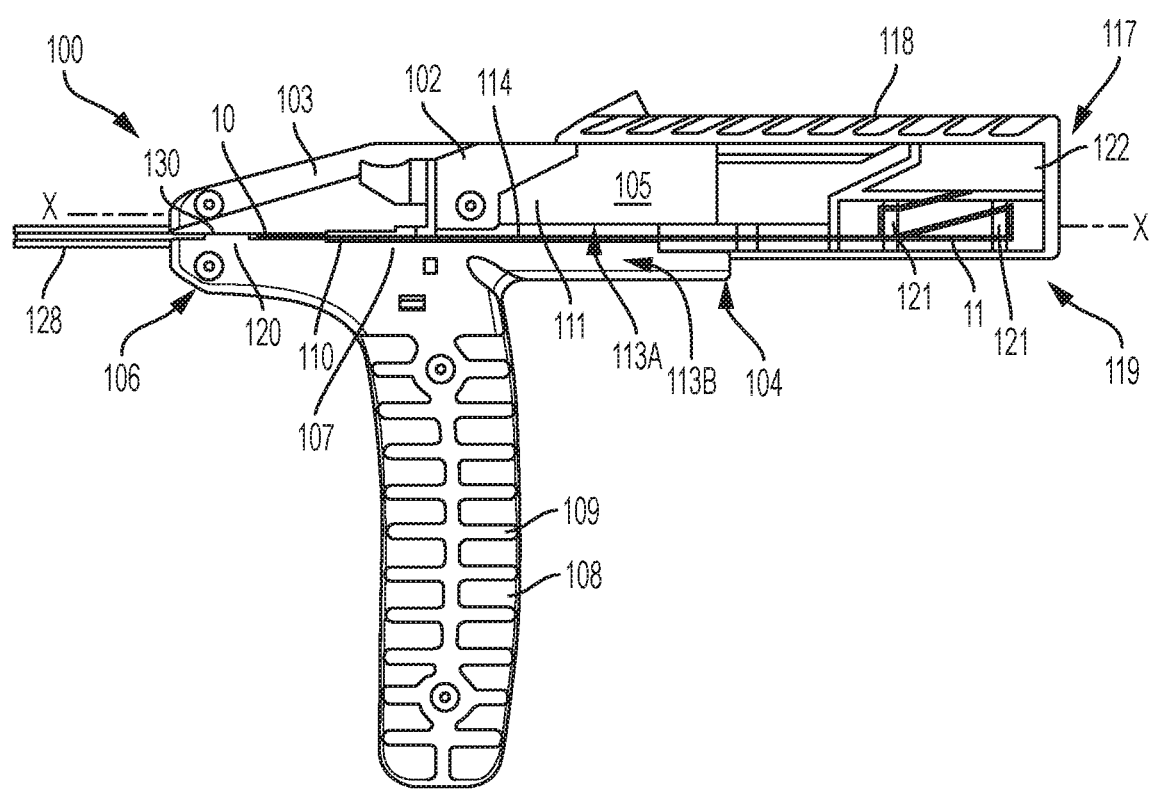
FIG. 7 is a first side view schematic representation of a multi-barrel drill guide and anchor deployment assembly in the post-drill, pre-anchor deployment, pre actuated configuration according to an embodiment.

Turning now to FIG. 7, there is shown a first side 103 view schematic representation of a multi-barrel drill guide and anchor deployment assembly 100 in the post-drill, pre-anchor deployment, pre-actuated configuration according to an embodiment. In the pre-drill and drill configurations shown in FIGS. 1-3, a suture anchor 10 has been pre-loaded onto the distal end 115 of the anchor driver 114 of the sliding inserter 118. In such configurations, the distal end 115 of the anchor driver 114 (with the suture anchor 10) extends through the first channel 110 up to the convergence area 130, but not into the convergence area 130. After the pilot hole has been drilled and the drill bit 116 has been removed, as shown in the post-drill configuration of FIG. 7, the anchor driver 114 (with the suture anchor 10) is free to move through the convergence area 130 and out of the distal tube and guide tip 128.

Figure 8:
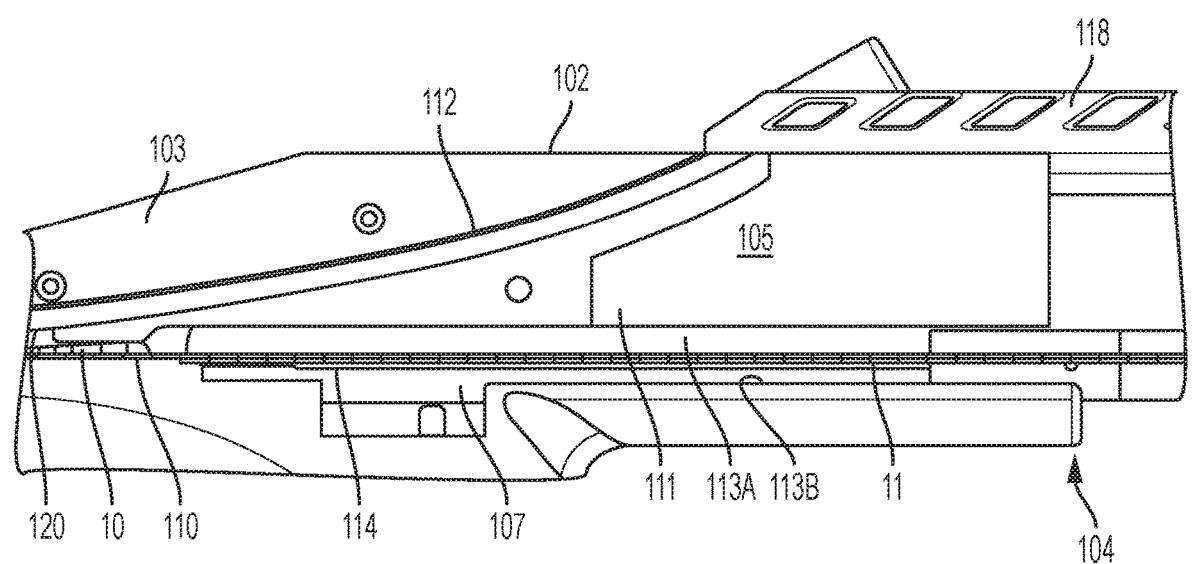
FIG. 8 is a close-up cross-sectional first side view schematic representation of the second channel of the multi-barrel drill guide and anchor deployment assembly of FIG. 7 according to an embodiment.

Referring briefly to FIG. 8, there is shown a close-up cross-sectional first side 103 view schematic representation of the second channel 112 of the multi-barrel drill guide and anchor deployment assembly 100 of FIG. 7. In the depicted embodiment, the drill bit 116 has been removed from the assembly 100 after the pilot hole has been drilled. As also shown in FIG. 7, the anchor driver 114 is free to advance along the first channel 110 via the sliding inserter 118. The sliding inserter 118 is free to move in the distal direction along the track 113 because the drill bit 116 is no longer in place to act as the locking mechanism 133 between the sliding inserter 118 and the elongated body 102.

Figure 9:
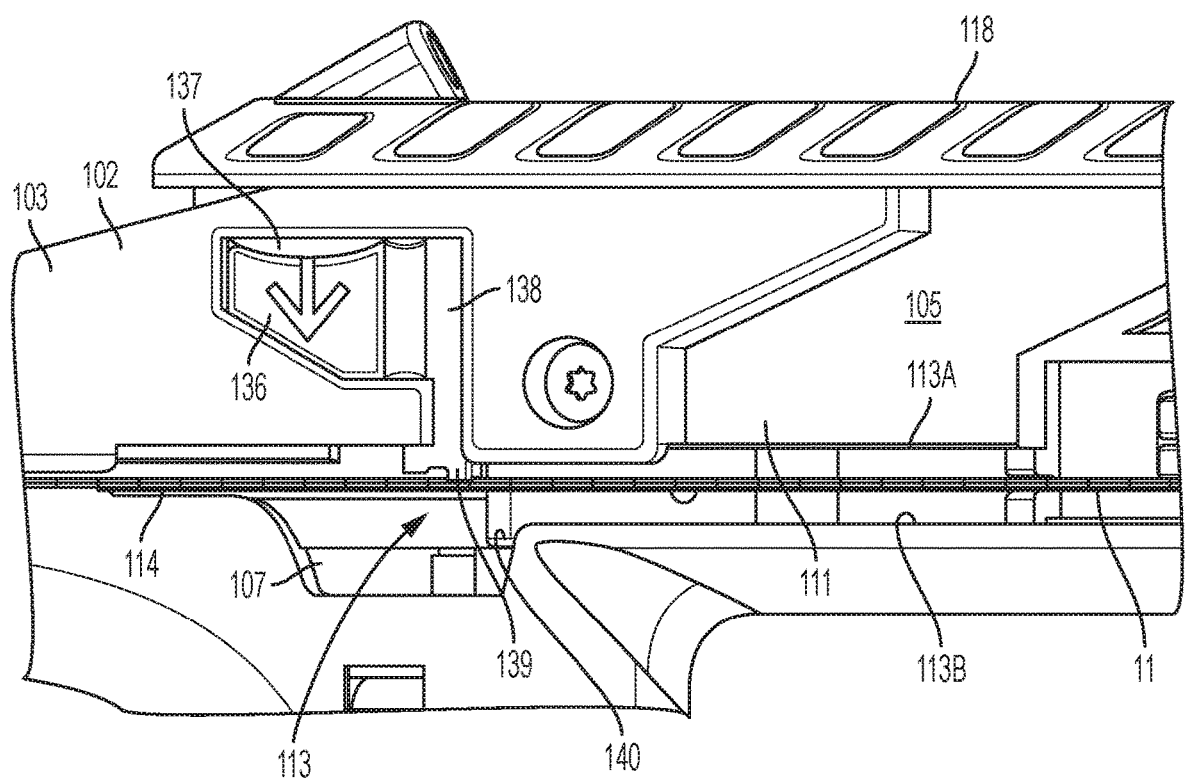
FIG. 9 is a close-up first side view schematic representation of the shallow deployment button of multi-barrel drill guide and anchor deployment assembly in the pre-actuated/undeployed configuration according to an embodiment.

Turning now to FIG. 9, there is shown a close-up first side 103 view schematic representation of a shallow deployment button 136 of multi-barrel drill guide and anchor deployment assembly 100 in the pre-actuated/undeployed configuration according to an embodiment. A shallow deployment button 136 is located between the proximal end 104 and the distal end 106 of the elongated body 102. In the depicted embodiment, the shallow deployment button 136 is located or otherwise positioned within a recess 137 on the first side 103 of the elongated body 102. However, the shallow deployment button 136 may be positioned at other appropriate locations along the elongated body 102. As shown in FIG. 9, the shallow deployment button 136 is substantially flush with the first side 103 of the elongated body 102 to prevent potential interference with use of the assembly 100 before the suture anchor 10 is deployed.

Still referring to FIG. 9, the shallow deployment button 136 is hingedly connected to the elongated body 102 within the recess 137. In the depicted embodiment, one side of the shallow deployment button 136 is connected to the elongated body 102 via a hinge 138 in the recess 137. In the pre-actuated/undeployed configuration (shown in FIG. 9), the shallow deployment button 136 has a flange 139 which extends from the recess 137 into the first opening 107 (formed in the top of the handle 108 and/or in the elongated body 102). In particular, the flange 139 extends into the path of the track 113.

Referring now to FIG. 10, there is shown a close-up cross-sectional second side 105 view schematic representation of the shallow deployment button 136 of the multi-barrel drill guide and anchor deployment assembly of FIG. 9. In a post-drill configuration, as described above, the sliding inserter 118 is free to advance along the track 113. The sliding inserter 118 moves along the track 113 until a portion 140 of the sliding inserter 118 contacts the flange 139 of the shallow deployment button 136, which extends into the path of the track 113, as shown in FIG. 9.

Figure 11:
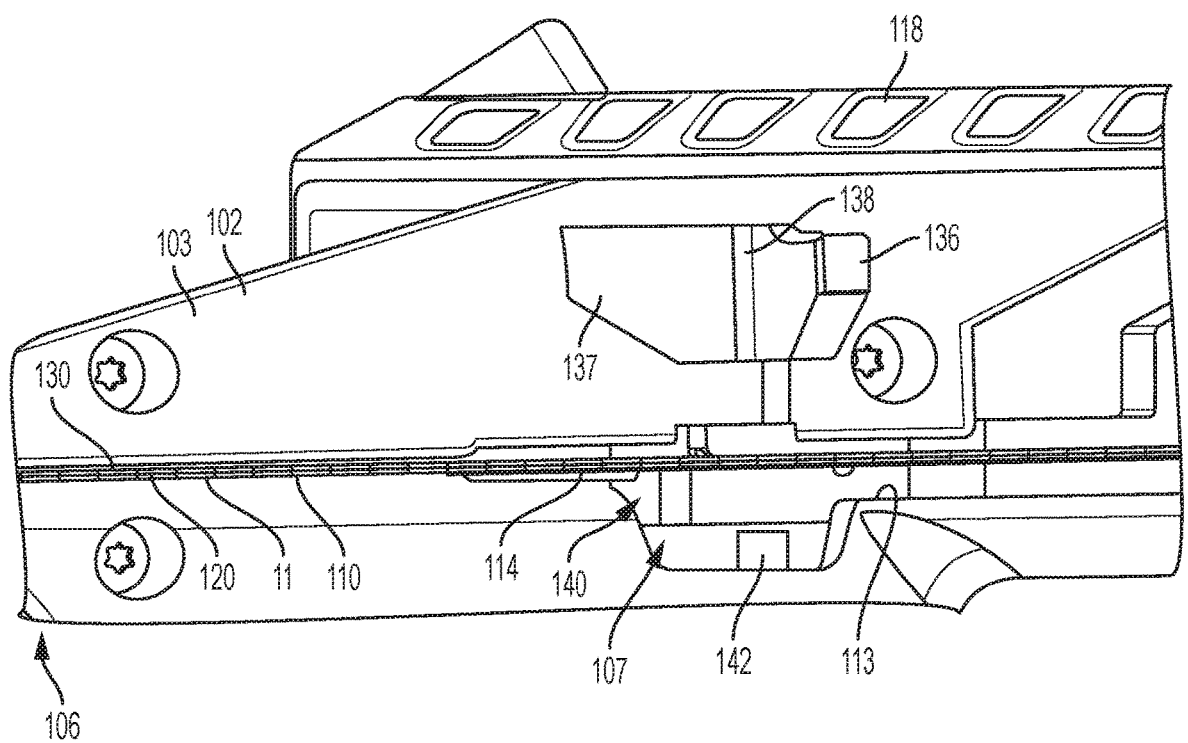
FIG. 11 is a close-up first side view schematic representation of the shallow deployment button of multi-barrel drill guide and anchor deployment assembly actuated/undeployed configuration according to an embodiment.

Turning now to FIG. 11, there is shown a close-up first side 103 view schematic representation of the shallow deployment button 136 of multi-barrel drill guide and anchor deployment assembly 100 in the actuated/undeployed configuration according to an embodiment. After the portion 140 of the sliding inserter 118 contacts the flange 139 of the shallow deployment button 136 in FIG. 10, continuing to advance the sliding inserter 118 in the distal direction causes the portion 140 of the sliding inserter 118 to apply force on the flange 139. Force on the flange 139 rotates the shallow deployment button 136 about the hinge 138, thereby rotating the shallow deployment button 136 out from the recess 137 to an actuated/undeployed configuration. The portion 140 of the sliding inserter 118 applies force on the flange 139 until the flange 139 is rotated out of the path of the track 113. With the flange 139 out of the path of the track 113, the sliding inserter 118 can advance farther distally along the track 113 to insert the suture anchor 10 into the pilot hole. When the flange 139 is out of the path of the track 113, the passing filament 11 extends in the first channel 110 and first opening 107 between the flange 139 and a feature 142 in the first opening 107 of the elongated body 102.

Figure 12:
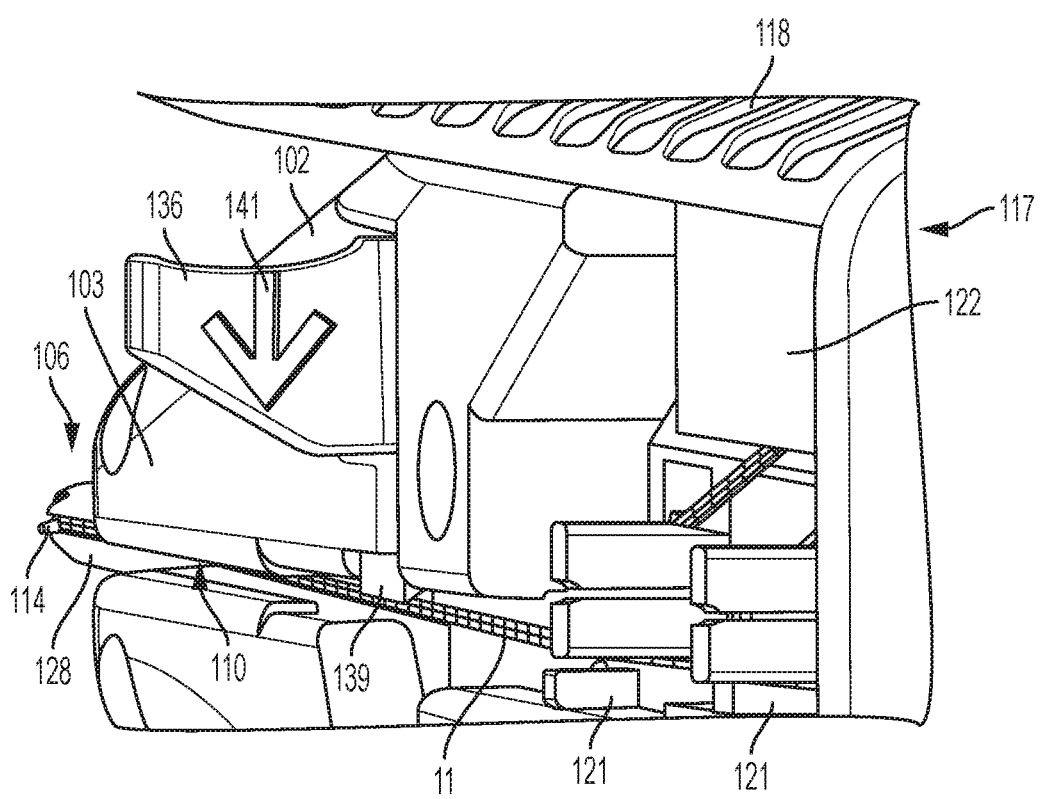
FIG. 12 is a close-up rear/perspective view schematic representation of the shallow deployment button of FIG. 11 according to an embodiment.
Figure 13:
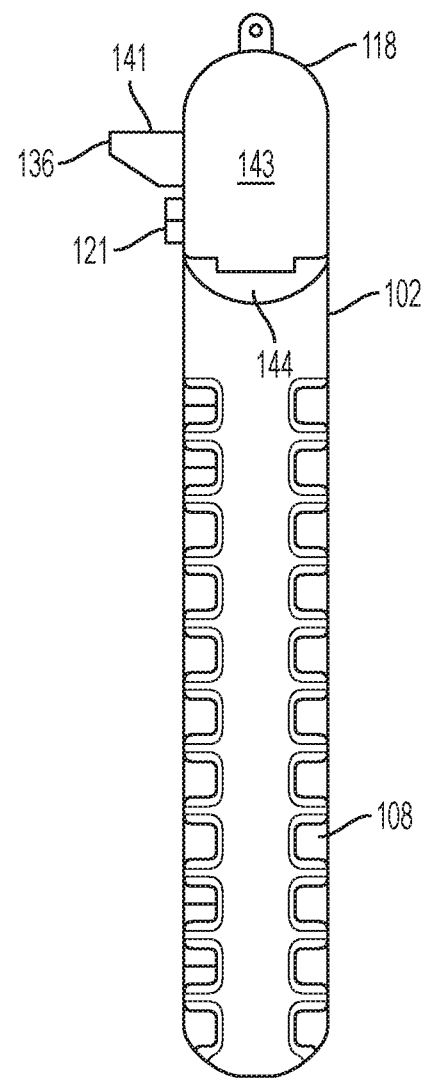
FIG. 13 is a rear view schematic representation of the shallow deployment button of FIG. 11 according to an embodiment.

Referring now to FIGS. 12-13, there is shown a close-up rear/perspective view and rear view schematic representations of the shallow deployment button 136 of FIG. 11. FIGS. 12-13 show the shallow deployment button 136 in the actuated/undeployed configuration after it is rotated from the recess 137. The shallow deployment button 136 comprises an indicator 141 which provides instructions for the user. In the depicted embodiment, the indicator 141 is an arrow pointing downward toward the feature 142 on the elongated body 102. In order to deploy and release the suture anchor 10 from the assembly 100, the user will press the shallow deployment button 136 downward toward the feature 142 (i.e., in the direction of the indicator 141) (as described in detail below).

Figure 14:
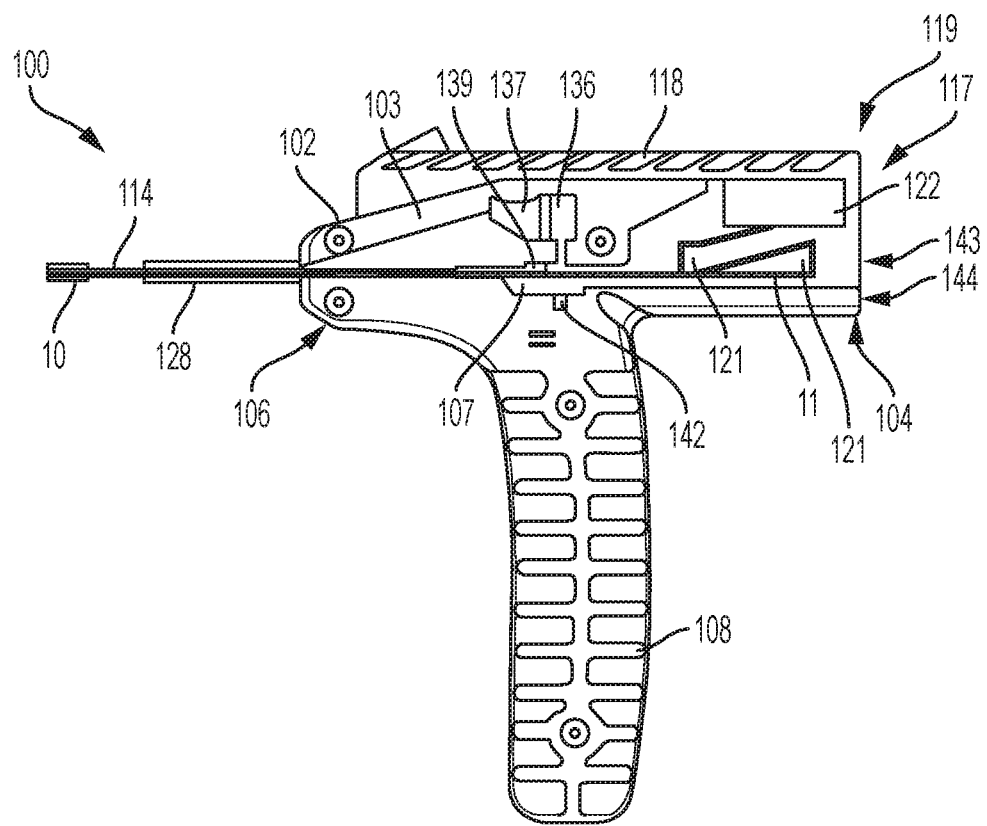
FIG. 14 is a first side view schematic representation of the anchor driver of the multi-barrel drill guide and anchor deployment assembly in the actuated/undeployed configuration according to an embodiment.
Figure 15:
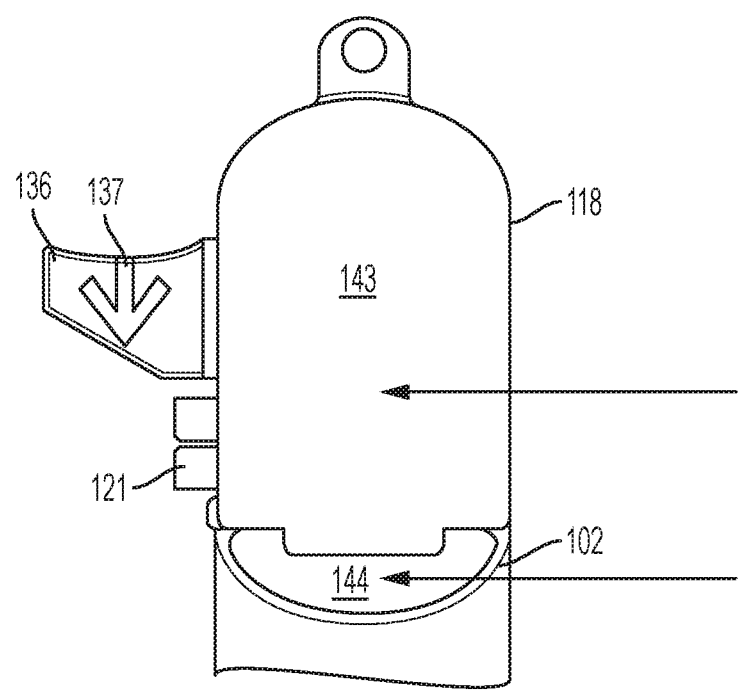
FIG. 15 is a close-up review view schematic representation of the proximal ends of the sliding inserter and elongated body of FIG. 14 according to an embodiment.

Turning now to FIGS. 14-15, there is shown a first side 103 view and close-up rear view schematic representations of the anchor driver 114 of the multi-barrel drill guide and anchor deployment assembly 100 in the actuated/undeployed configuration according to an embodiment. When the flange 139 is rotated out of the path of the track 113, the sliding inserter 118 can advance along the track 113 in the distal direction. As the sliding inserter 118 moves in the distal direction, the anchor driver 114 connected thereto also moves in the distal direction out of the distal tube and guide tip 128, as shown in FIG. 14. The anchor driver 114 (and the sliding inserter 118) are advanced until the suture anchor 10 loaded on the distal end 115 of the anchor driver 114 is fully inserted in the pilot hole. When the sliding inserter 118 is advanced as far as possible, a proximal end surface 143 of the sliding inserter 118 is substantially flush with a proximal end surface 144 of the elongated body 102, as shown in FIG. 15. The substantial alignment of the proximal end surface 143 of the sliding inserter 118 and the proximal end surface 144 of the elongated body 102 provides confirmation to the user that the suture anchor 10 is fully inserted in the pilot hole.

Figure 16:
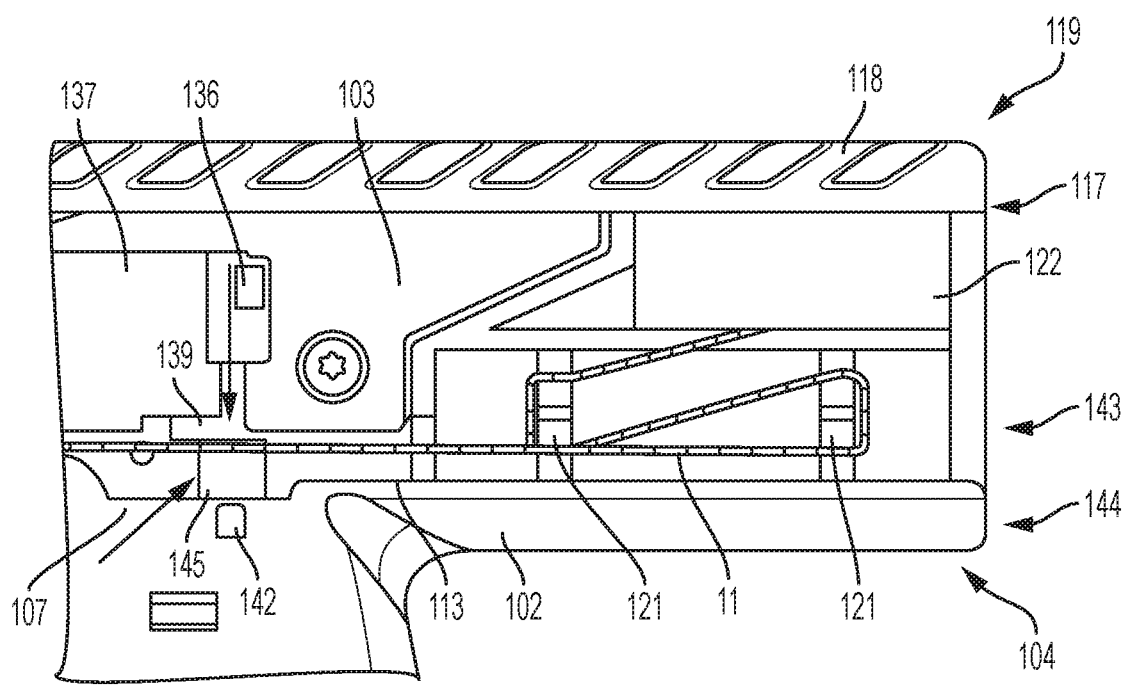
FIG. 16 is a close-up first side view schematic representation of the proximal ends of the sliding inserter and elongated body of FIG. 14 according to an embodiment.

Referring now to FIG. 16, there is shown a close-up first side 103 view schematic representation of the proximal ends 104, 119 of the elongated body 102 and sliding inserter 118 of FIG. 14. In the depicted embodiment, the suture anchor 10 on the distal end 115 of the anchor driver 114 has been fully inserted into the pilot hole. As such, the proximal end surface 143 of the sliding inserter 118 is substantially flush with the proximal end surface 144 of the elongated body 102. As shown in FIG. 16, the portion 140 of the sliding inserter 118 comprises a shallow channel 145. In the actuated/undeployed configuration shown, the shallow channel 145 is substantially aligned with the hinge 138 above the feature 142 on the elongated body 102. When the shallow channel 145 is substantially aligned with the hinge 138 above the feature 142, the user can press or otherwise apply pressure/force downward on the shallow deployment button 136 toward the feature 142 (in the direction of the indicator 141). The shallow deployment button 136 moves downward via the hinge 138 and through the shallow channel 145 toward the feature 142 to deploy the suture anchor 10.

Figure 17:
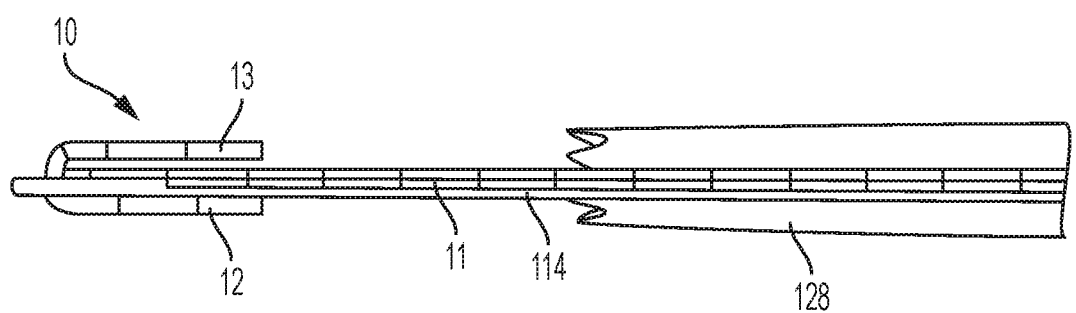
FIG. 17 is a close-up first side view schematic representation of the suture anchor in the undeployed state on the anchor driver of the multi-barrel drill guide and anchor deployment assembly according to an embodiment.

Turning now to FIG. 17, there is shown a close-up first side 103 view schematic representation of the suture anchor 10 in the undeployed state on the anchor driver 114 of the multi-barrel drill guide and anchor deployment assembly 100. In the depicted embodiment, the suture anchor 10 is shown in the undeployed state loaded on the anchor driver 114 (extending from the distal tube or guide tip 128). In the particular embodiment of the suture anchor 10 in FIG. 17, the suture anchor 10 comprises a first arm 12 and a second arm 13 which extend proximally toward the distal tube or guide tip 128 in the undeployed state.

Figure 18:
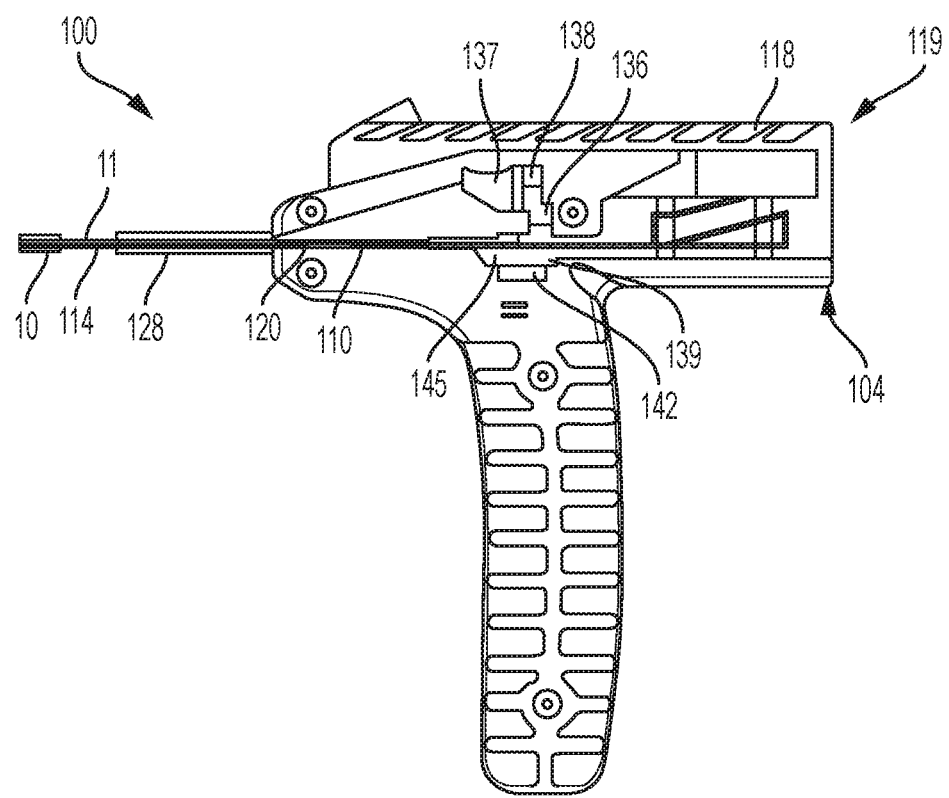
FIG. 18 is a first side view schematic representation of the shallow deployment button of multi-barrel drill guide and anchor deployment assembly in the actuated/deployed configuration according to an embodiment.

Referring now to FIG. 18, there is shown a first side 103 view schematic representation of the shallow deployment button 136 of multi-barrel drill guide and anchor deployment assembly 100 in the actuated/deployed configuration according to an embodiment. After the anchor driver 114 has been fully advanced and the suture anchor 10 has been fully inserted into the pilot hole, the suture anchor 10 must be deployed and then released from the assembly 100. To deploy the suture anchor 10, the user presses or otherwise applies force downward on the shallow deployment button 136 (in its actuated/undeployed configuration), as described above, resulting in the actuated/deployed configuration as shown in FIG. 18.

Figure 19:
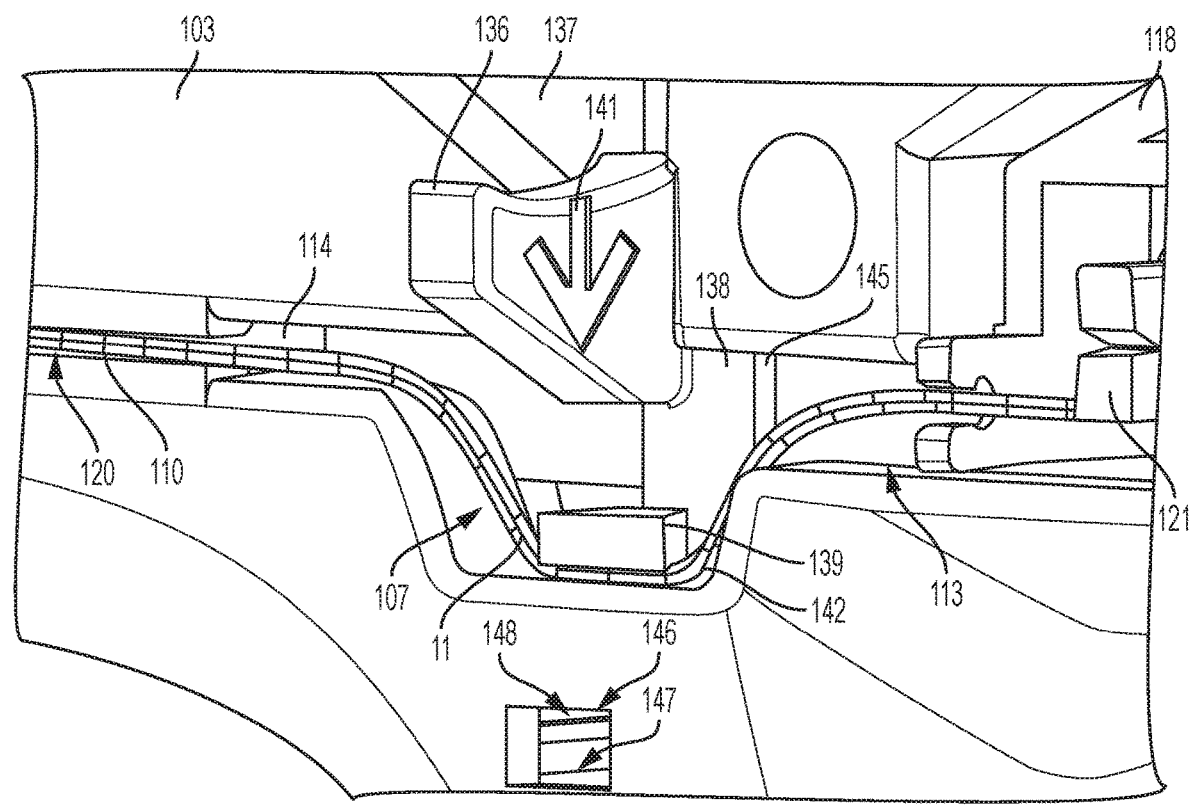
FIG. 19 is a close-up side/rear perspective view schematic representation of the shallow deployment button of FIG. 18 according to an embodiment.

Turning now to FIG. 19, there is shown a close-up side/rear perspective view schematic representation of the shallow deployment button 136 of FIG. 18. When the shallow deployment button 136 is pressed downward through the shallow channel 145 toward the feature 142 of the elongated body 102, the flange 139 presses or otherwise displaces the passing filament 11 toward the feature 142, creating a new, longer path for the passing filament 11. In the depicted embodiment, the assembly 100 has an additional indicator window 146 formed in the handle 108 (and/or in the elongated body 102). The indicator window 146 comprises a shallow deployment clicker 147 and a ridge 148. The shallow deployment button 136 is connected to the shallow deployment clicker 147 such that when the shallow deployment button 136 is pressed downward to the actuated/ deployed configuration, the shallow deployment clicker 147 deflects over the ridge 148 in the indicator window 146, which is visible to the user. In an additional embodiment, movement of the shallow deployment clicker 147 over the ridge 148 in the indicator window 146 causes an audible noise (e.g., click), providing an additional indication to the user that the shallow deployment button 136 is in the actuated/deployed configuration and the suture anchor 10 has reached the deployed state.

Figure 20:
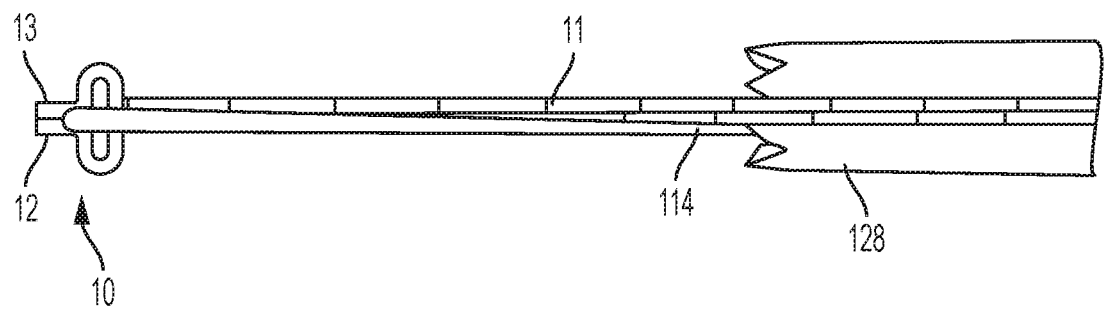
FIG. 20 is a close-up first side view schematic representation of the suture anchor in the deployed state on the anchor driver of the multi-barrel drill guide and anchor deployment assembly according to an embodiment.

Referring now to FIG. 20, there is shown a close-up first side 103 view schematic representation of the suture anchor 10 in the deployed state on the distal end 115 of the anchor driver 114 of the multi-barrel drill guide and anchor deployment assembly 100. From the undeployed state (shown in FIG. 17), actuation and deployment of the shallow deployment button 136 displaces the path of passing filament 11, effectively removing slack and pulling the passing filament 11 in the proximal direction. When the passing filament 11 is pulled in the proximal direction, the first arm 12 and the second arm 13 of the suture anchor 10 rotate in the distal direction toward each other (as the anchor is prevented from being pulled proximally by a force imparted in the opposite direction by the distal end of the anchor driver), as shown in FIG. 20 (and described below with reference to FIGS. 22-29). This causes the suture anchor 10 to fold itself further into the pilot hole and create a wedge which is wider than the drill diameter and locks the suture anchor 10 into place.

Figure 21:
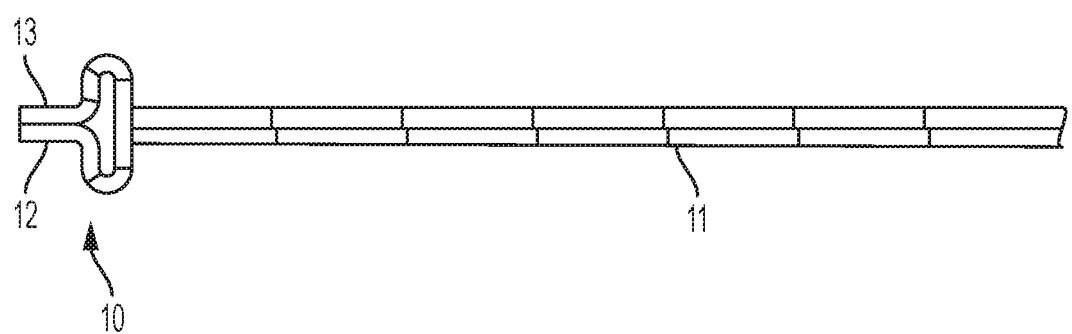
FIG. 21 is a close-up side view schematic representation of the suture anchor of FIG. 20 with the multi-barrel drill guide and anchor deployment assembly removed according to an embodiment.
Figure 22:
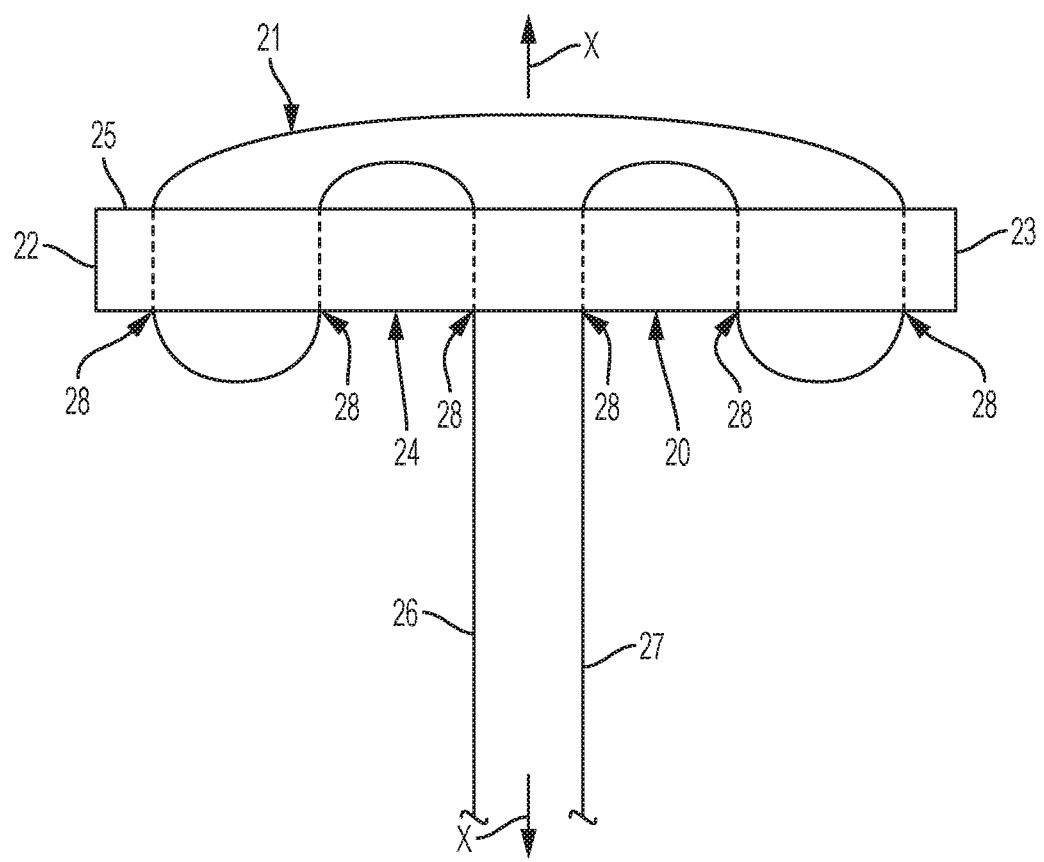
FIG. 22 is a side view schematic representation of an embodiment of the suture anchor in the undeployed configuration according to an embodiment.

Turning now to FIG. 21, there is shown a close-up first side 103 view schematic representation of the suture anchor 10 of FIG. 20 with the multi-barrel drill guide and anchor deployment assembly 100 removed. In the deployed state, as shown in FIGS. 20-21, the suture anchor 10 is removed from the assembly 100 by unwrapping or otherwise dislodging the passing filament 11 from the one or more notches 121 and the flexible block 122 at the proximal end 119 of the sliding inserter 118.

Referring now to FIGS. 22-29, there are shown various views schematic representations of an embodiment wherein the suture anchor 10 is a shallow Y-Knot®. One such suture anchor is disclosed in U.S. patent application Ser. No. 15/687,040 assigned to the assignee hereof and incorporated by reference herein in its entirety. The suture anchor 10 of the shallow Y-Knot® embodiment illustrated in FIGS. 22-29 is a fibrous construct (anchor body) 20 having at least one passing filament 21 weaved therethrough. The fibrous construct 20 has a first arm 22 and a second arm 23 (as the first and second arms 12, 13 shown in FIG. 17) with a proximal side 24 and a distal side 25 extending therebetween. The passing filament 21 has a first end 26 and a second end 27 woven through the fibrous construct 20 in a T-shape in the undeployed (or pre-deployment) configuration. Importantly, the fibrous construct 20 is thicker than the passing filament 21, providing greater tensile strength to the fibrous construct 20 (as compared to the filament 21) to minimize creep toward the top/proximal end of the pilot hole. If more tension is placed on the passing filament 21, the fibrous construct 20 is configured to and will widen and wedge into the bottom of the pilot hole to lock in place (based on the particular placement of the passing filament 21 through the fibrous construct 20, the force and location thereof imparted by the deployment device (e.g., anchor driver 114) on the fibrous construct 20, and the characteristics of the fibrous construct 20 itself).

Figure 23:
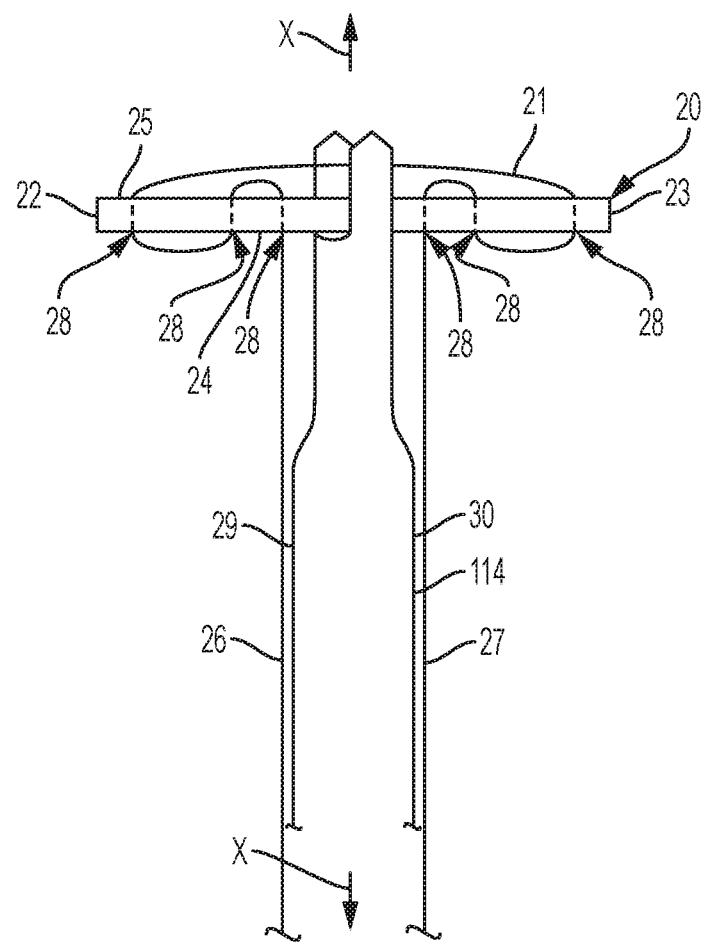
FIG. 23 is a side view schematic representation of the suture anchor of FIG. 22 loaded onto the anchor drive according to an embodiment r.

FIG. 23 shows one embodiment for passing locations 28 on the fibrous construct 20. As shown, the passing filament 21 enters and exits the proximal side 24 and distal side 25 of the fibrous construct 20 at a plurality of passing locations 28. The fibrous construct 20 is then loaded onto an anchor deployment device/inserter, such as the anchor driver 114 described above. Importantly, the fibrous construct 20 is positioned within the anchor driver 114 such that the first end 26 of the filament 21 extends along a first side 29 of the anchor driver 114 and second end 27 of the filament 21 extends along a second side 30 of the anchor driver 114.

Figure 24:
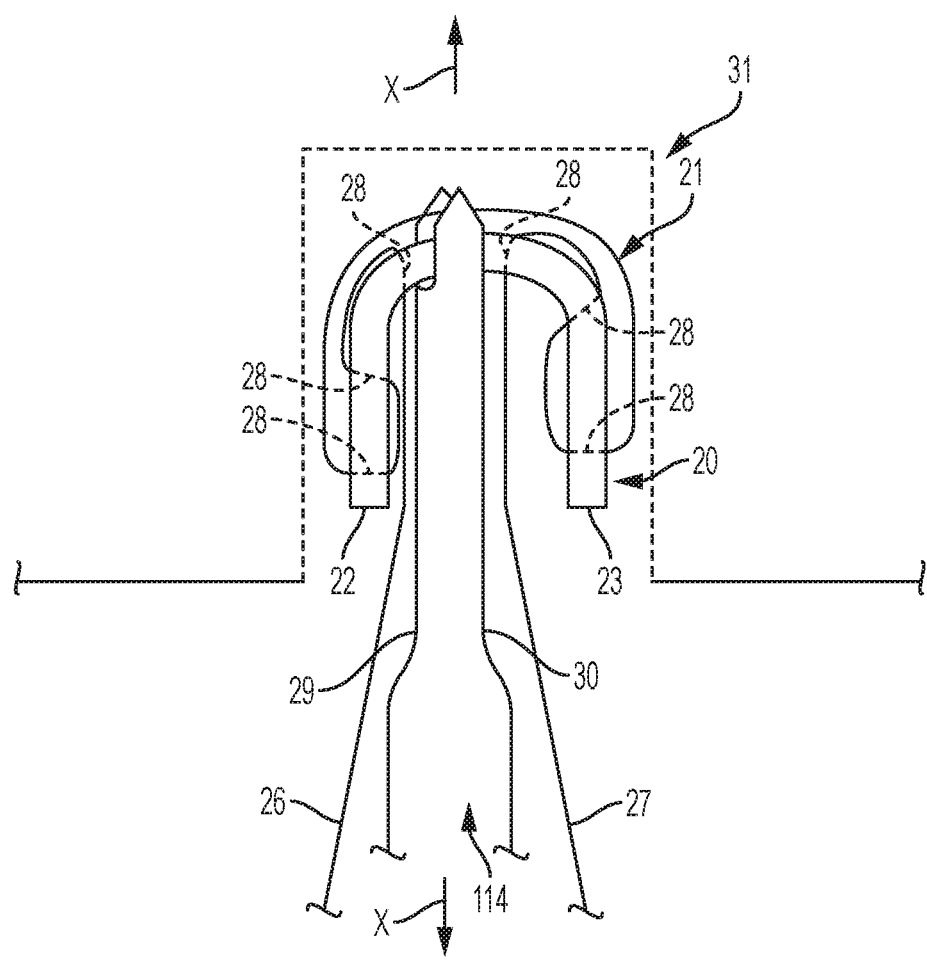
FIG. 24 is a side view schematic representation of the suture anchor of FIG. 22 loaded onto the anchor driver and placed in a pilot hole according to an embodiment.

Deployment of the fibrous construct 20 is further described and illustrated with reference to FIGS. 24-29. As shown in FIG. 24, the fibrous construct 20 is implanted by the anchor driver 114 into a preformed pilot hole 31. Once the fibrous construct 20 is loaded onto the anchor driver 114 (or other deployment device), the anchor driver 114 is used to push the fibrous construct 20 into a narrow preformed pilot hole 31 (e.g., 10 mm deep). Such a narrow pilot hole 31 is often formed in smaller bones by necessity, such as those in extremities.

Figure 25:
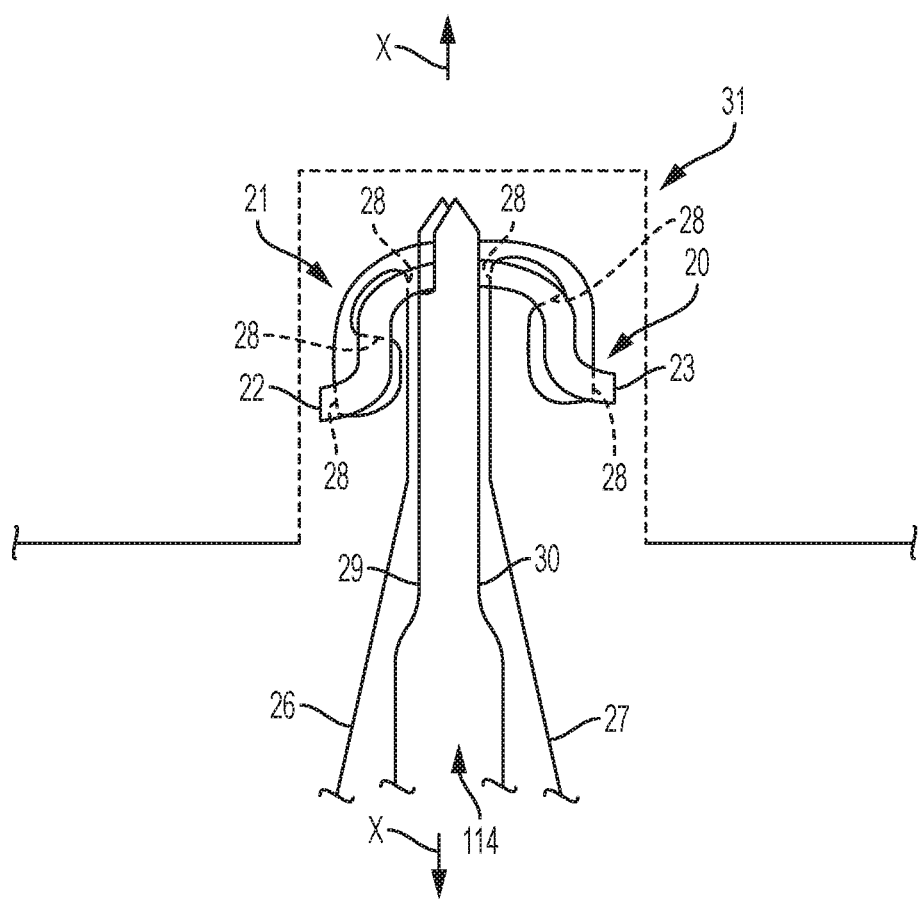
FIG. 25 is a side view schematic representation of the suture anchor of FIG. 22 between the undeployed and deployed configurations according to an embodiment.

When the fibrous construct 20 enters the narrow pilot hole 31, the first arm 22 and second arm 23 of the fibrous construct 20 begin to fold or otherwise bend in the proximal direction the narrow width of the pilot hole 31, as shown in FIG. 24 (also shown in FIG. 17). Then, to deploy the fibrous construct 20, the anchor driver 114 is held in place, fully inserted in the pilot hole 31, while the first and second ends 26, 27 of the passing filament 21 are tensioned and pulled away from the fibrous construct 20 in the proximal direction. When the first and second ends 26, 27 of the passing filament 21 are pulled, lengths of fibrous construct 20 between each of the passing locations 28 are pulled closer together as slack in the passing filament 21 between the passing locations 28 is minimized. Meanwhile, as a result, the first arm 22 and the second arm 23 of the fibrous construct 20 begin to rotate in the distal direction, as shown in FIG. 25.

Figure 26:
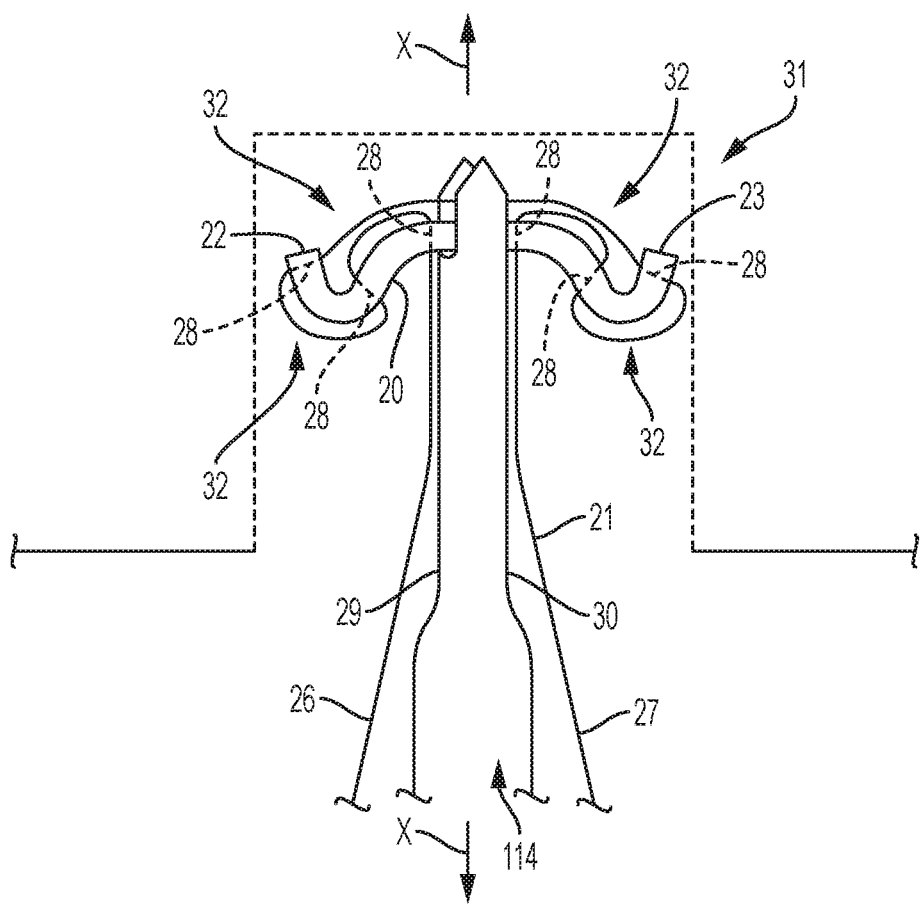
FIG. 26 is another side view schematic representation of the suture anchor of FIG. 22 between the undeployed and deployed configurations according to an embodiment.
Figure 27:
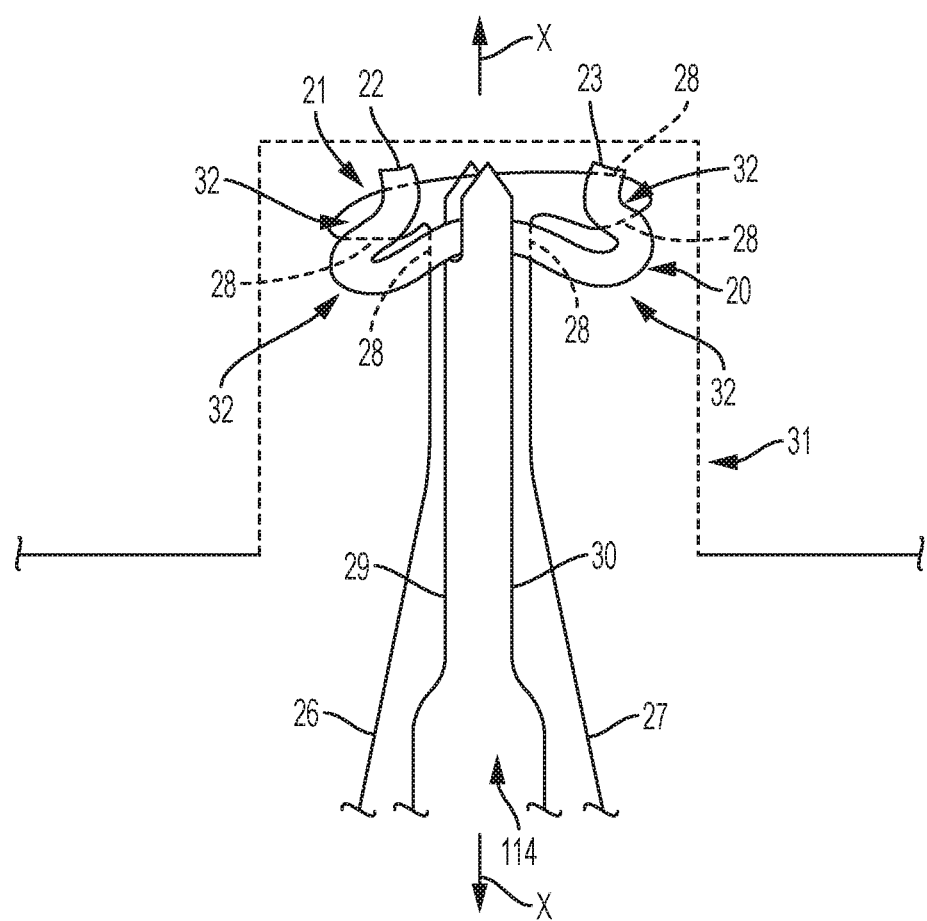
FIG. 27 is a final side view schematic representation of the suture anchor of FIG. 22 between the undeployed and deployed configurations according to an embodiment.
Figure 28:
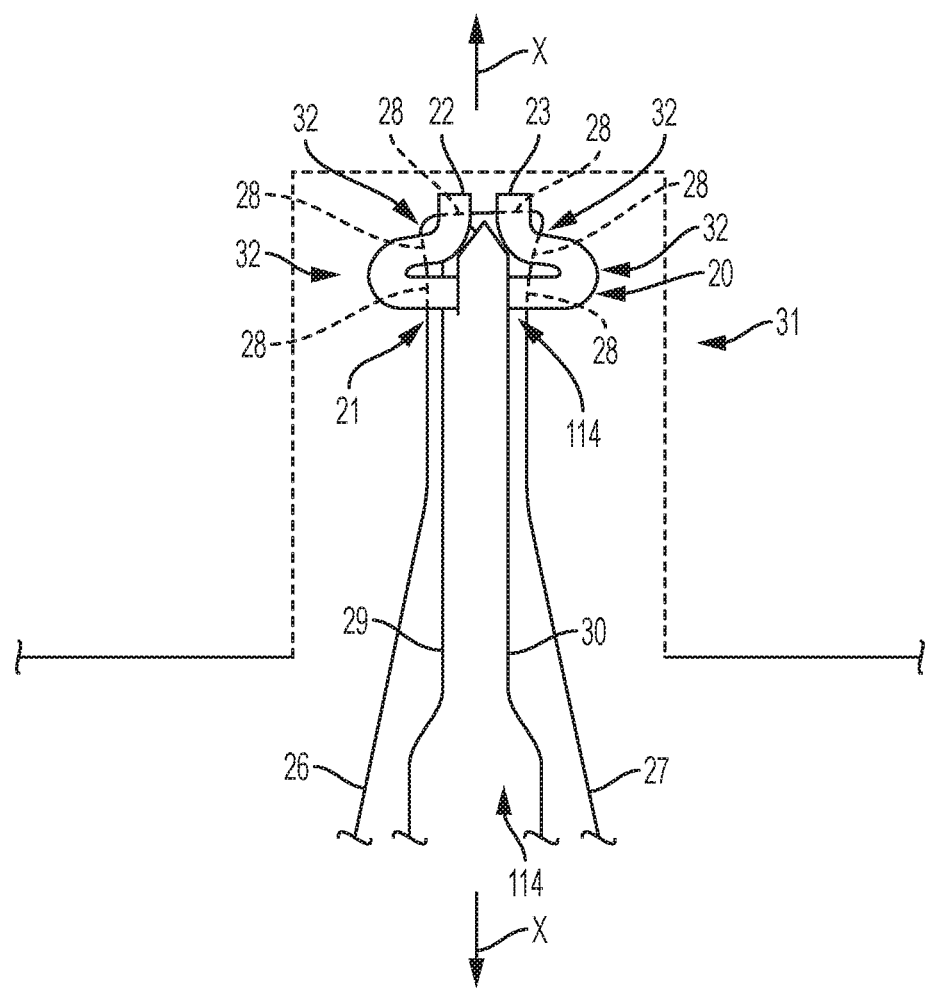
FIG. 28 is a side view schematic representation of the suture anchor of FIG. 22 in the deployed configuration according to an embodiment.

To continue deployment of the fibrous construct 20, the first and second ends 26, 27 of the passing filament 21 are pulled farther and farther in the proximal direction away from the fibrous construct 20 and additional slack of the passing filament 21 between the passing locations 28 in the fibrous construct 20 is reduced. As a result, the first and second arms 22, 23 of the fibrous construct 20 continue to fold or otherwise bend tighter in the distal direction, as shown in FIGS. 26-27, and pleats 32 begin to form between adjacent passing locations 28. Due to the added tension, the first and second arms 22, 23 of the fibrous construct 20 are pulled closer together toward the central longitudinal axis x-x through the fibrous construct 20. As an additional result, the pleats 32 become more defined, as shown in FIG. 28.

Thereafter, the first and second ends 26, 27 of the passing filament 21 are pulled until there is no remaining slack between adjacent passing locations 28 in the fibrous construct 20, as shown in FIG. 29 (and FIG. 21). Applying additional tension to the first and second ends 26, 27 of the passing filament 21 strengthens the fibrous construct 20 by forcing the fibrous construct 20 to widen or expand inside the pilot hole 31 until it reaches a fully deployed configuration, as shown in FIG. 29. As the fibrous construct 20 is compressed or gets shorter, the fibrous construct 20 expands in directions perpendicular to its length (i.e., width or thickness) to set and secure the anchor in place in the pilot hole 31.

The pleats 32 form a stack of the mattress thicknesses effectively increasing a diameter (as measured in relation to the central longitudinal axis x-x of the fibrous construct 20 and the pilot hole 31). This relative increase in size in distance from the central longitudinal axis x-x of the pilot hole 31 creates a retention force of the fibrous construct 20, including the expansion in width and/or thickness described above. In other words, Poisson's ratio of width and/or mattress thickness growth during a reduction in length provides for an increase in deployment size that is additive to the increase due to the pleats 32 force of the fibrous construct 20. Poisson's ratio defines the proportional decrease in a longitudinal measurement to the proportional increase in length in a sample of material that is elastically stretched. Therefore, if a material is compressed in the x-direction, for example, the material will expand in the y-direction and/or z-direction.

The passing filament 21 can be removed from the fibrous construct 20 by pulling either end 26, 27 until the entire passing filament 21 is removed. The final form of the fibrous construct 20 in the deployed state allows the passing filament 21 to easily slide therethrough, as the fibrous construct 20 is set and secured in the pilot hole 31. That is, the tensile strength of the fibrous construct 20 in this configuration is sufficient to keep the fibrous construct 20 in place while the passing filament 21 is easily removed.

Deployment of the fibrous construct 20 is further described and illustrated with reference to FIGS. 29A-29C, in accordance with an alternative embodiment. FIG. 29A shows the fibrous construct 20 in a similar undeployed position as the fibrous construct 20 in FIG. 24. FIG. 29B shows the fibrous construct 20 in a position about half way to full deployment, and FIG. 29C shows the fibrous construct 20 in a fully deployed configuration. The main difference between the embodiments shown in FIGS. 24-29 and the embodiments shown in 29A-29C, includes the slack line that runs across the side of the inserter 114 (no. "21" written on the line) in FIG. 29A, for example, where the slack line runs across the distal end and partially inside the forked section of the inserter 114 in FIG. 24. Other positioning configurations of the passing filament 21 through the fibrous construct 20, which allow the fibrous construct to perform the same or similar functionality are contemplated and within the scope of this disclosure (as should be appreciated by a person of ordinary skill in the art in conjunction with a review of this disclosure).

Turning now to FIGS. 30-36, there are shown various views schematic representations of an embodiment of the multi-barrel drill guide and anchor deployment assembly 100 wherein the suture anchor 10 is a Y-Knot® anchor 40, for example, which can be any all suture anchor configured to perform the same functionality as described herein (as should be understood by a person of ordinary skill in the art in conjunction with a review of this disclosure). FIG. 30 shows the assembly 100 with a 1.3 mm or 1.8 mm Y-Knot® all suture anchor. One such suture anchor is disclosed in U.S. Pat. No. 9,826,971 assigned to the assignee hereof and incorporated by reference herein in its entirety. In the depicted embodiment and as described above, the drill bit 116 is loaded in the second channel 112 into the convergence area 130 such that the drill bit 116 acts as the locking mechanism 133 to ensure that the sliding inserter 118 will not move in transportation or during handling until the drill bit 116 is used and removed. In the depicted embodiment of the assembly 100 shown in FIG. 30, in addition to having a different all suture anchor, the assembly 100 does not have the shallow deployment button 136 or shallow deployment clicker 147 of the embodiment of the assembly 100 of FIGS. 1-22. Otherwise, the assembly 100 is the same as the assembly 100 described and illustrated with respect to FIGS. 1-20.

FIG. 31 shows the drill bit 116 after it has drilled the proper depth for a pilot hole in a bone. As with other embodiments of the assembly 100, the user will know the proper depth has been reached because the depth stop 126 on the drill bit 116 will contact the opening 123 of the sliding inserter 118. FIG. 32 shows the assembly 100 after the drill bit 116 has been removed. The sliding inserter 118 is now free to be advance along the track 113 and insert the Y-Knot® 40 into a pilot hole. FIG. 33 shows the assembly 100 after the all suture anchor 40 is fully inserted into the pilot hole and deployed, while FIG. 34 shows the all suture anchor 40 deployed after the assembly 100 is removed.

An embodiment of the Y-Knot® anchor (or soft anchor or "all-suture" anchor) 40 is illustrated in detail in FIGS. 35-36. The all suture anchor 40, as shown in FIGS. 35-36, contains at least two sections: at least one filament 41, which is a suture to be anchored; and a fibrous construct (anchor body) 40, which is to form a portion of the anchor that can increase in width, thickness and/or diameter and shrink in length as part of deployment. See FIG. 35, showing the fibrous construct 40 in the undeployed state; and FIG. 36, showing the fibrous construct 40 "shortened" and "expanded" in the deployed state, which is additive to the increase due to the pleats). This soft anchor embodiment also takes advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the fibrous construct 40 that increases in width, thickness and/or diameter at deployment, it should be understood that the filament 41 also plays a role in the deployment of the anchor even though the filament 41 may remain free (in some embodiments) to slide, and non-slidable in others (at least at a particular position or point in use) in relation to the fibrous construct 40. The filament 41 helps to position, align and support the fibrous construct 40, such that if the filament 41 were to be removed from the fibrous construct 40 after deployment of the anchor, the fibrous construct 40 may be free to spill (i.e., release), allowing the fibrous construct 40 to collapse and shrink in size, allowing for easy (and potentially undesirable) removal.

In other words, the fibrous construct 40 has two primary functions. First, it becomes a base for the filament 41 to slide within. Second, when compressed and/or pleated during deployment, the fibrous construct 40 becomes more compact in one direction thereby expanding outwardly and increasing its overall width, thickness or diameter to create a retention capacity. This action of having the fibrous construct 40 change in shape to increase its overall width, thickness or diameter is a useful characteristic which may be used advantageously to secure the anchor in a hole or against a bony or soft tissue. It is this combination of the expanding fibrous construct 40 coupled with the filament 41 remaining slidable (in some embodiments; and non-slidable in others, at least at a particular position or point in use) in relation to the fibrous construct 40 that render embodiments of the present invention ideal for the reattachment of soft tissue to bone or soft tissue to soft tissue where it is desirable to pass sliding knots to secure a repair.

The discussion below relates to alternative embodiments of a disposable drill, and of two different anchor drivers.

Turning to FIG. 37, a side view schematic representation of a disposable drill 300 with a pre-installed drill bit 302 according to an alternative embodiment is shown. This disposable drill 300 and pre-installed drill bit 302 may be used in place of drill bit 116, described above, or separately/ independently therefrom. The disposable drill can include, but is not limited to, a motor 301, a drill bit 302 attached to the motor with a specified/predetermined length so that it is configured to create an pilot hole with a desired length/depth for a particular procedure, disposable batteries 303 configured to supply power to the motor, and at least one switch 304 configured to be actuated (rotationally, linearly, perpendicular to the longitudinal axis of the device ("pushed")) by a user to turn on the drill bit 302, and/or set the desired speed of the drill bit 302. The disposable drill 300 can also include a disposable plastic housing 305 to make the device lightweight, less expensive, and disposable. The disposable plastic housing 305 can be made from any plastic or combination of plastics.

As discussed above, during suture anchor placement, a pilot hole is typically made in bone before an anchor is inserted. The pilot hole is typically formed by using a drill bit to drill a hole for placement of the anchor. However, conventionally, a drill handpiece and battery must be sterilized and ready for use in the surgery. Also, a drill bit is typically drilled a certain depth through a drill guide, so a hard stop structure can be required on the drill guide, or a hard stop structure can be placed on the drill handpiece at a certain location to create an appropriate hard stop against the drill guide (as should be understood by a person of ordinary skill in the art in conjunction with a review of this disclosure).

By providing disposable drill 300 in accordance with an embodiment, there is no need for an additional drill handpiece and battery to be sterilized before the surgery. Also with the drill bit 302 pre-installed on the disposable drill 200, the disposable drill 300 is ready to use out of the package and does not require the additional step of installing of the drill bit on the drill handpiece.

Generally, the following described and illustrated two alternative driver designs are configured to work based on the same concept of pulling suture tails back/proximally from an anchor to deploy the anchor (see, e.g., FIGS. 18-21 and related description). The alternative driver designs may be used in place of the anchor driver 114, described above, or separately/independently therefrom. Each of the following described and illustrated anchor driver devices works with an all suture soft tissue fixation device with a suture that is configured to slide after the anchor is deployed. In many procedures that involve soft tissue fixation in the extremities, it is necessary to have an anchor that can be deployed in a relatively shallow hole with a narrow diameter (as compared with other locations in the body). The uniqueness of the all suture soft tissue fixation device pertains, in part, to the weaving of the suture through the anchor which allows the anchor to sufficiently deploy in the bone tunnel (preferably at the bottom of the bone tunnel) while the driver is still inserted. The pattern which the suture is weaved through the anchor is unique in that it preferably does not start and end at the tips of the anchor (although, it can do so). Instead, it is started very close to the center and woven to the tip at one end then from there to the opposite tip and woven back to the center next to the starting position. Such a configuration is illustrated in the FIG. 38. As shown, the all suture soft tissue fixation device includes a fibrous construct (anchor body) 20 (e.g., no. 5 suture) having at least one passing filament 21 (e.g., no. 0 suture) weaved therethrough, similar to the suture anchor 10 of the shallow Y-Knot® embodiment illustrated in and described with respect to FIGS. 22-29. The weaving of the suture/filament 21 through the fibrous construct 20 allows the anchor to deploy while still on a driver by tensioning the first and second ends 26, 27 of the passing filament 21 (similarly to FIGS. 18-21, 25-29, as described above, and below). The design of the driver allows insertion of the anchor into the bone tunnel without use of an additional guide, and deploys the anchor quickly by an actuation means (e.g., by squeezing or depressing of a lever). After deploying the anchor, the driver can be removed and the suture can slide through the anchor. FIGS. 39-56 illustrate one alternative embodiment of an anchor driver 200, and FIGS. 57-62 illustrate another alternative embodiment of an anchor driver 400.

Turning to FIG. 39, there is shown a side perspective view of an alternative embodiment of an anchor driver 200. The anchor driver 200 can include, but is not limited to, a forked distal driver tip 201 to position a suture anchor 10 in a bone hole (not shown). A depth stop 202 is positioned proximally of the forked distal driver tip 201, and is configured to ensure that the driver is inserted a predetermined depth into the bone hole (e.g., 10 mm). A lever arm 203 is shown, which is configured to displace suture attached to the anchor 10 in order to deploy the anchor 10 (described below). A spool retaining arm 206 is also shown, and is configured to keep a suture spool 205 (detailed below) in a locked position until the spool 205 is intentionally released by a user. The anchor driver 200 can include a housing/cover (not shown) to cover the internal parts. The anchor driver 200 is shown open without a housing/cover to allow for illustration of the internal parts.

Turning to FIG. 40, a slot 207 is provided in the anchor driver 200 in which spool 205 sits. The slot 207 includes teeth 207A configured to engage and lock with teeth 205A of the spool (FIG. 41) when the spool 205 is fully inserted into a locked position (described below). The spool retaining arm 206 is also configured to engage and lock with teeth 205A of the spool (FIG. 41) when the spool 205 is fully inserted into a locked position. A perspective view of the spool 205 is shown in FIG. 41, and includes portions to wind suture 205B, 205C, and teeth 205A.

Referring to FIGS. 42 and 43, perspective views of the safety bar 204 alone and positioned within the anchor driver 200, respectively, are shown. As shown in FIG. 43, the anchor driver 200 is fully assembled (except for an optional housing/cover), and the spool 205 is shown in the locked position where the lateral surface 208 is positioned out a predetermined distance from the side 209 of the anchor driver 200. In the locked position, a portion of teeth 207A of the slot 207 is positioned in contacting relation with a portion of teeth 205A of the spool 205, and the spool retaining arm 206 is positioned between another portion of teeth 205A of the spool 205. In addition, the safety bar 204 is shown positioned is a slot of the anchor driver 200 under the lever arm 203 (which is configured to block the lever arm from contacting the suture limbs 26 and 27). The anchor 10 is also shown positioned on the forked distal driver tip 201.

FIG. 44 is a top perspective view of the distal end of the anchor driver 200 showing the anchor 10 positioned on the forked distal driver tip 201 (in an undeployed configuration/position) and ready for insertion into a bone hole.

FIG. 45 is a side perspective view of the spool 205 in the locked position (as described above). As shown, the lateral surface 208 is positioned out a predetermined distance from the side 209 of the anchor driver 200 to form a spool release button.

FIG. 46 is a side perspective view of the spool 205 in the unlocked/released position, where the lateral surface 208 has been pushed/actuated by a user to be substantially flush with the side 209 of the anchor driver 200. This position of the spool 205 releases the teeth 205A of the spool 205 from the teeth 207A of the slot 207 and from the spool retaining arm 206, allowing the spool 205 to freely spin and unwind the suture.

A method of using anchor driver 200 will now be described. In brief, the anchor driver 200 is preferably configured to be a single use device, and is packaged as shown in FIG. 47 (showing a side perspective view of anchor driver 200 in an undeployed configuration). After drilling a bone hole/tunnel (e.g., a 10 mm deep and 1.5 mm diameter hole), anchor driver 200 is then inserted into the bone tunnel by striking the back of the driver (as should be understood by a person of skill in the art in conjunction with a review of this disclosure). When the built in depth stop 202 is flush with the top surface of the bone, the safety bar 204 can be removed and the lever arm 203 is squeezed to deploy the anchor 10 (see FIGS. 48-54). After the anchor 10 is deployed, the lateral surface 208 of the spool 205 is pushed in to be flush with the side surface 209 of the driver body, and the driver 200 is removed from the insertion site (FIG. 55). By removing the driver 200 while holding the spool 205 in the released position, the suture tails 26, 27 will unspool and free themselves from the driver (FIG. 56).

Turning to FIG. 48, the safety bar 204 is shown removed (after the anchor 10 is preferably fully inserted into a bone hole) to allow deployment of the anchor 10.

Referring to FIG. 49, the lever arm 203 is actuated/pressed down by a user (similar to the embodiment shown and described with respect to FIGS. 18-21), which deflects the suture tails 26, 27 (only from the anchor/distal side and not the spool proximal side because of the spool being in the locked position) to deploy the anchor 10.

Turning to FIG. 50, the tails of the anchor 10 are shown beginning to flip and point in the opposite/distal direction, as the suture 21 slack is taken out of the anchor by depressing the lever arm 203.

Turning to FIGS. 51 and 52, the lever arm 203 is shown being depressed about half way over the suture limbs 26, 27, further deploying the anchor 10.

Turning to FIGS. 53 and 54, the lever arm 203 is shown fully depressed over the suture limbs 26, 27, fully deploying the anchor 10 (preferably at the base of the bone hole).

Turning to FIG. 55, the lateral surface 208 of the spool 205 is shown pushed in to be flush with the side surface 209 of the driver body, and the driver 200 is removed from the insertion site which unspools the suture.

Referring to FIG. 56, the anchor 10 is shown in its fully deployed state (preferably at the bottom of a bone hole) after the anchor driver 200 is removed.

Turning to FIG. 57, there is shown a side perspective view of an alternative embodiment of an anchor driver 400. The anchor driver 400 can include, but is not limited to, a forked distal driver tip 401 to position a suture anchor 10 in a bone hole (not shown). A depth stop 402 is positioned proximally of the forked distal driver tip 401, and is configured to ensure that the driver is inserted a predetermined depth into the bone hole (e.g., 10 mm). A lever arm 403 is shown, which is configured to displace suture attached to the anchor 10 in order to deploy the anchor 10 by pushing a sliding cleat 405 attached to the proximal end of the suture tails 26, 27 proximally through a channel or groove 407 (further described below). A safety lever 404 is also shown, and is configured to prevent the actuation of the lever arm 403 until when appropriate. A cleat release notch 406 is also shown, which is configured to stop the cleat 405 from freely falling out of the anchor driver 400 after the anchor 10 is deployed. As shown in FIG. 58, the anchor driver 400 can also include a housing/cover 408 to cover the internal parts (although, the anchor driver 400 is shown open without a housing/cover in many of these figures to allow for illustration of the internal parts).

As shown in additional figures identified below, the lever arm 403 is configured to push the sliding cleat 405 back/proximally a predetermined distance (e.g., about 10 mm, which is an example appropriate distance to deploy the anchor 10). After pushing the cleat 405 proximally a predetermined distance, the lever arm 403 is configured to be positioned fully outside the channel 407 of the sliding cleat 405. Because of this, the sliding cleat 405 is configured to freely slide up to the cleat release notch 406 at the distal end of the driver 400. At this point, the driver 400 can be removed from the insertion site and the cleat 405 can be separated from the driver 400 with a pull on the suture tails 26, 27.

A method of using anchor driver 400 will now be described. In brief, the anchor driver 400 is preferably configured to be a single use device, and is packaged as shown in FIG. 58 (showing a side perspective view of anchor driver 200 in an undeployed configuration). After drilling a bone hole/tunnel (e.g., a 10 mm deep and 1.5 mm diameter hole), anchor driver 400 is then inserted into the bone tunnel by striking the back of the driver (as should be understood by a person of skill in the art in conjunction with a review of this disclosure). When the built in depth stop 402 is flush with the top surface of the bone, the lever arm 403 can be actuated by a user (e.g., squeezed) which pushes the sliding cleat 405 proximally to tension the suture tails 26, 27 and deploy the anchor (see FIG. 60). With the lever arm 403 fully depressed, the driver 400 can be removed from the insertion site and the sliding cleat 405 is configured to pull out from the front of the driver (see FIGS. 61, 62). Finally, the suture can be uncleated from the sliding cleat 405 and the suture tails can be pulled to ensure that the anchor is deployed.

Turning to FIG. 59, the anchor driver 400 is shown in an undeployed/unactuated position, and is ready to deploy the anchor 10 into a bone hole (not shown).

Referring to FIG. 60, the anchor driver 400 is shown after the lever arm 403 has been actuated making it clear of the channel 407, and the anchor 10 has been deployed.

Referring to FIG. 61, the sliding cleat 405 is shown positioned at the release notch 406, having moved through the channel 407 after the driver 400 has been removed from the insertion site.

Turning to FIG. 62, the sliding cleat 205 is shown completely removed from the driver 400 and is ready to be uncleated to the anchor 10 through the suture tails 26, 27.

Filaments and sutures, as the terms are used and described herein, includes braided (i.e., multi-filament) suture and monofilament suture as well as any other metallic or non-metallic filamentary or wire-like material suitable for performing the function of a suture. This material can include both absorbable and non-absorbable materials.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A multi-barrel drill guide, comprising:
an elongated body extending along a longitudinal axis having a proximal end and a distal end with a handle extending from the elongated body between the proximal end and the distal end;
an elongated distal guide tube attached to and extending distally from the distal end of the elongated body;
a sliding inserter movably connected to the elongated body such that the sliding inserter is configured to move between the proximal end and the distal end of the elongated body;
a first channel extending from the proximal end to the distal end of the elongated body;
a second channel extending from the distal end to a position between the distal end and the proximal end along the elongated body, the second channel extending at an angle relative to the first channel; and
a convergence area at the distal end where the first channel and the second channel intersect.

2. The multi-barrel drill guide of claim 1, further comprising a locking mechanism configured to selectively lock the sliding inserter in place with respect to the elongated body.

3. The multi-barrel drill guide of claim 2, wherein the elongated body comprises an opening in the elongated body, and wherein the locking mechanism comprises an opening in the sliding inserter selectively aligned with the opening in the elongated body extending to the second channel.

4. The multi-barrel drill guide of claim 1, wherein the convergence area extends to a single exit point.

5. The multi-barrel drill guide of claim 4, wherein the single exit point is at a distal end of the elongated distal guide tube.

6. The drill guide of claim 1, further comprising a first portion of the second channel which extends at an angle relative to the longitudinal axis different from a second and different portion of the second channel.

7. The multi-barrel drill guide system of claim 1, wherein the second channel curves in a direction away the handle.

8. The multi-barrel drill guide of claim 1, wherein the elongated body includes an exterior portion and wherein the exterior portion comprises a slit extending into the first channel.

9. A multi-barrel drill guide system, comprising:
an elongated body extending along a longitudinal axis having a proximal end and a distal end with a handle extending from the elongated body between the proximal end and the distal end;
an elongated distal guide tube attached to and extending distally from the distal end of the elongated body;
a sliding inserter movably connected to the elongated body such that the sliding inserter is configured to move between the proximal end and the distal end of the elongated body;
a first channel extending from the proximal end to the distal end;
a second channel extending from the distal end to a position between the distal end and the proximal end along the elongated body, the second channel at an angle relative to the first channel; and
a suture anchor fully positioned within and movable in a slidable manner within the first channel; and
a drill bit movable in a slidable manner within the second channel.

10. The multi-barrel drill guide system of claim 9, wherein the suture anchor is loaded onto a driver, which is movable in a slidable manner within the first channel.

11. The multi-barrel drill guide system of claim 9, further comprising a locking mechanism configured to selectively lock the sliding inserter in place with respect to the elongated body.

12. The multi-barrel drill guide system of claim 11, wherein the elongated body comprises an opening in the elongated body, and wherein the locking mechanism comprises an opening in the sliding inserter selectively aligned with the opening in the elongated body extending to the second channel.

13. The multi-barrel drill guide system of claim 12, wherein in a locked position, the drill bit extends through the opening of the sliding inserter and the opening in the elongated body into the second channel.

14. The multi-barrel drill guide system of claim 10, wherein the elongated body comprises a recess on the elongated body and wherein the multi-barrel drill guide system further comprises a shallow deployment button hingedly connected within the recess on the elongated body.

15. The multi-barrel drill guide system of claim 14, wherein the driver is connected to the sliding inserter and sliding the driver distally along the first channel rotates the shallow deployment button away from the recess.

16. The multi-barrel drill guide system of claim 9, further comprising a bent portion of the second channel which extends at an angle relative to the longitudinal axis different from a remainder of the second channel.

17. The multi-barrel drill guide system of claim 9, wherein the second channel curves in a direction away the handle.

18. A method of drilling a pilot hole and inserting a suture anchor, the method comprising the steps of:
providing a multi-barrel drill guide and anchor deployment assembly with an elongated body extending along a longitudinal axis having a proximal end and a distal end with a handle extending from the elongated body between the proximal end and the distal end, and an elongated distal guide tube attached to and extending distally from the distal end of the elongated body, a sliding inserter movably connected to the elongated body such that the sliding inserter is configured to move between the proximal end and the distal end of the elongated body, a first channel extending from the proximal end to the distal end, a second channel extending from the distal end to a position between the distal end and the proximal end along the elongated body, the second channel extending at an angle relative to the first channel, and a convergence area at the distal end where the first channel and the second channel intersect;
inserting a suture anchor loaded on an anchor driver into the first channel;
inserting a drill bit into an opening on the sliding inserter and an opening on elongated body, which extends into the second channel;
positioning a distal end of the distal guide tube against a bone;
extending the drill bit through the second channel, the convergence area and the distal guide tube; and
drilling a pilot hole into the bone with the drill bit.

19. The method of claim 18, further comprising the steps of:
retracting the drill bit past the opening on the sliding inserter; and extending the anchor driver through the first channel and the convergence area.

20. The method of claim 19, further comprising the step of implanting the suture anchor into the pilot hole.

* * * * *